United States Patent
Ding et al.

(10) Patent No.: US 9,938,272 B2
(45) Date of Patent: Apr. 10, 2018

(54) HYDRAZINE COMPOUND AS BLOOD COAGULATION FACTOR XA INHIBITOR

(71) Applicant: NORTH CHINA PHARMACEUTICAL COMPANY., LTD., Shijiazhuang, Hebei (CN)

(72) Inventors: Zhaozhong Ding, Shanghai (CN); Guanghua Lai, Shanghai (CN); Shuhui Chen, Shanghai (CN); Xiaobing Yan, Shanghai (CN)

(73) Assignee: North China Pharmaceutical Company., Ltd., Shijiazhuang (CN)

( * ) Notice: Subject to any disclaimer, the term of this patent is extended or adjusted under 35 U.S.C. 154(b) by 0 days.

(21) Appl. No.: 15/312,901

(22) PCT Filed: May 18, 2015

(86) PCT No.: PCT/CN2015/079142
§ 371 (c)(1),
(2) Date: Nov. 21, 2016

(87) PCT Pub. No.: WO2015/176625
PCT Pub. Date: Nov. 26, 2015

(65) Prior Publication Data
US 2017/0152259 A1  Jun. 1, 2017

(30) Foreign Application Priority Data

May 22, 2014 (CN) .......... 2014 1 0220616
May 12, 2015 (CN) .......... 2015 1 0240445

(51) Int. Cl.
*C07D 471/04* (2006.01)
*C07D 413/14* (2006.01)

(52) U.S. Cl.
CPC ......... *C07D 471/04* (2013.01); *C07D 413/14* (2013.01)

(58) Field of Classification Search
CPC .................. C07D 471/04; C07D 413/14
See application file for complete search history.

(56) References Cited

U.S. PATENT DOCUMENTS

| | | | | |
|---|---|---|---|---|
| 6,020,357 A | 2/2000 | Pinto et al. | | |
| 6,413,980 B1 | 7/2002 | Fevig et al. | | |
| 6,548,525 B2 * | 4/2003 | Galemmo, Jr. | ...... | C07D 231/14 514/359 |
| 6,989,391 B2 * | 1/2006 | Pinto | .................... | C07D 211/40 514/303 |
| 8,188,120 B2 * | 5/2012 | Pinto | .................... | C07D 213/75 514/336 |
| 8,470,854 B2 * | 6/2013 | Pinto | .................... | C07D 213/75 514/336 |
| 2003/0004167 A1 | 1/2003 | Lam et al. | | |
| 2003/0069237 A1 | 4/2003 | Fevig et al. | | |
| 2003/0153610 A1 | 8/2003 | Straub et al. | | |

(Continued)

FOREIGN PATENT DOCUMENTS

| | | |
|---|---|---|
| CN | 1589270 A | 3/2005 |
| CN | 1639147 A | 7/2005 |

(Continued)

OTHER PUBLICATIONS

Pinto et al (2003): STN International, HCAPLUS database (Columbus, Ohio), Accession No. 2003: 1014587.*
English translation of priority document CN201410220616.X.
English translation of priority document CN201510240445.1.
Stephen M. Berge et al., Pharmaceutical Salts, J.Pharm.Sci., 66(1), p. 1-19.
Hubert Maehr, A Proposed Hew Convention for Graphic Presentation of Molecular Geometry and Topography, J.Chem.Ed., 62(2), p. 114-120.
Remington: The Science and Practice of Pharmacy, 21st Ed.
Greene et al. Protective Groups in Organic Synthesis, 3rd Ed.
International Search Report (English) issued in PCT/CN2015/079142.
Written Opinion (English) of the International Searching Authority issued in PCT/CN2015/079142.
The structure of STN 1185358-00-2 cited in International Search Report.

*Primary Examiner* — Golam M Shameem
(74) *Attorney, Agent, or Firm* — Harness, Dickey & Pierce, PLC

(57) ABSTRACT

Provided is a compound of formula (I) or a pharmaceutically acceptable salt thereof, wherein X is selected from a 3-9 membered carbon ring or a ring which is formed by 3-9 membered carbocyclic ring fused with benzo ring, and a 4-10 membered heterocyclic ring or a ring which is formed by 4-10 membered heterocyclic ring fused with benzo ring; Y and Z are independently selected from 4-9 membered saturated heterocyclic rings respectively; $R_{1-3}$ are independently selected from H, F, Cl, Br, I, CN, OH, SH, $NH_2$, CHO, COOH respectively, or selected from the group, optionally substituted by $R_{01}$, consisting of $C_{1-10}$ alkyl, $C_{1-10}$ heteroalkyl, $C_{3-10}$ cyclohydrocarbyl, $C_{3-10}$ heterocyclohydrocarbyl, $C_{1-10}$ alkyl substituted by $C_{3-10}$ cyclohydrocarbyl or $C_{3-10}$ heterocyclohydrocarbyl, and $C_{1-10}$ heteroalkyl substituted by $C_{3-10}$ cyclohydrocarbyl or $C_{3-10}$ heterocyclohydrocarbyl. The compound can be used as an anticoagulant for treating and preventing thrombotic disorders, and can meet the real needs of selectivity and a potent inhibitor for coagulation Xa.

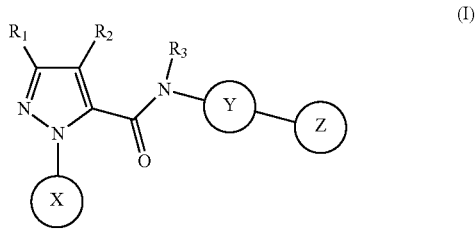

(I)

5 Claims, No Drawings

(56) References Cited

U.S. PATENT DOCUMENTS

| | | |
|---|---|---|
| 2003/0191115 A1 | 10/2003 | Pinto et al. |
| 2004/0038980 A1 | 2/2004 | Lam et al. |
| 2004/0220174 A1 | 11/2004 | Pinto et al. |
| 2005/0124602 A1 | 6/2005 | Pinto et al. |
| 2005/0171085 A1 | 8/2005 | Pinto et al. |
| 2005/0261287 A1 | 11/2005 | Pinto et al. |
| 2005/0267097 A1 | 12/2005 | Pinto et al. |
| 2006/0089496 A1 | 4/2006 | Lam et al. |
| 2007/0135426 A1 | 6/2007 | Pinto et al. |
| 2008/0090807 A1 | 4/2008 | Pinto et al. |
| 2009/0176758 A1 | 7/2009 | Pinto et al. |
| 2010/0119510 A1 | 5/2010 | Pinto et al. |
| 2011/0212930 A1 | 9/2011 | Pinto et al. |
| 2012/0201816 A1 | 8/2012 | Pinto et al. |
| 2014/0113892 A1 | 4/2014 | Pinto et al. |
| 2015/0210691 A1 | 7/2015 | Pinto et al. |

FOREIGN PATENT DOCUMENTS

| | | |
|---|---|---|
| CN | 103242310 | 8/2013 |
| TW | 201341367 A | 10/2013 |
| WO | WO-2003049681 A2 | 6/2003 |
| WO | WO-2004083177 A2 | 9/2004 |

\* cited by examiner

HYDRAZINE COMPOUND AS BLOOD COAGULATION FACTOR Xa INHIBITOR

FIELD OF THE INVENTION

The present invention relates to novel hydrazide compound, especially a compound of formula (I), a process for preparing the compound, a pharmaceutical composition containing the compound, and an use of the compound in the manufacture of a medicament as anticoagulant for treating and preventing thromboembolic disorders.

BACKGROUND OF THE INVENTION

Cardiovascular diseases are the leading cause of morbidity and mortality in developed countries, and most cardiovascular events are primarily due to thrombosis. Use of the first approved oral anticoagulant, warfarin, is plagued by its slow vitamin K-dependent antagonism, by drug-drug interactions, and by drug-food interactions, which results in the need for continuous monitoring for accurate dosing. Other anticoagulants such as heparin and fondaparinux are available only by parenteral administration. Limitations of these agents have prompted extensive research for novel anticoagulants.

Factor Xa is a unique serine protease in the blood coagulation cascade in that it is poised at a common junction where it is activated by both the intrinsic (contact activation) and extrinsic (tissue factor) pathways. In contrast to the multifunctional role that thrombin plays in the cascade, factor Xa only converts prothrombin to thrombin but does not affect the existing level of circulating thrombin. It has been shown that factor Xa inhibitors can exhibit a reduced bleeding risk and offer a superior safety/efficacy profile with respect to thrombin inhibitors in preclinical animal models. Therefore, in the past decade, significant progress has been made in the discovery and development of selective and orally active small-molecule factor Xa inhibitors as anticoagulants for venous or arterial thromboembolism, e.g., prevention of postoperative deep venous thrombosis (DVT) and pulmonary embolism (PE), prevention of stroke during atrial fibrillation, and treatment of acute coronary syndrome (ACS), highlighted by the approval of rivaroxaban represented by chemical formula (B-I) in 2011 (US2003/153610) followed by very recent authorization of apixaban represented by chemical formula (B-II) in 2013 by US FDA (WO2003/049681).

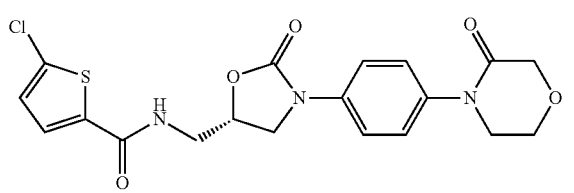

(B-I)

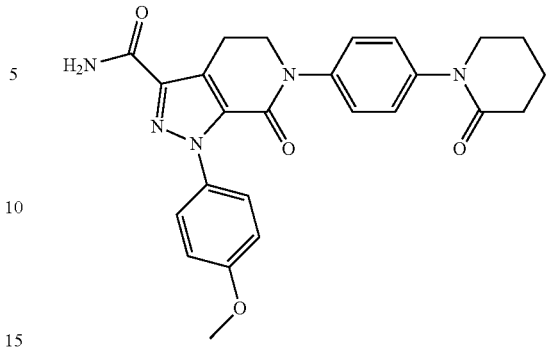

(B-II)

Currently, the standard dose of rivaroxaban is 10 mg once a day for the prevention of venous thromboembolism (VTE) in patients who have undergone elective total hip replacement or total knee replacement surgery. However, the higher efficacy of rivaroxaban is associated with a higher bleeding tendency. The risk of major or fatal bleeding can not be underestimated in particular if the patient needs to prescribe the drug over a long-term period. Furthermore, rivaroxaban has limited water solubility, consequently, it is difficult to develop intravenous formulations.

Difference with Rivaroxaban, the standard dose of apixaban is 5 mg twice a day. Apixaban is rapidly absorbed, reaching Cmax approximately 1-3 hours after administration. After reaching the initial Cmax, the plasma apixaban concentration shows an initial rapid decline and then a more gradual terminal phase, with a mean elimination t½ of 8-15 hours, and apixaban is therefore given twice daily. Apixaban is oxidized to several metabolites and these metabolites are excreted by multiple elimination pathways, including renal and intestinal excretion and metabolism. Concomitant treatment with potent inhibitors of CYP3A4 is contraindicated in apixaban-treated patients. Consequently, improvement in this regard considerably requires wider use of factor Xa inhibitors.

In this regard, great attention has been directed, from a clinical point of view, toward the development of a drug which is highly specific and potent inhibitor for factor Xa, which is more water-soluble, which is more effective in oral administration, more suitable for intravenous administration, and larger therapeutic windows and less bleeding tendency.

DESCRIPTION OF THE INVENTION

The objective of the present invention is to provide a compound of formula (I) or a pharmaceutically acceptable salt, hydrate or prodrug thereof:

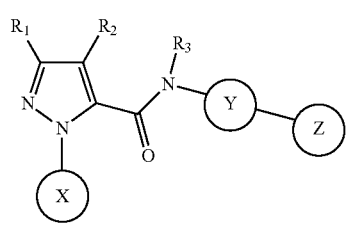

(I)

wherein,

X is selected from 3-9 membered carbocyclic ring or a ring which is formed by 3-9 membered carbocyclic ring fused with benzo ring, 4-10 membered heterocyclic ring or a ring which is formed by 4-10 membered heterocyclic ring fused with benzo ring;

Y and Z are independently selected from 4-9 membered saturated heterocyclic ring respectively;

$R_{1-3}$ are independently selected from H, F, Cl, Br, I, CN, OH, SH, $NH_2$, CHO, COOH respectively, or selected from the group, optionally substituted by $R_{01}$, consisting of $C_{1-10}$ alkyl, $C_{1-10}$ heteroalkyl, $C_{3-10}$ cyclohydrocarbyl, $C_{3-10}$ heterocyclohydrocarbyl, $C_{1-10}$ alkyl substituted by $C_{3-10}$ cyclohydrocarbyl or $C_{3-10}$ heterocyclohydrocarbyl, and $C_{1-10}$ heteroalkyl substituted by $C_{3-10}$ cyclohydrocarbyl or $C_{3-10}$ heterocyclohydrocarbyl;

$R_{01}$ is selected from F, Cl, Br, I, CN, OH, SH, $NH_2$, CHO, COOH, $R_{02}$;

$R_{02}$ is selected from $C_{1-10}$ alkyl, $C_{1-10}$ alkylamino, N,N-di($C_{1-10}$ alkyl) amino, $C_{1-10}$ alkyloxyl, $C_{1-10}$alkylacyl, $C_{1-10}$alkyloxylcarbonyl, $C_{1-10}$alkylsulfonyl, $C_{1-10}$alkylsulfinyl, $C_{3-10}$ cycloalkyl, $C_{3-10}$ cycloalkylamino, $C_{3-10}$ heterocycloalkylamino, $C_{3-10}$ cycloalkyloxyl, $C_{3-10}$ cycloalkylacyl, $C_{3-10}$ cycloalkyloxylcarbonyl, $C_{3-10}$ cycloalkylsulfonyl, $C_{3-10}$ cycloalkylsulfinyl;

heteroatom or heteroatomic group are independently selected from —C(=O)N($R_{d3}$)—, —N($R_{d4}$)—, —C(=N$R_{d5}$)—, —S(=O)$_2$N($R_{d6}$)—, —S(=O) N($R_{d7}$)—, —O—, —S—, =O, =S, —C(=O)O—, —C(=O)—, —C(=S)—, —S(=O)—, and/or —S(=O)$_2$— respectively;

$R_{d3-d7}$ are independently selected from H, $R_{03}$ respectively;

$R_{03}$ is selected from $C_{1-10}$ alkyl, $C_{1-10}$alkylacyl, $C_{1-10}$ alkoxycarbonyl, $C_{1-10}$ alkylsulfonyl, $C_{1-10}$ alkylsulfinyl, $C_{3-10}$ cycloalkyl, $C_{3-10}$ cycloalkylacyl, $C_{3-10}$ cycloalkyloxylcarbonyl, $C_{3-10}$ cycloalkylsulfonyl, $C_{3-10}$ cycloalkylsulfinyl;

$R_{02}$ and $R_{03}$ are optionally substituted by $R_{001}$;

$R_{001}$ is selected from F, Cl, Br, I, CN, OH, $N(CH_3)_2$, $NH(CH_3)$, $NH_2$, CHO, COOH, $CF_3$, $(NH_2)CH_2$, $(HO)CH_2$, $CH_3$, $CH_3O$, HC(=O), $CH_3OC$(=O), $CH_3S$(=O)$_2$, $CH_3S$(=O);

the number of $R_{01}$, $R_{001}$, heteroatom, or heteroatomic group is independently selected from 0, 1, 2, or 3 respectively;

optionally, $R_1$ and $R_2$, or $R_2$ and $R_3$ are taken together with the same carbon atom or hetero atom to form a 5-7 membered ring.

In an embodiment of this invention, the X is selected from

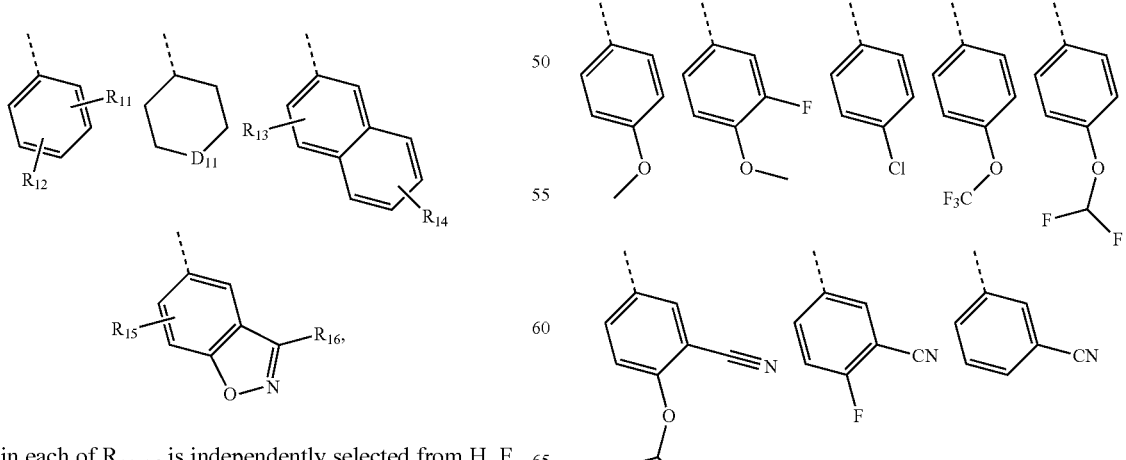

wherein each of $R_{11-16}$ is independently selected from H, F, Cl, Br, I, CN, OH, SH, $NH_2$, CHO, COOH respectively, or selected from the group, optionally substituted by $R_{01}$, consisting of $C_{1-10}$ alkyl, $C_{1-10}$ heteroalkyl, $C_{3-10}$ cyclohydrocarbyl, $C_{3-10}$ heterocyclohydrocarbyl, $C_{1-10}$ alkyl substituted by $C_{3-10}$ cyclohydrocarbyl or $C_{3-10}$ heterocyclohydrocarbyl, and $C_{1-10}$ heteroalkyl substituted by $C_{3-10}$ cyclohydrocarbyl or $C_{3-10}$ heterocyclohydrocarbyl;

$D_{11}$ is selected from —C($R_{d1}$)($R_{d2}$)—, —C(=O)N ($R_{d3}$)—, —N($R_{d4}$)—, —C(=N$R_{d5}$)—, —S(=O)$_2$N ($R_{d6}$)—, —S(=O)N($R_{d7}$)—, —O—, —S—, —C(=O)O—, —C(=O)—, —C(=S)—, —S(=O)—, or —S(=O)$_2$—;

$R_{d1}$ and $R_{d2}$ are independently selected from H, F, Cl, Br, I, CN, OH, SH, $NH_2$, CHO, COOH respectively, or selected from the group, optionally substituted by $R_{01}$, consisting of $C_{1-10}$alkyl, $C_{1-10}$ heteroalkyl, $C_{3-10}$ cyclohydrocarbyl, $C_{3-10}$ heterocyclohydrocarbyl, $C_{1-10}$ alkyl substituted by $C_{3-10}$ cyclohydrocarbyl or $C_{3-10}$ heterocyclohydrocarbyl, and $C_{1-10}$ heteroalkyl substituted by $C_{3-10}$ cyclohydrocarbyl or $C_{3-10}$ heterocyclohydrocarbyl.

In an embodiment of this invention, the X is selected from

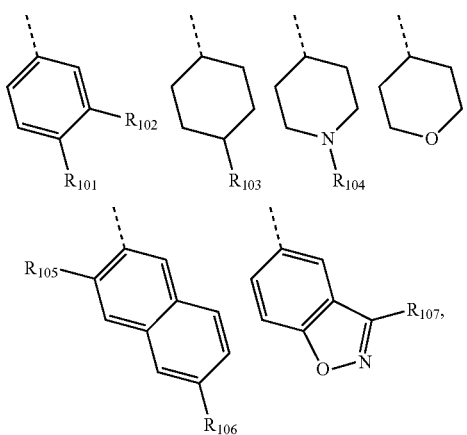

in which $R_{101-107}$ are independently selected from $CH_3O$—, F, Cl, CN, $NH_2$, $CF_3O$—, $CHF_2O$—, —C(=O)$NH_2$, $CH_3S$(=O)$_2$— respectively.

In an embodiment of this invention, the X is selected from

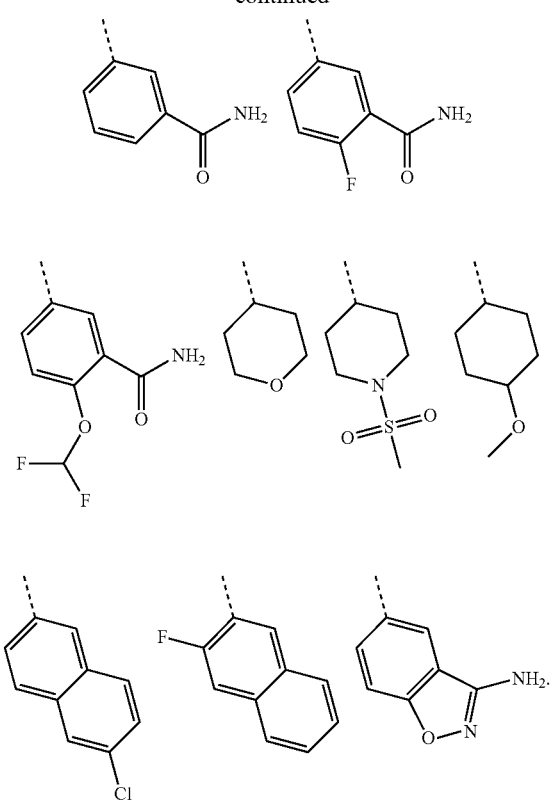

In an embodiment of this invention, the structure unit

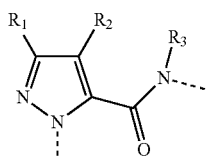

is selected from

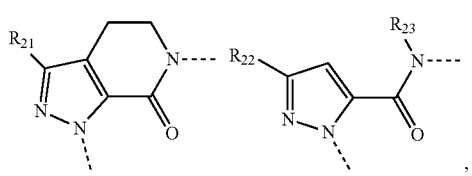

in which R$_{21-23}$ are independently selected from H, F, Cl, Br, I, CN, OH, SH, NH$_2$, CHO, COOH respectively, or selected from the group, optionally substituted by R$_{01}$, consisting of C$_{1-10}$ alkyl, C$_{1-10}$ heteroalkyl, C$_{3-10}$ cyclohydrocarbyl, C$_{3-10}$ heterocyclohydrocarbyl, C$_{1-10}$ alkyl substituted by C$_{3-10}$ cyclohydrocarbyl or C$_{3-10}$ heterocyclohydrocarbyl, and C$_{1-10}$ heteroalkyl substituted by C$_{3-10}$ cyclohydrocarbyl or C$_{3-10}$ heterocyclohydrocarbyl.

In an embodiment of this invention, the R$_{21-23}$ are independently selected from H, CN, CF$_3$, CH$_3$, CH$_3$CH$_2$, cyclopropyl, —C(=O)NH$_2$,

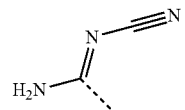

respectively.

In an embodiment of this invention, the structure unit

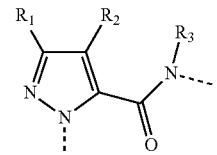

is selected from

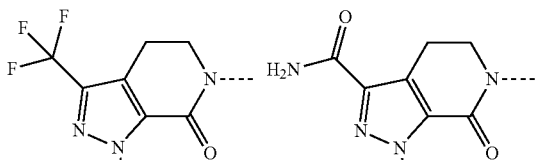

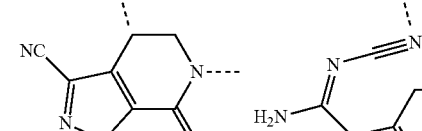

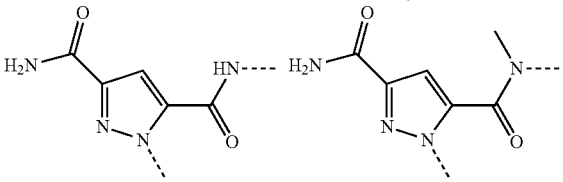

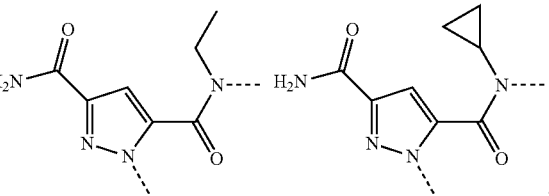

In an embodiment of this invention, the Y is selected from

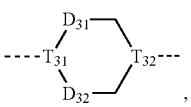

in which,

T$_{31-32}$ are independently selected from N or C(R$_t$) respectively;

D$_{31-32}$ are independently selected from single bond, —C(R$_{d1}$)(R$_{d2}$)—, —C(=O)N(R$_{d3}$)—, —N(R$_{d4}$)—, —C(=NR$_{d5}$)—, —S(=O)$_2$N(R$_{d6}$)—, —S(=O)N(R$_{d7}$)—, —O—, —S—, —C(=O)O—, —C(=O)—, —C(=S)—, —S(=O)— or —S(=O)$_2$— respectively, and $D_{31}$ and $D_{32}$ are not single bond at the same time;

$R_t$, $R_{d1}$ and $R_{d2}$ are independently selected from H, F, Cl, Br, I, CN, OH, SH, NH$_2$, CHO, COOH respectively, or selected from the group, optionally substituted by $R_{01}$, consisting of $C_{1-10}$alkyl, $C_{1-10}$ heteroalkyl, $C_{3-10}$ cyclohydrocarbyl, $C_{3-10}$ heterocyclohydrocarbyl, $C_{1-10}$ alkyl substituted by $C_{3-10}$ cyclohydrocarbyl or $C_{3-10}$ heterocyclohydrocarbyl, and $C_{1-10}$ heteroalkyl substituted by $C_{3-10}$ cyclohydrocarbyl or $C_{3-10}$ heterocyclohydrocarbyl; when $D_{31-32}$ is selected from $C(R_{d1})(R_{d2})$, $D_{31}$ and $D_{32}$ are optionally taken together to form a 3-6 membered ring.

In an embodiment of this invention, the Y is selected from

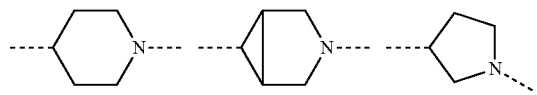

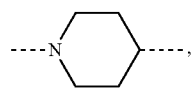

In an embodiment of this invention, the Z is selected from

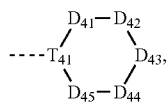

in which, $T_{41}$ is selected from N or $C(R_t)$;

None to three of $D_{41-45}$ are independently selected from single bond, —C(=O)N(R$_{d3}$)—, —N(R$_{d4}$)—, —C(=NR$_{d5}$)—, —S(=O)$_2$N(R$_{d6}$)—, —S(=O)N(R$_{d7}$)—, —O—, —S—, —C(=O)O—, —C(=O)—, —C(=S)—, —S(=O)— or —S(=O)$_2$— respectively, the other are selected from $C(R_{d1})(R_{d2})$;

$R_t$, $R_{d1}$ and $R_{d2}$ are independently selected from H, F, Cl, Br, I, CN, OH, SH, NH$_2$, CHO, COOH respectively, or selected from the group, optionally substituted by $R_{01}$, consisting of $C_{1-10}$alkyl, $C_{1-10}$ heteroalkyl, $C_{3-10}$ cyclohydrocarbyl, $C_{3-10}$ heterocyclohydrocarbyl, $C_{1-10}$ alkyl substituted by $C_{3-10}$ cyclohydrocarbyl or $C_{3-10}$ heterocyclohydrocarbyl, and $C_{1-10}$ heteroalkyl substituted by $C_{3-10}$ cyclohydrocarbyl or $C_{3-10}$ heterocyclohydrocarbyl.

In an embodiment of this invention, the Z is selected from

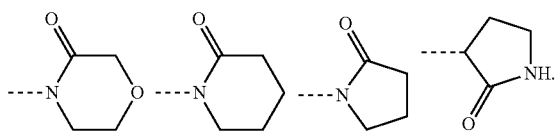

In an embodiment of this invention, the structures of the compound or pharmaceutically acceptable salts thereof are as follows in formula (II) or formula (III):

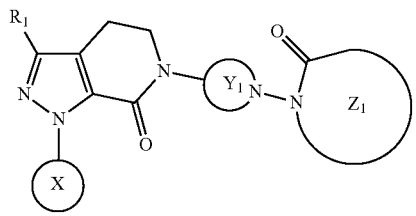

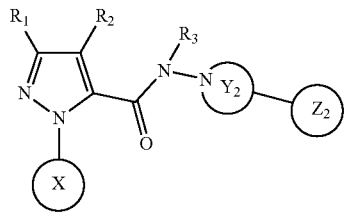

wherein, $Y_1$, $Y_2$ are each independently represent 4-9 membered saturated N-containing heterocycle, $Z_1$ represents 4-9 membered saturated heterocycle including an amide bond, $Z_2$ represents 4-9 membered saturated heterocyclic ring.

In an embodiment of this invention, the compound or pharmaceutically acceptable salts thereof are selected from:

1) 4-(4-(1-(4-Methoxyphenyl)-7-oxo-3-(trifluoromethyl)-4,5-dihydro-1H-pyrazolo[3,4-c]pyridin-6(7H)-yl)piperidin-1-yl)morpholin-3-one;
2) 1-(4-Methoxyphenyl)-6-(2'-oxo-[1,1'-bipiperidin]-4-yl)-3-(trifluoromethyl)-5,6-dihydro-1H-pyrazolo[3,4-c]pyridin-7(4H)-one;
3) 1-(4-Methoxyphenyl)-6-(1-(2-oxopyrrolidin-1-yl)piperidin-4-yl)-3-(trifluoromethyl)-5, 6-dihydro-1H-pyrazolo[3,4-c]pyridin-7(4H)-one;
4) 1-(4-Methoxyphenyl)-7-oxo-6-(2'-oxo-[1,1'-bipiperidin]-4-yl)-4,5,6,7-tetrahydro-1H-pyrazolo[3,4-c]pyridine-3-carboxamide;
5) 1-(4-Methoxyphenyl)-7-oxo-6-(2'-oxo-[1,1'-bipiperidin]-4-yl)-4,5,6,7-tetrahydro-1H-pyrazolo[3,4-c]pyridine-3-carbonitrile;
6) N'-Cyano-1-(4-methoxyphenyl)-7-oxo-6-(2'-oxo-[1,1'-bipiperidin]-4-yl)-4,5,6,7-tetrahydro-1H-pyrazolo[3,4-c]pyridine-3-carboximidamide;
7) 1-(4-Methoxyphenyl)-7-oxo-6-(1-(3-oxomorpholino)piperidin-4-yl)-4,5,6,7-tetrahydro-1H-pyrazolo[3,4-c]pyridine-3-carboxamide;
8) 1-(4-Methoxyphenyl)-7-oxo-6-(1-(2-oxopyrrolidin-3-yl)piperidin-4-yl)-4,5,6,7-tetrahydro-1H-pyrazolo[3,4-c]pyridine-3-carboxamide;
9) 1-(4-Chlorophenyl)-7-oxo-6-(1-(3-oxomorpholino)piperidin-4-yl)-4,5,6,7-tetrahydro-1H-pyrazolo[3,4-c]pyridine-3-carboxamide;
10) 7-Oxo-6-(1-(3-oxomorpholino)piperidin-4-yl)-1-(4-(trifluoromethoxy)phenyl)-4,5,6,7-tetrahydro-1H-pyrazolo[3,4-c]pyridine-3-carboxamide;
11) 1-(4-(Difluoromethoxy)phenyl)-7-oxo-6-(1-(3-oxomorpholino)piperidin-4-yl)-4,5,6,7-tetrahydro-1H-pyrazolo[3,4-c]pyridine-3-carboxamide;
12) 1-(4-Methoxyphenyl)-7-oxo-6-(3-(2-oxopiperidin-1-yl)-3-azabicyclo[3.1.0]hexan-6-yl)-4,5,6,7-tetrahydro-1H-pyrazolo[3,4-c]pyridine-3-carboxamide;
13) 1-(4-Methoxyphenyl)-7-oxo-6-(3-(3-oxomorpholino)-3-azabicyclo[3.1.0]hexan-6-yl)-4, 5,6,7-tetrahydro-1H-pyrazolo[3,4-c]pyridine-3-carboxamide;

14) 1-(4-Methoxyphenyl)-7-oxo-6-(2-oxo-[1,4'-bipiperidin]-1'-yl)-4,5,6,7-tetrahydro-1H-pyrazolo[3,4-c]pyridine-3-carboxamide;
15) 1-(4-Methoxyphenyl)-$N^5$-(1-(3-oxomorpholino)piperidin-4-yl)-1H-pyrazole-3,5-dicarboxamide;
16) 1-(4-Methoxyphenyl)-$N^5$-methyl-$N^5$-(1-(3-oxomorpholino)piperidin-4-yl)-1H-pyrazole-3,5-dicarboxamide;
17) $N^5$-Ethyl-1-(4-methoxyphenyl)-$N^5$-(1-(3-oxomorpholino)piperidin-4-yl)-1H-pyrazole-3,5-dicarboxamide;
18) $N^5$-cyclopropyl-1-(4-methoxyphenyl)-$N^5$-(1-(3-oxomorpholino)piperidin-4-yl)-1H-pyrazole-3,5-dicarboxamide;
19) 1-(4-Methoxyphenyl)-$N^5$-(1-(3-oxomorpholino)pyrrolidin-3-yl)-1H-pyrazole-3,5-dicarboxamide;
20) $N^5$-(1-(3-oxomorpholino)piperidin-4-yl)-1-(tetrahydro-2H-pyran-4-yl)-1H-pyrazole-3,5-dicarboxamide;
21) 1-(1-(Methylsulfonyl)piperidin-4-yl)-$N^5$-(1-(3-oxomorpholino)piperidin-4-yl)-1H-pyrazole-3,5-dicarboxamide;
22) 1-(4-Methoxycyclohexyl)-$N^5$-(1-(3-oxomorpholino)piperidin-4-yl)-1H-pyrazole-3,5-dicarboxamide;
23) 4-(4-(1-(4-(Difluoromethoxy)phenyl)-7-oxo-3-(trifluoromethyl)-4,5-dihydro-1H-pyrazolo[3,4-c]pyridin-6(7H)-yl)piperidin-1-yl)morpholin-3-one;
24) 4-(4-(1-(6-Chloronaphthalen-2-yl)-7-oxo-3-(trifluoromethyl)-4,5-dihydro-1H-pyrazolo[3,4-c]pyridin-6(7H)-yl)piperidin-1-yl)morpholin-3-one;
25) 2-Fluoro-5-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzonitrile;
26) 4-(4-(1-(3-Aminobenzo[d]isoxazol-5-yl)-7-oxo-3-(trifluoromethyl)-4,5-dihydro-1H-pyrazolo[3,4-c]pyridin-6(7H)-yl)piperidin-1-yl)morpholin-3-one;
27) 3-(7-Oxo-6-(1-(3-oxomorpholino)piperidin-4-yl)-3-(trifluoromethyl)-4,5,6,7-tetrahydro-1H-pyrazolo[3,4-c]pyridin-1-yl)benzonitrile;
28) 4-(4-(1-(3-Fluoro-4-methoxyphenyl)-7-oxo-3-(trifluoromethyl)-4,5-dihydro-1H-pyrazolo[3,4-c]pyridin-6(7H)-yl)piperidin-1-yl)morpholin-3-one;
29) 4-(4-(1-(3-Fluoronaphthalen-2-yl)-7-oxo-3-(trifluoromethyl)-4,5-dihydro-1H-pyrazolo[3,4-c]pyridin-6(7H)-yl)piperidin-1-yl)morpholin-3-one;
30) 2-(Difluoromethoxy)-5-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzonitrile;
31) 3-(7-Oxo-6-(1-(3-oxomorpholino)piperidin-4-yl)-3-(trifluoromethyl)-4,5,6,7-tetrahydro-1H-pyrazolo[3,4-c]pyridin-1-yl)benzamide;
32) 2-Fluoro-5-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzamide; and
33) 2-(Difluoromethoxy)-5-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzamide.

Another objective of the present invention is to provide a process for preparing the compound of formula (I), comprising a route which is as follows:

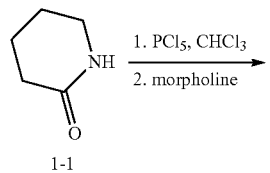

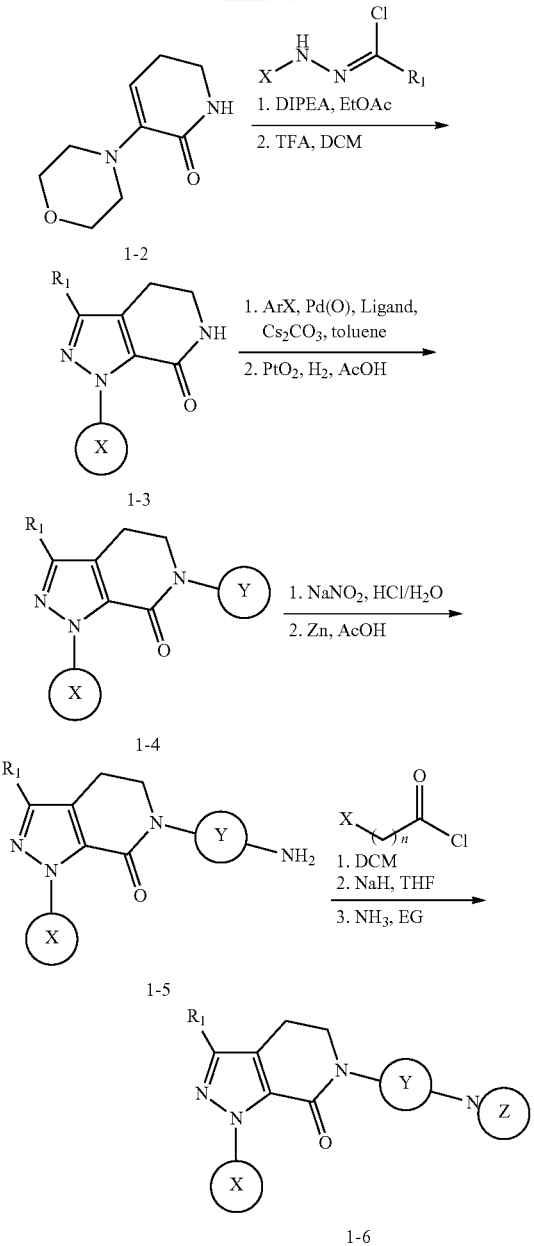

wherein $R^1$, X, Y, Z are defined as above.

Another objective of the present invention is to provide a pharmaceutical composition comprising therapeutically effective amount of the compound of formula (I) or a pharmaceutically acceptable salts, hydrates or prodrugs thereof and pharmaceutical acceptable carriers.

Another objective of the present invention is to provide an use in the preparation of a medicament for treating a thromboembolic disorder, which is preferably selected from arterial cardiovascular thromboembolic disorders, venous cardiovascular thromboembolic disorders, arterial cerebrovascular thromboembolic disorders, and venous cerebrovascular thromboembolic disorders; more preferably selected from unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

The present invention may be embodied in other specific forms without departing from the spirit or essential attributes thereof, which encompasses all combinations of preferred aspects of the invention noted herein. It is understood that any and all embodiments of the present invention may be taken in conjunction with any other embodiment or embodiments to describe additional more preferred embodiments, of which the special technical feature may be taken in conjunction with any other related technical feature to describe new embodiments. Of course, it is understood that every preferred embodiment is independent, of which the special technical feature is limited to the preferred embodiment itself.

DEFINITIONS AND ILLUSTRATIONS $C_{1-10}$ is selected from $C_1$, $C_2$, $C_3$, $C_4$, $C_5$, $C_6$, $C_7$, $C_8$, $C_9$, and $C_{10}$; $C_{3-10}$ is selected from $C_3$, $C_4$, $C_5$, $C_6$, $C_7$, $C_8$, $C_9$, and $C_{10}$.

$C_{1-10}$ alkyl, $C_{1-10}$ heteroalkyl, $C_{3-10}$ cyclohydrocarbyl, $C_{3-10}$ heterocyclohydrocarbyl, $C_{1-10}$ alkyl substituted by $C_{3-10}$ cyclohydrocarbyl or $C_{3-10}$ heterocyclohydrocarbyl, and $C_{1-10}$ heteroalkyl substituted by $C_{3-10}$ cyclohydrocarbyl or $C_{3-10}$ heterocyclohydrocarbyl include, but are not limited to:

$C_{1-10}$ alkyl, $C_{1-10}$ alkylamino, N,N-di($C_{1-10}$ alkyl) amino, $C_{1-10}$ alkyloxyl, $C_{1-10}$ alkylacyl, $C_{1-10}$ alkyloxylcarbonyl, $C_{1-10}$ alkylsulfonyl, $C_{1-10}$ alkylsulfinyl, $C_{3-10}$ cycloalkyl, $C_{3-10}$ cycloalkylamino, $C_{3-10}$ heterocycloalkylamino, $C_{3-10}$ cycloalkyloxyl, $C_{3-10}$ cycloalkylacyl, $C_{3-10}$ cycloalkyloxylcarbonyl, $C_{3-10}$ cycloalkylsulfonyl, and $C_{3-10}$ cycloalkylsulfinyl;

methyl, ethyl, n-propyl, isopropyl, —CH$_2$C(CH$_3$)(CH$_3$)(OH), cyclopropyl, cyclobutyl, propylmethylene, cycropylacyl, benzyloxyl, trifluoromethyl, aminomethyl, hydroxylmethyl, methyloxyl, formyl, methyloxylcarbonyl, methylsulfonyl, methylsulfinyl, ethyloxyl, acetyl, ethylsulfonyl, ethyloxylcarbonyl, dimethylamino, diethylamino, dimethylaminocarbonyl, and diethylaminocarbonyl;

N(CH$_3$)$_2$, NH(CH$_3$), —CH$_2$CF$_3$, —CH$_2$CH$_2$CF$_3$, —CH$_2$CH$_2$F, —CH$_2$CH$_2$S(=O)$_2$CH$_3$, —CH$_2$CH$_2$CN,

—CH$_2$CH(OH)(CH$_3$)$_2$ —CH$_2$CH(F)(CH$_3$)$_2$, —CH$_2$CH$_2$F, —CH$_2$CF$_3$, —CH$_2$CH$_2$CF$_3$, —CH$_2$CH$_2$NH$_2$, —CH$_2$CH$_2$OH, —CH$_2$CH$_2$CH$_3$, —CH$_2$CH$_2$CH$_2$CH$_3$, —CH$_2$CH$_2$N(CH$_3$)$_2$, —S(=O)$_2$CH$_3$, —CH$_2$CH$_2$S(=O)$_2$CH$_3$,

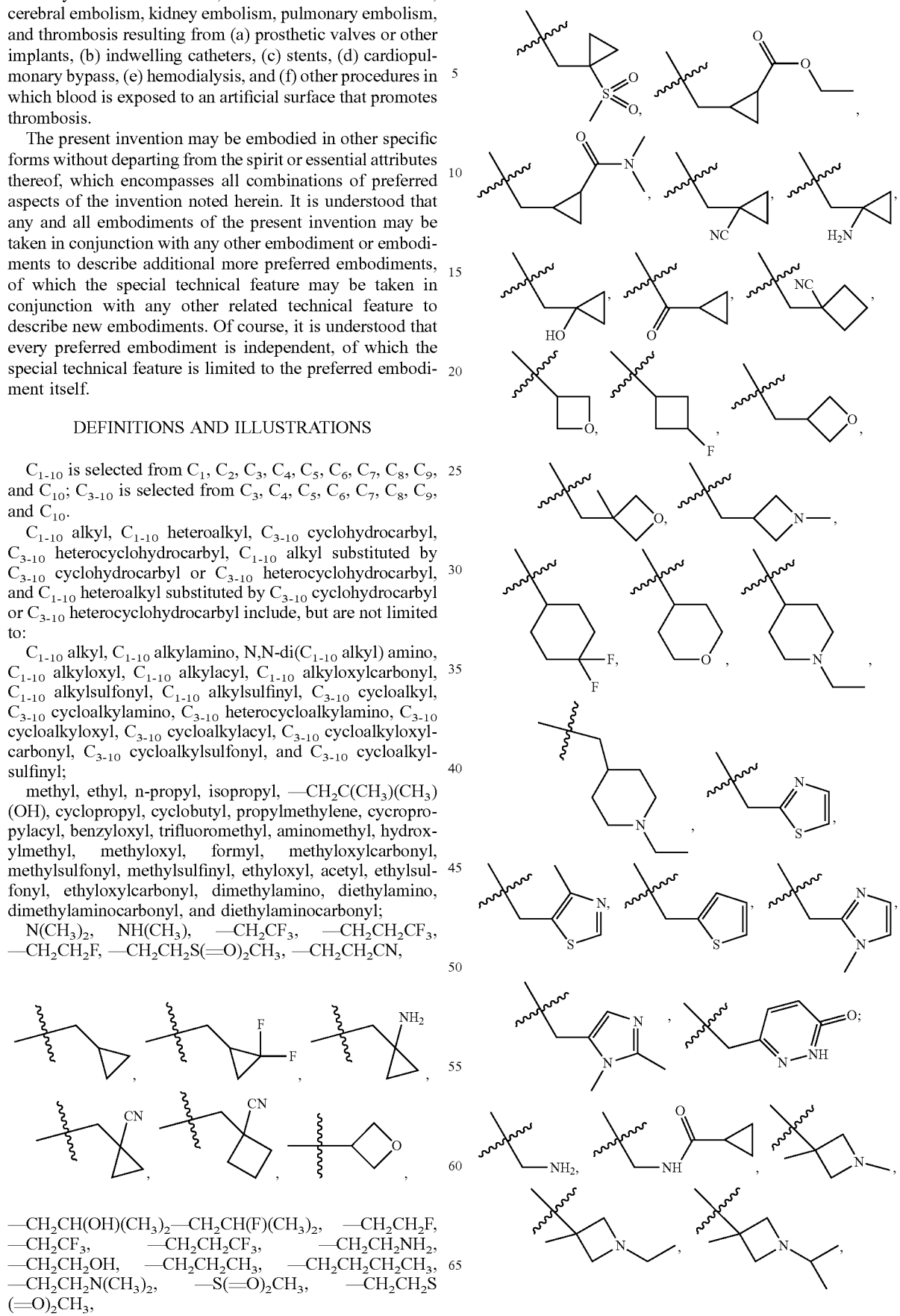

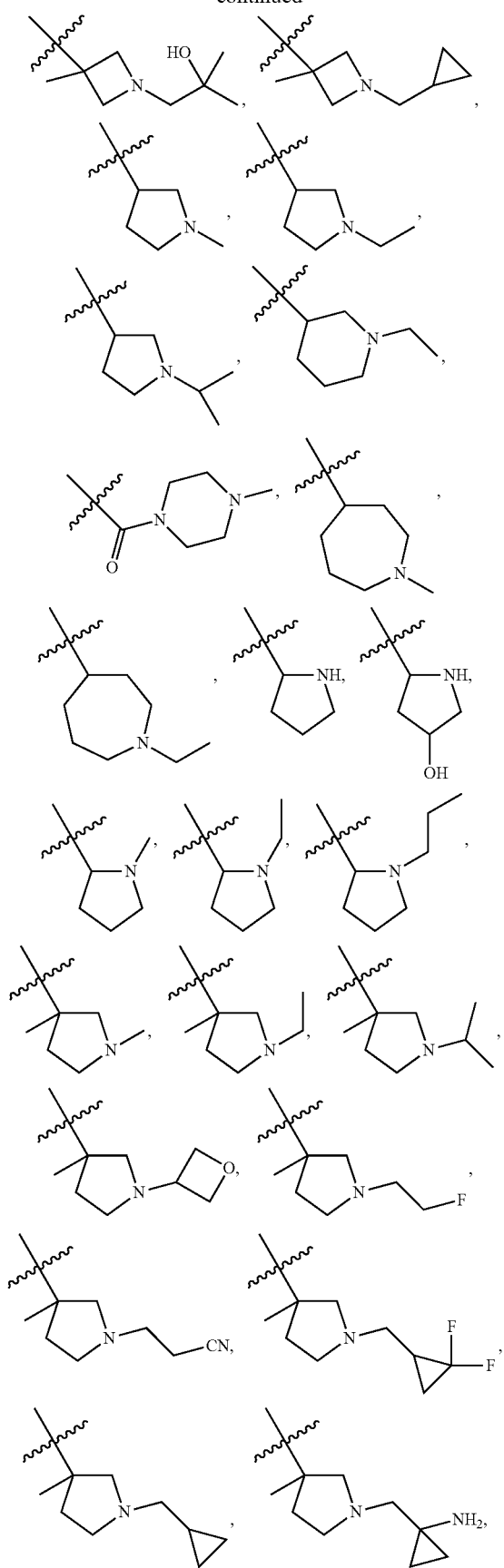
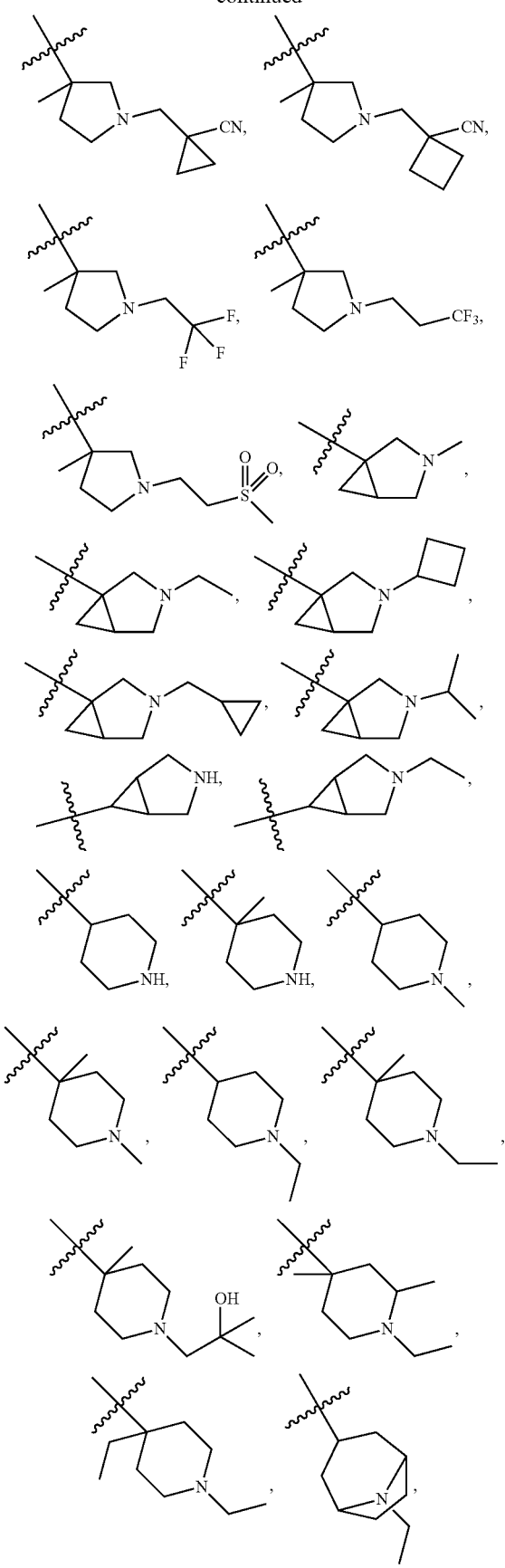

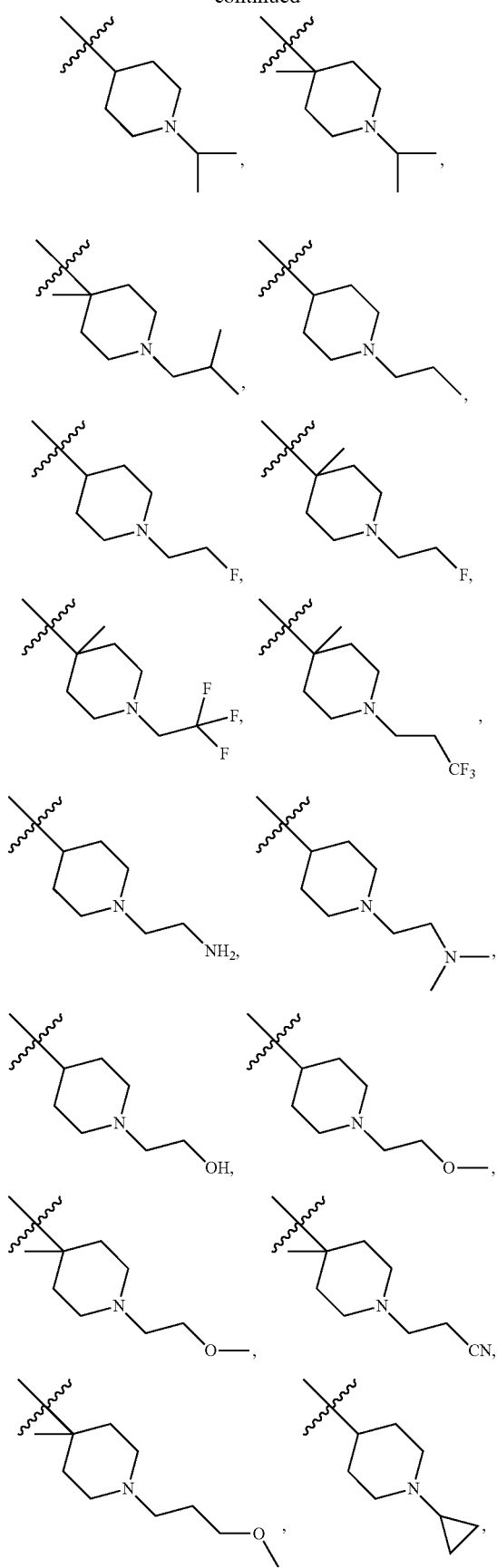
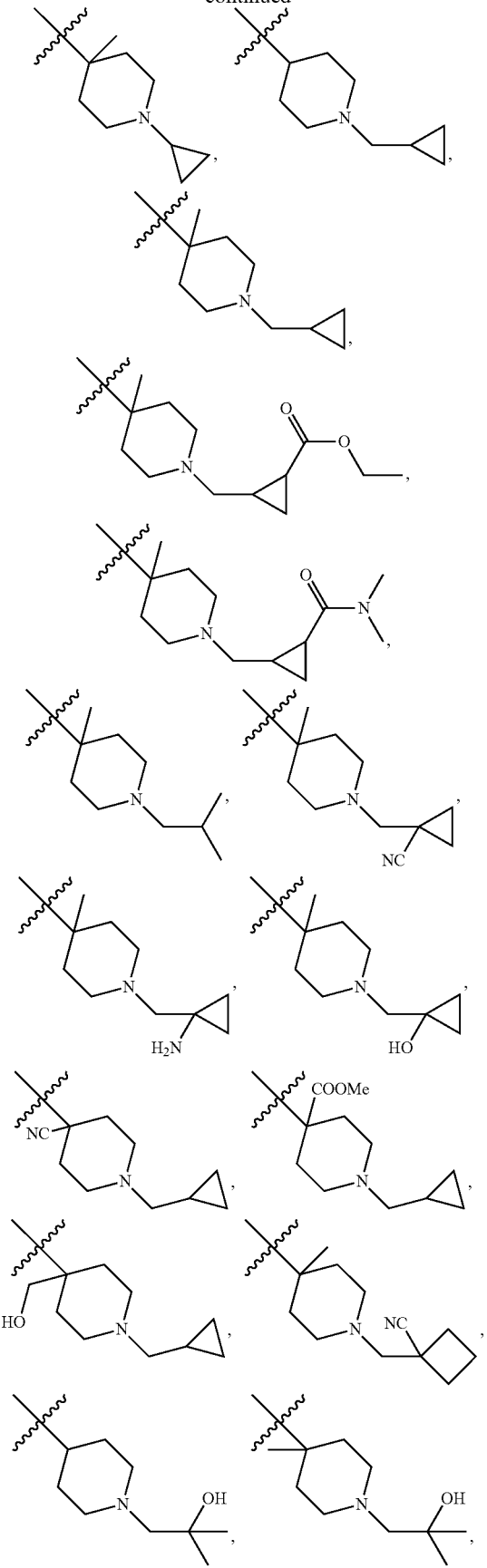

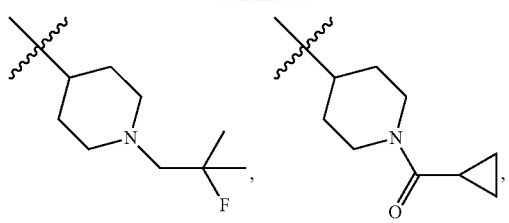
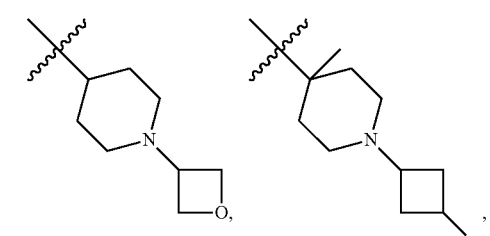
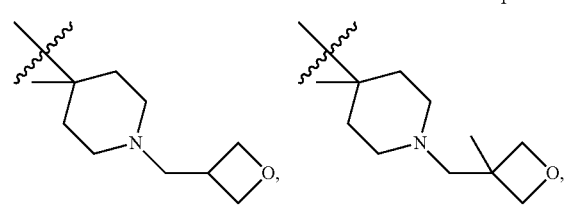
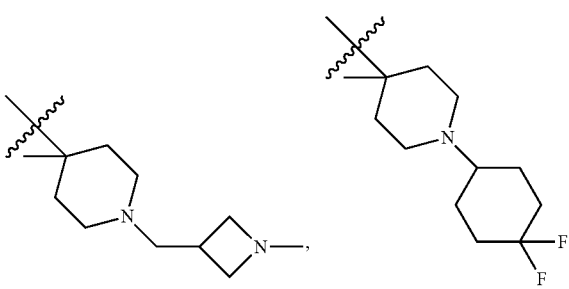
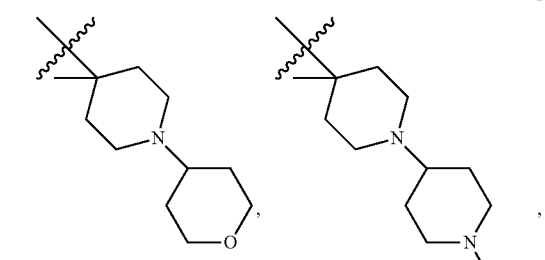
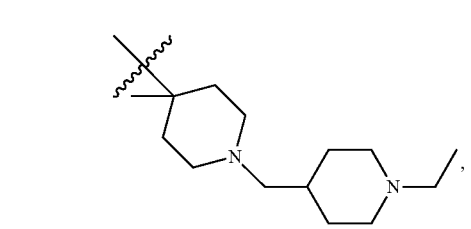
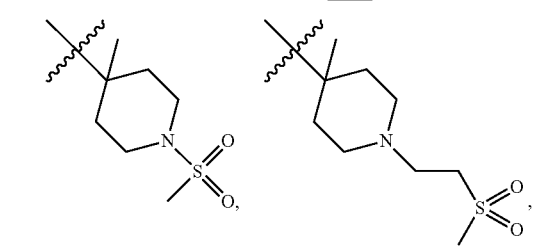
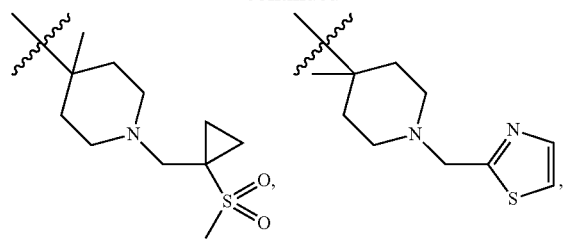
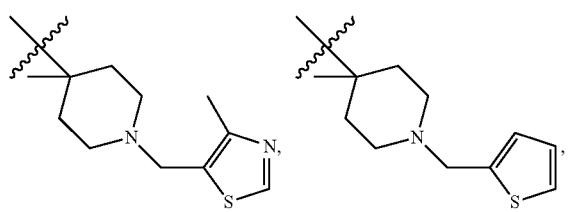
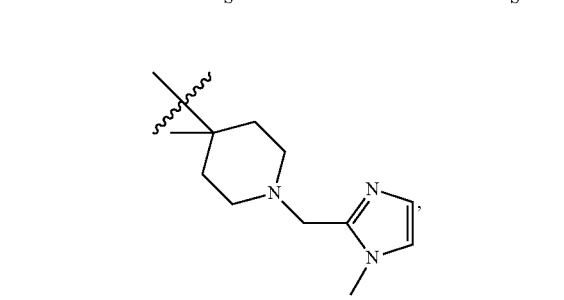
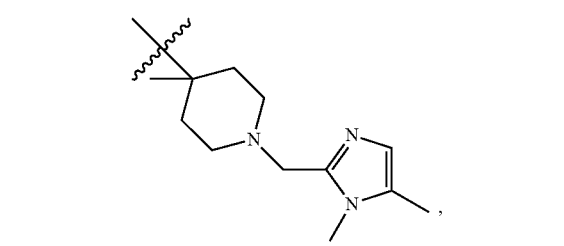
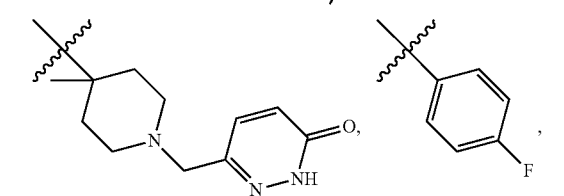
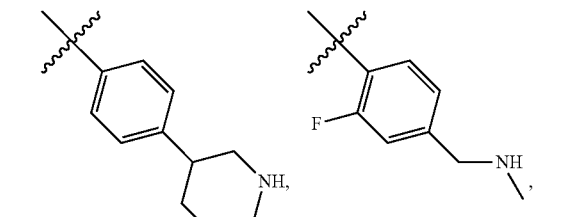
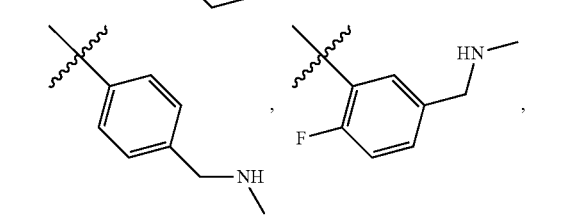

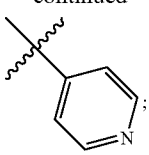

and phenyl, thiazolyl, biphenyl, naphthyl group, a cyclopentyl group, a furyl group, a 3-pyrrolinyl, pyrrolidinyl, 1,3-dioxolanyl, pyrazolyl, 2-pyrazolinyl, pyrazolidinyl, imidazolyl, oxazolyl, thiazolyl, 1,2,3-azolyl, 1,2,3-triazolyl, 1,2,4-triazolyl, 1,3,4-thiadiazolyl, 4H-pyranyl, pyridyl, piperidinyl, 1,4-dioxanyl, morpholinyl, pyridazinyl, pyrimidinyl, pyrazinyl, piperazinyl, 1,3,5-trithianyl, 1,3,5-triazinyl, benzofuranyl, benzothienyl, indolyl, benzimidazolyl, benzothiazolyl, purinyl, quinolinyl, iso-quinolinyl, cinnolinyl, and quinoxalinyl;

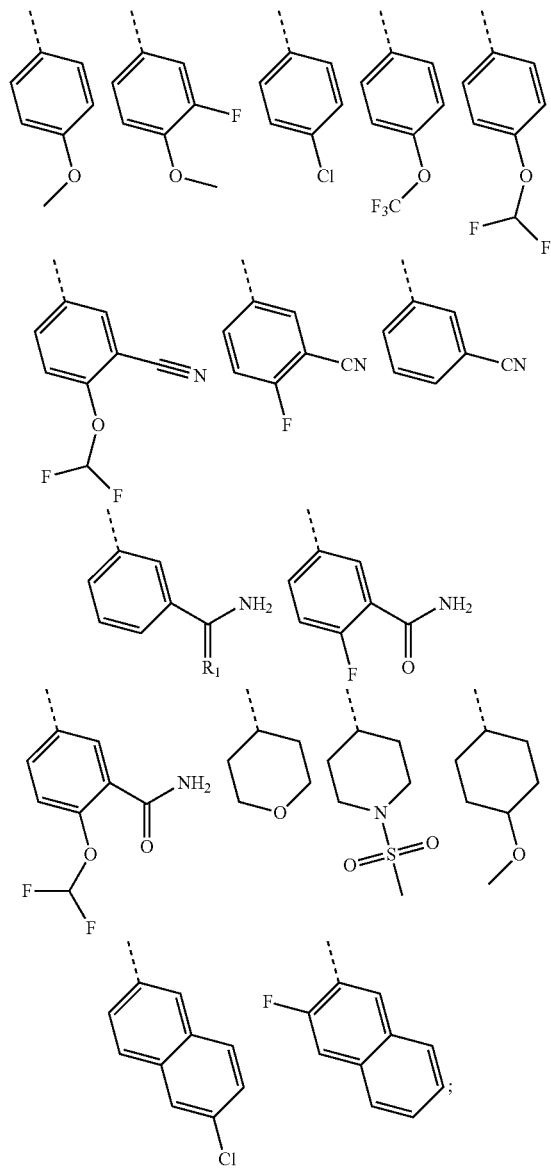

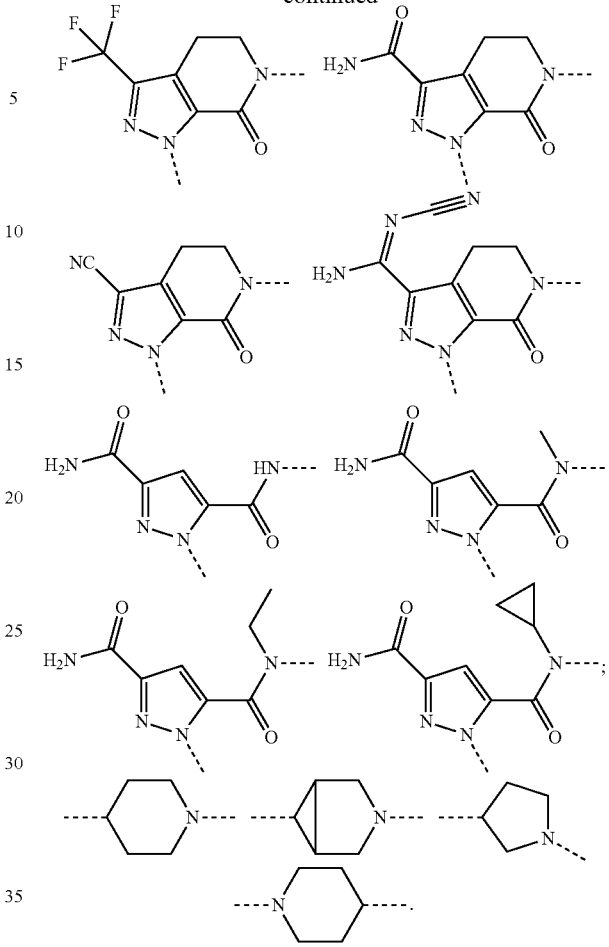

The term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" is meant to include a salt of a compound of the invention which are prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either in a neat solution or suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either in a neat solution or suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, hydrobromic, hydrochloric, hydroiodide, hydroxy, hydroxynaphthoic, isethionic, lactic, lactobionic, lauryl sulfonic, maleic, malic, mandelic, methane sulfonic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic acid.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred.

In addition to salt forms, the present invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the present invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the present invention.

The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and D and L isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished by using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium (3H), iodine-125 (125I) or carbon-14 (14C). All isotopic variations of the compounds of the invention, whether radioactive or not, are intended to be encompassed within the scope of the present invention.

The term "pharmaceutically acceptable carrier" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in Remington: The Science and Practice of Pharmacy, 21st Ed., Lippincott, Williams & Wilkins (2005) which is incorporated herein by reference.

The term "excipients" is conventionally known to mean carriers, diluents and/or vehicles used in formulating drug compositions effective for the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The term "substituted", as used herein, means that any one or more hydrogens on the designated atom is replaced with a selection from the indicated group, including deuterium "D" atom, a variant of hydrogen, provided that the designated atom's normal valency is not exceeded, and that the substitution results in a stable compound. When a substituent is keto (i.e., =O), then 2 hydrogens on the atom are replaced. Keto substituents are not present on aromatic moieties. The term "optionally substituted", as used herein, means that the designated atom can be substituted or unsubstituted by the substituents, and unless otherwise stated, the species and number the substituents are not defined provided that they can be achieved in Chemistry.

When any variable (e.g., R) occurs more than one time in any constituent or formula for a compound, its definition at each occurrence is independent of its definition at every other occurrence. Thus, for example, if a group is shown to be substituted with 0-2 R, then said group may optionally be substituted with up to two R groups and R at each occurrence is selected independently from the definition of R. Also, combinations of substituents and/or variables are permissible only if such combinations result in stable compounds.

When one of the variables is selected from a single bond, it means that two groups connected with the variable directly connect with each other. For example, when the L of A-L-Z represents single bond, it means the structure actually is A-Z.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds. For example, structure unit

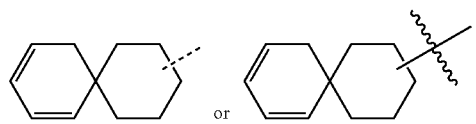

or means that any position of the cyclohexyl or cyclohexadienyl could be substituted. Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —R', —OR', =O, =NR', =N—OR', —NR'R", —SR', -halogen, —SiR'R"R''', OC(O)R', —C(O)R', —CO$_2$R'—CONR'R", —OC(O)NR'R", —NR"C(O)R', NR'C(O)NR"R''', —NR"C(O)$_2$R', —NR''''—C(NR'R"R''')=NR''', NR''''C(NR'R")=NR''', —S(O)R', —S(O)$_2$R', —S(O)$_2$NR'R", NR"SO$_2$R', —CN, —NO$_2$, —N$_3$, —CH(Ph)$_2$ and (C1-C4)alkyl substituted by fluoro, in a number ranging from zero to (2m'+1), where m' is the total number of carbon atoms in such radical. Each of R', R", R''', R'''' and R''''' preferably independently refers to hydrogen, substituted or unsubstituted heteroalkyl, substituted or unsubstituted aryl, e.g., aryl substituted with 1-3 halogens, substituted or unsubstituted alkyl, alkoxy, thioalkoxy groups, or arylalkyl groups. When a compound of the invention includes more than one R group, for example, each of the R groups is independently selected as are each R', R", R''', R'''' and R''''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$CH$_3$, and the like).

Similar to the substituents described for the alkyl radical, substituents for the aryl and heteroaryl groups are generically referred to as "aryl group substituents." The substituents are selected from, for example: —R', —OR', —NR'R", —SR', -halogen, —SiR'R"R''', OC(O)R', —C(O)R', —CO$_2$R', —CONR'R", —OC(O)NR'R", —NR"C(O)R', NR'C(O)NR"R''', —NR"C(O)$_2$R'—NR''''—C(NR'R"R''')=NR''', NR'''' C(NR'R")=NR''', —S(O)R', —S(O)$_2$R', —S(O)$_2$NR'R", NR"SO$_2$R', —CN, —NO$_2$, —N$_3$, —CH(Ph)$_2$, (C1-C4)alkoxy substituted by fluoro, and (C1-C4)alkyl substituted by fluoro, in a number ranging from zero to the total number of open valences on the aromatic ring system; and where R', R", R''', R'''' and R''''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R'R", R''', R'''' and R''''' groups when more than one of these groups is present.

Two of the substituents on adjacent atoms of the aryl or heteroaryl ring may optionally be replaced with a substituent of the formula -T-C(O)—(CRR')q-U-, wherein T and U are independently selected from —NR—, —O—, —CRR'— or a single bond, and q is an integer of from 0 to 3. Alternatively, two of the substituents on adjacent atoms of the aryl or heteroaryl ring may optionally be replaced with a substituent of the formula -A (CH$_2$)rB—, wherein A and B are independently selected from —CRR'—, —O—, —NR—, —S—, —S(O)—, S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')s-X—(CR"R''')d-, where s and d are independently selected from integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C1-C6)alkyl respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C1-C4)alkyl" is mean to include, but not be limited to, trifluoromethyl, 2,2,2-trifluoroethyl, 4-chlorobutyl, 3-bromopropyl, and the like.

Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. C1-6 alkoxy, is intended to include C1, C2, C3, C4, C5, and C6 alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. 3-7 cycloalkyl is intended to include C3, C4, C5, C6, and C7 cycloalkyl groups. "Alkenyl" is intended to include hydrocarbon chains of either straight or branched configuration and one or more carbon-carbon double bonds that may occur in any stable point along the chain, such as ethenyl and propenyl.

The term "Halo" or "halogen" as used herein refers to fluoro, chloro, bromo, and iodo.

As used herein, the term "hetero", mean, unless otherwise stated, "heteroatom" or "heteroradical" (namely radical containing heteroatom), including atoms other than carbon (C) and hydrogen (H), also including the radicals containing these heteroatoms. Examples include oxygen (O), nitrogen (N), sulfur (S), silicon (Si), germanium (Ge), aluminum (Al), boron (B), —O—, —S—, =O—, =S, —C(=O)O—, —C(=O)—, —C(=S)—, —S(=O)—, —S(=O)$_2$—, also include optionally substituted —C(=O)N(H)—, —N(H)—, —C(=NH)—, —S(=O)$_2$N(H)—, or —S(=O) N(H)—.

"Ring" as used herein, means a substituted or unsubstituted cycloalkyl, heterocycloalkyl, cycloalkenyl, heterocycloalkenyl, cycloalkynyl, heterocycloalkynyl, aryl, or heteroaryl. A ring includes mono, bi, sprio, fused, and bridged ring moieties. The number of atoms in a ring is typically defined by the number of members in the ring. For example, a "5- to 7-membered ring" means there are 5 to 7 atoms in the encircling arrangement. Unless otherwise specified, the ring optionally includes one to three heteroatoms. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heterocycle" or "heterocyclic group" is intended to mean a stable monocyclic, bicyclic, or tricyclic ring containing heteroatom or heteroradical, which is saturated, partially unsaturated or unsaturated (aromatic), and which consists of carbon atoms and 1, 2, 3, or 4 ring heteroatoms independently selected from N, O and S and including any bicyclic group in which any of the above-defined heterocyclic rings is fused to a benzene ring. The nitrogen and sulfur heteroatoms may optionally be oxidized (i. e., NO and S(O)p). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heterotams independently selected from N, O and S. The nitrogen atom may be substituted or unsubstituted (i.e., N or NR wherein R is H or another substituent, if defined). The nitrogen and sulfur heteroatoms may optionally be oxidized (i.e., NO and S(O)p). It is noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thienyl, thienothiazolyl, thienooxazolyl, thienoimidazolyl, triazinyl, 1,2,3-triazolyl, 1,2,4-triazolyl, 1,2,5-triazolyl, 1,3,4-triazolyl, and xanthenyl. Also included are fused ring and spiro compounds.

The term "hydrocarbyl" or its lower concept (such as alkyl, alkenyl, alkynyl and phenyl etc.) by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). "Hydrocarbyl" include, but are not limited to, aliphatic hydrocarbyl and aromatic hydrocarbyl, and the aliphatic hydrocarbyl include linear and cyclic ones, specifically including but not limited to, alkyl, alkenyl, and alkynyl, and the aromatic hydrocarbyl include, but are not limited to, 6-12 membered aromatichydrocarbyl, for example, benzene, and naphthalene. In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "heterohydrocarbyl" or its lower concept (such as heteroalkyl, heteroalkenyl, teteroalkynyl and heteroaryl etc.) by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from B, O, N and S, and wherein the nitrogen and sulfur atoms may optionally be oxidized and the nitrogen heteroatom may optionally be quaternized. The heteroatom(s) B, O, N and S may be placed at any interior position of the heterohydrocarbyl group (including the position at which the hydrocarbyl group is attached to the remainder of the molecule). Examples include, but are not limited to, —CH2-CH2-O—CH3, —CH2-CH2-NH—CH3, —CH2-CH2-N(CH3)-CH3, —CH2-S—CH2-CH3, —CH2-CH2-S(O)—CH3, —CH2-CH2-S(O)2-CH3, —CH=CH—O—CH3, —CH2-CH=N—OCH3, and —CH=CH—N(CH3)-CH3. Up to two heteroatoms may be consecutive, such as —CH$_2$—NH—OCH$_3$.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "cyclohydrocarbyl", "heterocyclohydrocarbyl", or their lower concepts (such as aryl, heteroaryl, cycloalkyl, heterocycloalkyl, cycloalkenyl, heterocycloalkenyl, cycloalkynyl, and heterocycloalkynyl etc.) by themselves or in combination with other terms, represent, unless otherwise stated, cyclic versions of "hydrocarbyl" or "heterohydrocarbyl", respectively. Additionally, for heterohydrocarbyl or heterocyclohydrocarbyl(such as heteroalkyl and heterocycloalkyl), a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Non-limiting examples of heterocycloalkyl moieties include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthio, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "leaving group" means a functional group or atom which can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, p-tosylate and the like; and acyloxy groups, such as acetoxy, trifluoroacetoxy and the like.

The term "protecting group" includes but not limited to "amino-protecting group", "hydroxy-protecting group" and "thiol-protecting group". The term "amino-protecting group" means a protecting group suitable for preventing undesired reactions at an amino nitrogen. Representative amino-protecting groups include, but are not limited to, formyl; acyl groups, for example alkanoyl groups, such as acetyl, trichloroacetyl or trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl) methyl; silyl groups, such as trimethylsilyl (TMS) and tert-butyldimethylsilyl (TBS); and the like. The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butyldimethylsilyl (TBS); and the like.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below.

All solvents used are commercially available and are used without further purification. Reactions are typically run using anhydrous solvents under an inert atmosphere of nitrogen. Proton NMR are recorded on Bruker Avance III 400 (400 MHz) spectrometer and chemical shifts are reported as (ppm) down field from tetramethylsilane. Mass spectra are determined on Agilent 1200 series plus 6110 (& 1956A). LC/MS, or Shimadzu MS consisting of a DAD: SPD-M20A (LC) and Shimadzu Micromass 2020 detector. The mass spectrometer is equipped with an electrospray ion source (ESI) operated in a positive or negative mode.

The following abbreviations are used: aq is aqueous; HATU is O-(7-azabenzotriazol-1-yl)-N,N,N',N'-tetramethyluronium hexafluorophosphate; EDC is N-(3-dimethylaminopropyl)-N'-ethylcarbodiimide hydrochloride, m-CPBA is 3-chloroperoxybenzoic acid; equivalent is eq.; CDI is carbonyl diimidaole; DCM is dichloromethane; PE is petroleum ether; DIAD is diisopropyl azodicarboxylate; DMF is N,N-dimethylformamide; DMSO is dimethylsulfoxide; EtOAc is ethyl acetate; EtOH is ethanol; MeOH is methanol; CBz is benzyloxycarbonyl, a amine protecting group; BOC is tert-butylcarbonyl, amine protecting group; HOAc is acetic acid; NaCNBH$_3$ is sodium cyanoborohydride; r.t. is room temperature; O/N is overnight; THF is tetrahydrofuran; Boc$_2$O is di-tert-butyl dicarbonate; TFA is trifluoroacetic acid; DIPEA is diisopropylethylamine; SOCl$_2$ is sulfurous dichloride; CS$_2$ is carbon disulfide; TsOH is 4-methylbenzenesulfonic acid; NFSI is N-fluoro-N-(phenylsulfonyl)benzenesulfonamide; NCS is 1-chloropyrrolidine-2,5-dione; n-Bu$_4$NF is tetrabutylammonium fluoride; i-PrOH is 2-propanol and mp is melting point.

Compounds are named either manually or by using ChemDraw®, or using vendors catalogue name if commercially available.

HPLC analyses are performed on a Shimadzu LC20AB system with a Shimadzu SIL-20A Autosampler and a Shimadzu DAD:SPD-M20A Detector. The column used is a Xtimate C18, 3 μm, 2.1×300 mm. Method 0-60AB_6 min: A linear gradient is applied, starting at 100% A (A: 0.0675% TFA in water) and ending at 60% B (B: 0.0625% TFA in MeCN) over 4.2 min and then maintained at 60% B until the 1.0 min mark. The column is then re-equilibrated over 0.8 min to 100:0 with a total run time of 6 min. Method 10-80AB_6 min: A linear gradient is applied, starting at 90% A (A: 0.0675% TFA in water) and ending at 80% B (B: 0.0625% TFA in MeCN) over 4.2 min and then maintained at 80% B until the 1.0 min mark. The column is then re-equilibrated over 0.8 min to 90:10 with a total run time of 6 min. The column temperature is at 50° C. with the flow rate of 0.8 mL/min. The Diode Array Detector is scanned from 200-400 nm.

Thin layer chromatography (TLC) is performed on Silica gel GF254 from Sanpont-group and UV is typically used to visualize the spots. Additional visualization methods are also employed in some cases. In these cases the TLC plate is developed with iodine (generated by adding approximately 1 g of I$_2$ to 10 g silica gel and thoroughly mixing), vanillin (generated by dissolving about 1 g vanillin in 100 mL 10% H$_2$SO$_4$), ninhydrin (available commercially from Aldrich), or Magic Stain (generated by thoroughly mixing 25 g (NH$_4$)$_6$Mo$_7$O$_{24}$.4H$_2$O, 5 g (NH$_4$)$_2$Ce(IV)(NO$_3$)$_6$, 450 mL H$_2$O and 50 mL concentrated H$_2$SO$_4$) to visualize the compound. Flash chromatography is performed using 40-63 μm (230-400 mesh) silica gel from Silicycle following analogous techniques to those disclosed in Still, W. C.; Kahn, M.; and Mitra, M. Journal of Organic Chemistry, 1978, 43, 2923-2925. Typical solvents used for flash chromatography or thin layer chromatography are mixtures of dichloromethane/methanol, ethyl acetate/methanol and hexanes/ethyl acetate.

Preparative chromatography is performed on a Gilson-281 Prep LC 322 System using a Gilson UV/VIS-156 Detector. The column used is a Agella Venusil ASB Prep C18, 5 μm, 150×21.2 mm or Phenomenex Gemini C18, 5 μm, 150×30 mm or Boston Symmetrix C18, 5 μm, 150×30 mm or Phenomenex Synergi C18, 4 μm, 150×30 mm. Narrow gradients with acetonitrile/water, with the water containing 0.05% HCl or 0.25% HCOOH or 0.5% NH$_3$.H$_2$O, are used to elute the compound at a flow rate of approximately 25 mL/min and a total run time between 8-15 min.

SFC analyses are performed on an Agilent 1260 Infinity SFC system with an Agilent 1260 Autosampler and an Agilent DAD:1260 Detector. The column used is Chiralcel OD-H 250×4.6 mm I.D., 5 um or Chiralpak AS-H 250×4.6 mm I.D., 5 μm or Chiralpak AD-H 250×4.6 mm I.D., 5 um. Method OD-H_5_40_2.35 ML Column: Chiralcel OD-H 250×4.6 mm I.D., 5 μm, Mobile phase: 40% ethanol (0.05% DEA) in CO$_2$ Flow rate: 2.35 mL/min Wavelength: 220 nm. Method AS-H_3_40_2.35 ML Column: Chiralpak AS-H 250×4.6 mm I.D., 5 μm, Mobile phase: 40% methanol (0.05% DEA) in CO$_2$ Flow rate: 2.35 mL/min Wavelength: 220 nm. Method OD-H_3_40_2.35M Column: Chiralcel OD-H 250×4.6 mm I.D., 5 μm, Mobile phase: 40% methanol (0.05% DEA) in CO$_2$ Flow rate: 2.35 mL/min Wavelength: 220 nm. Method AD-H_2_50_2.35 ML Column: Chiralpak AD-H 250×4.6 mm I.D., 5 μm, Mobile phase: 50% methanol (0.1% MEA) in CO$_2$ Flow rate: 2.35 mL/min Wavelength: 220 nm.

Preparative SFC is performed on a Waters Thar 80 Pre-SFC System using a Gilson UV Detector. The column used is Chiralcel OD-H 250×4.6 mm I.D., 5 m or Chiralpak AD-H 250×4.6 mm I.D., 5 μm. Narrow gradients with ethanol or methanol in CO$_2$, with the ethanol or methanol containing 0.05% NH$_3$.H$_2$O or 0.05% DEA or 0.1% MEA, are used to elute the compound at a flow rate between 40-80 mL/min and a total run time between 20-30 min.

Process for Preparing the Compound of the Present Invention

The compound of the present invention can be prepared in a number of ways known to one skilled in the art of organic synthesis. The compound of the present invention can be synthesized using the methods described below, together with synthetic methods known in the art of synthetic organic chemistry, or by variations thereon as appreciated by those skilled in the art. Preferred methods include, but are not limited to, those described below.

The reactions are performed in a solvent appropriate to the reagents and materials employed and suitable for the transformations being effected. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups, such as amino group, present in the compound described in this invention. An authoritative account describing the many alternatives to the trained practitioner is Greene and Wuts (Protective Groups In Organic Synthesis, Wiley and Sons, 1991). All references cited herein are hereby incorporated in their entirety herein by reference.

The compound of the present invention of formula (IV), could be prepared as outlined in Scheme 1 and via standard methods known to those skilled in the art. Piperidin-2-one (1-1) for example, is reacted with POCl$_5$ in organic solvent, such as CHCl$_3$ to be dichlorinated in the ortho position, the resulting dichlorinated product is replaced by two morpholine molecule and then one of them is eliminated to form a double bond. The resulting product is reacted with an aromatic ring-halogenated acetyl hydrazide group by 3+2 cycloaddition and followed by eliminate the morpholine group under acidic conditions to form pyrazolopyridine ring system. The pyrazolopyridin product is introduced pyridyl group in palladium-catalyzed reactions using Bulkwald C—N coupling reaction. The pyridine group is reduced to piperidinyl group by catalytic hydrogenation using foil dioxide as the catalyst, then the amino group on the piperidyl group is introduced a nitroso group by oxidization of NaNO$_2$. After the reduction of zinc to give a hydrazine compound, it is reacted with a halogenated alkyl carboxylate through amide condensation reaction, then NaH is handled to form a six-membered lactam ring. At last, the reaction of ammonia urethane exchange reaction is used to give the form amide functional group (1-6), which is the factor Xa inhibitor of the current invention.

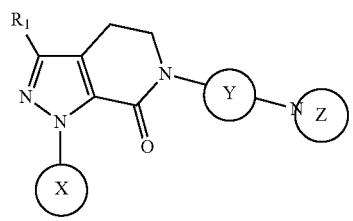

(IV)

Scheme 1

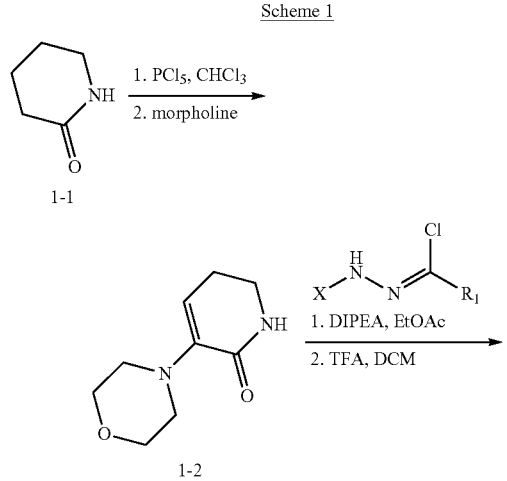

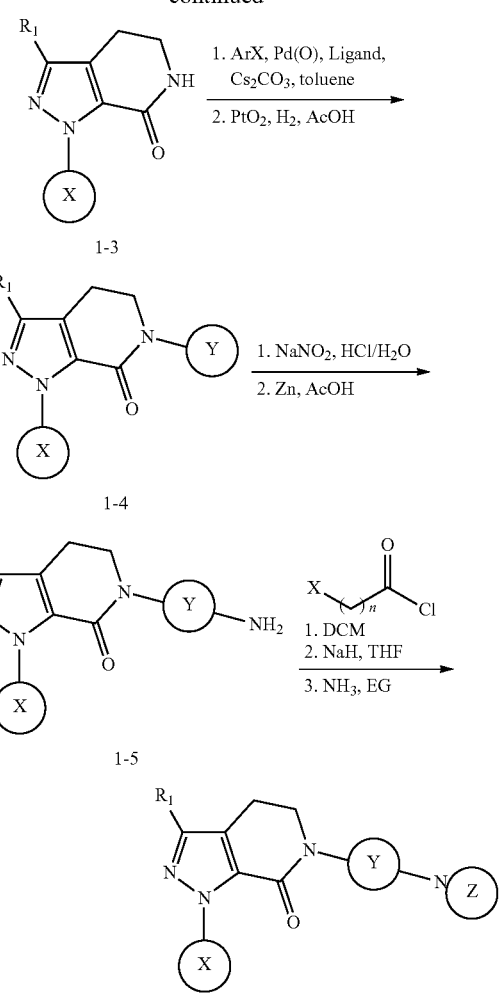

To be specific, the compound of the present invention of formula IV (Scheme 1) could be prepared as outlined in Scheme 1 or by other standard methods known to those skilled in the art. Starting from commercially available piperidin-2-one (1-1) derivatives, or other similar derivatives modified by other different functional group, such as piperidin-2-one N-alkylated intermediates, compound (1-3) R ring may be formamide, carboxylate ethyl, cyano, trifluoromethyl, and etcs. X, Y, Z is selected from various aromatic or saturated carbocyclic or heterocyclic ring. All these variations, replacement are illustrated in the detailed exemplary section. The sequence of reactions shown in Scheme 1 can be different to prepare the compound of this invention, which is known to the man skilled in the art, which also within the scope and spirit of this invention.

As a consequence, the current invention discloses a series of novel hydrazide compound of formula (I), as a selective and potent inhibitors of factor Xa and thus are useful as anticoagulants. Representative compound of present invention, of formula (I) has shown improved higher solubility and efficacy and less bleeding tendency in animal models as compared to apixaban standard. Therefore, the compound of formula (I) can be valuable therapeutic agents for the treatment and prevention of thromboembolic disorders.

EMBODIMENTS

To describe the present invention in more detail, the following examples are provided. However, the scope of the present invention is not limited to these.

Example 1

4-(4-(1-(4-Methoxyphenyl)-7-oxo-3-(trifluoromethyl)-4,5-dihydro-1H-pyrazolo[3,4-c]pyridin-6(7H)-yl)piperidin-1-yl)morpholin-3-one

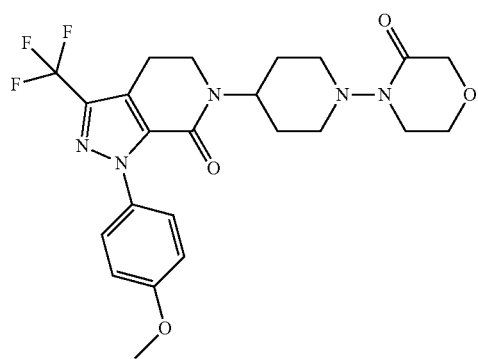 [SMILES: COc1ccc(-n2nc(C(F)(F)F)c3c2C(=O)N(C2CCN(N4CCOCC4=O)CC2)CC3)cc1]

Scheme for the Preparation:

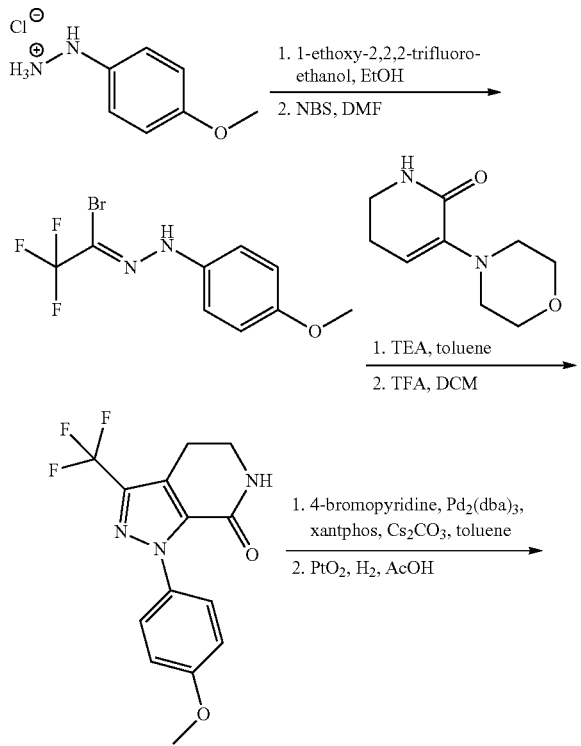

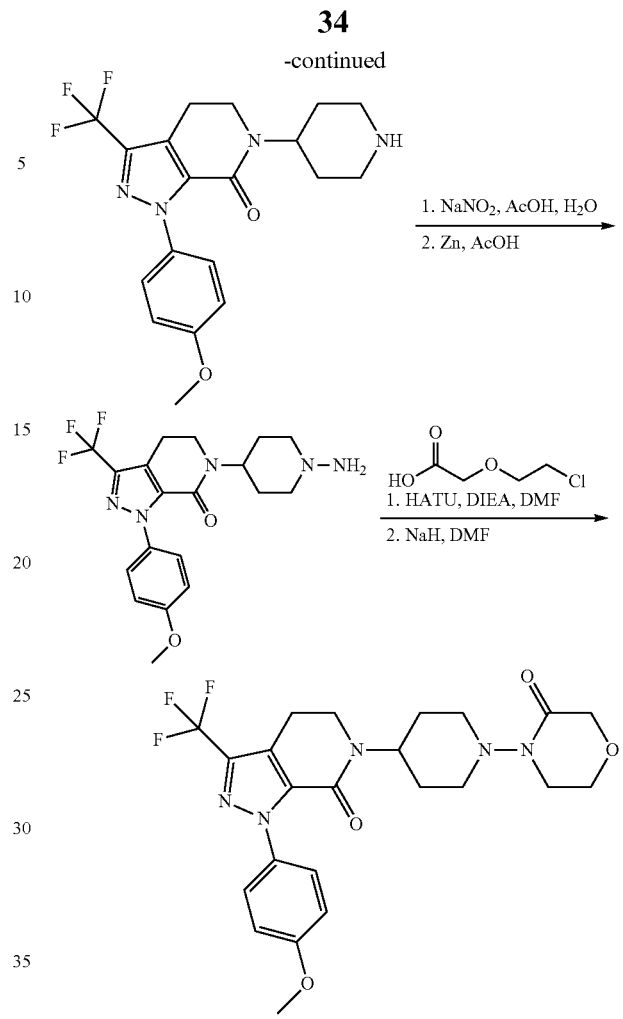

Step A: (4-Methoxyphenyl)hydrazine hydrochloride (4.83 g, 27.7 mmol) was dissolved in ethanol (50 mL), 1-ethoxy-2,2,2-trifluoroethanol (4.8 g, 33.3 mmol) was added and the mixture was refluxed for 16 hours. The reaction mixture was concentrated, then the residue was dissolved in DMF (50 mL) and cooled to 0° C. NBS (6.1 g, 27.7 mmol) was added slowly to the solution. The reaction mixture was warmed to 25° C. and stirred for 16 hours. The reaction mixture was quenched with water, extracted with ethyl acetate. The combined organics were washed with brine, dried over anhydrous $Na_2SO_4$, filtered and concentrated. The crude residue is purified by silica gel chromatography (PE to PE:EA=20:1) to give (Z)-2,2,2-trifluoro-N'-(4-methoxyphenyl)acetohydrazonoyl bromide (3.3 g, 39%) as a yellow oil. LCMS (ESI) m/z: 296.0 (M+23).

Step B: To a solution of (Z)-2,2,2-trifluoro-N'-(4-methoxyphenyl) acetohydrazonoyl bromide (3.3 g, 11.1 mmol) in toluene (35 mL) was added 3-morpholino-5,6-dihydropyridin-2(1H)-one (2.43 g, 13.3 mmol) and TEA (2.25 g, 22.2 mmol). The mixture was heated to reflux for 16 hours. The mixture was poured into water (80 mL), extracted with EA (80 mL×2), washed with brine, dried over anhydrous $Na_2SO_4$, filtered and concentrated. The crude residue is purified by silica gel chromatography (PE to PE:EA=5:1 to 1:1) to give 1-(4-methoxyphenyl)-7a-morpholino-3-(trifluoromethyl)-3a,4,5,6-tetrahydro-1H-pyrazolo[3,4-c]pyridin-7(7aH)-one (1.38 g, 30%) as a yellow solid. LCMS (ESI) m/z: 421.1 (M+23).

Step C: To a solution of 1-(4-methoxyphenyl)-7a-morpholino-3-(trifluoromethyl)-3a,4,5,6-tetrahydro-1H-pyrazolo[3,4-c]pyridin-7(7aH)-one (1.38 g, 3.46 mmol) in DCM (15 mL) was added TFA (1.5 mL). The mixture was stirred at 25° C. for 2 hours, poured into water (50 mL), and extracted with DCM (50 mL×2). The combined organics was washed with brine, dried over anhydrous $Na_2SO_4$, concentrated to give 1-(4-methoxyphenyl)-3-(trifluoromethyl)-5,6-dihydro-1H-pyrazolo[3,4-c]pyridin-7(4H)-one (1.08 g, crude) as a yellow solid. LCMS (ESI) m/z: 312.2 (M+1).

Step D: A mixture of 1-(4-methoxyphenyl)-3-(trifluoromethyl)-5,6-dihydro-1H-pyrazolo[3,4-c]pyridin-7(4H)-one (1.08 g, 3.47 mmol), 4-bromopyridine hydrochloride (1.01 g, 5.2 mmol), $Pd_2(dba)_3$ (318 mg, 8.67 mmol), Xantphos (200 mg, 0.347 mmol), and $Cs_2CO_3$ (2.83 g, 8.67 mmol) in toluene (15 mL) was heated to 80° C. for 16 hours. The mixture was cooled to room temperature, filtered. The filtrate was concentrated and the crude residue was purified by silica gel chromatography (PE:EA=10:1 to 1:1) to give 1-(4-methoxyphenyl)-6-(pyridin-4-yl)-3-(trifluoromethyl)-5,6-dihydro-1H-pyrazolo[3,4-c]pyridin-7(4H)-one (800 mg, 59%) as a yellow solid. LCMS (ESI) m/z: 389.1 (M+1).

Step E: A mixture of 1-(4-methoxyphenyl)-6-(pyridin-4-yl)-3-(trifluoromethyl)-5,6-dihydro-1H-pyrazolo[3,4-c]pyridin-7(4H)-one (800 mg, 2.06 mmol) and $PtO_2$ (50 mg) in AcOH (10 mL) was stirred under 50 psi of $H_2$ at 25° C. for 16 hours. The mixture was filter, and the filtrate was concentrated to give 1-(4-methoxyphenyl)-6-(piperidin-4-yl)-3-(trifluoromethyl)-5,6-dihydro-1H-pyrazolo[3,4-c]pyridin-7(4H)-one (900 mg, crude) as a yellow oil, which was used in the next step directly. LCMS (ESI) m/z: 395.2 (M+1).

Step F: To a solution of 1-(4-methoxyphenyl)-6-(piperidin-4-yl)-3-(trifluoromethyl)-5,6-dihydro-1H-pyrazolo[3,4-c]pyridin-7(4H)-one (900 mg crude, 2.06 mmol) in AcOH (8 mL) was added $NaNO_2$ (711 mg, 10.3 mmol, in 4 mL of water) solution at 0° C. The mixture was warmed and stirred at 25° C. for 16 hours. The mixture was poured into water (30 mL), extracted with DCM (30 mL×2). The combined organics was dried over anhydrous $Na_2SO_4$, concentrated to give 1-(4-methoxyphenyl)-6-(1-nitrosopiperidin-4-yl)-3-(trifluoromethyl)-5,6-dihydro-1H-pyrazolo[3,4-c]pyridin-7(4H)-one (900 mg, crude) as a yellow solid. LCMS (ESI) m/z: 424.2 (M+1).

Step G: To a solution of 1-(4-methoxyphenyl)-6-(1-nitrosopiperidin-4-yl)-3-(trifluoromethyl)-5,6-dihydro-1H-pyrazolo[3,4-c]pyridin-7(4H)-one (900 mg crude, 2.06 mmol) in AcOH (10 mL) was added Zn powder (670 mg, 10.3 mmol). The mixture was stirred at 25° C. for 3 hours. The mixture was filtered, the filtrate was concentrated, and little AcOH was removed by freeze-drying. The crude residue 6-(1-aminopiperidin-4-yl)-1-(4-methoxyphenyl)-3-(trifluoromethyl)-5,6-dihydro-1H-pyrazolo[3,4-c]pyridin-7(4H)-one (900 mg crude, 2.06 mmol) was used directly in next step. LCMS (ESI) m/z: 410.2 (M+1).

Step H: To a solution of 2-(2-chloroethoxy)acetic acid (342 mg 2.47 mmol) in DMF (10 mL) was added HATU (939 mg, 2.47 mmol), DIEA (532 mg, 4.12 mmol), and then 6-(1-aminopiperidin-4-yl)-1-(4-methoxyphenyl)-3-(trifluoromethyl)-5,6-dihydro-1H-pyrazolo[3,4-c]pyridin-7(4H)-one (900 mg crude, 2.06 mmol). The mixture was stirred at 25° C. for 16 hours. The mixture was poured into water (80 mL), extracted with EA (60 mL×2). The combined organics were dried over anhydrous $Na_2SO_4$, concentrated. The crude residue was purified by silical gel chromatography (PE:EA=1:1 to EA) to give 2-(2-chloroethoxy)-N-(4-(1-(4-methoxyphenyl)-7-oxo-3-(trifluoromethyl)-4,5-dihydro-1H-pyrazolo[3,4-c]pyridin-6(7H)-yl)piperidin-1-yl)acetamide (900 mg, 82%) as a yellow solid. LCMS (ESI) m/z: 530.2 (M+1).

Step I: To a solution of 2-(2-chloroethoxy)-N-(4-(1-(4-methoxyphenyl)-7-oxo-3-(trifluoromethyl)-4,5-dihydro-1H-pyrazolo[3,4-c]pyridin-6(7H)-yl)piperidin-1-yl)acetamide (900 mg, 1.7 mmol) in DMF (10 mL) was added NaH (74.8 mg, 1.87 mmol) at 0° C. The mixture was stirred at 25° C. for 2 hours. The mixture was poured into water (80 mL), extracted with EA (80 mL), dried over anhydrous $Na_2SO_4$ and concentrated. The crude residue was purified by preparative HPLC (FA) to give 4-(4-(1-(4-methoxyphenyl)-7-oxo-3-(trifluoromethyl)-4,5-dihydro-1H-pyrazolo[3,4-c]pyridin-6(7H)-yl)piperidin-1-yl)morpholin-3-one (303 mg, 36%) as a white solid. $^1$H NMR (400 MHz, DMSO-$d_6$) δ 7.45 (m, 2H), 7.02 (m, 2H), 4.24 (m, 1H), 3.97 (s, 2H), 3.82-3.78 (m, 5H), 3.60 (t, J=6.4 Hz, 2H), 3.42-3.39 (m, 4H), 3.02-2.99 (m, 2H), 2.90-2.88 (m, 2H), 1.82-1.77 (m, 2H), 1.59-1.56 (m, 2H). LCMS (ESI) m/z: 494.2 (M+1).

Example 2

1-(4-Methoxyphenyl)-6-(2'-oxo-[1,1'-bipiperidin]-4-yl)-3-(trifluoromethyl)-5,6-dihydro-1H-pyrazolo[3,4-c]pyridin-7(4H)-one

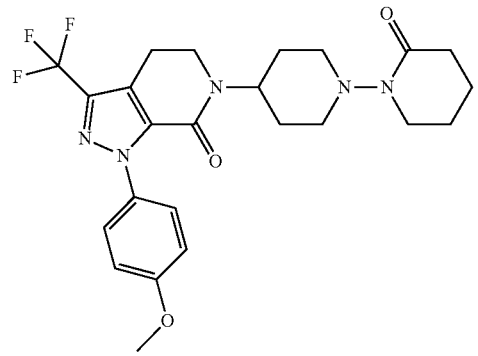 [SMILES: COc1ccc(-n2nc(C(F)(F)F)c3c2C(=O)N(C2CCN(N4CCCCC4=O)CC2)CC3)cc1]

Step A: To a solution of 6-(1-aminopiperidin-4-yl)-1-(4-methoxyphenyl)-3-(trifluoromethyl)-5,6-dihydro-1H-pyrazolo[3,4-c]pyridin-7(4H)-one (500 mg, 1.22 mmol) in DMF (8 mL) was added DIEA (315 mg, 2.44 mmol) and 5-bromopentanoyl chloride (267 mg, 1.34 mmol). The mixture was shirred at 25° C. for 3 hours. The mixture was poured into water (30 mL), extracted with EA (30 mL×2), dried over anhydrous $Na_2SO_4$, filtered, and concentrated. The crude residue was purified by TLC (EA) to give 5-bromo-N-(4-(1-(4-methoxyphenyl)-7-oxo-3-(trifluoromethyl)-4,5-dihydro-1H-pyrazolo[3,4-c]pyridin-6(7H)-yl)piperidin-1-yl)pentanamide (180 mg, 25%) as a yellow solid. LCMS (ESI) m/z: 528.2 (M+1), 530.2 (M+3).

Step B: To a solution of 5-bromo-N-(4-(1-(4-methoxyphenyl)-7-oxo-3-(trifluoromethyl)-4,5-dihydro-1H-pyrazolo[3,4-c]pyridin-6(7H)-yl)piperidin-1-yl)pentanamide (180 mg, 0.315 mmol) in DMF (3 mL) was added NaH (14 mg, 0.346 mmol) at 0° C. The mixture was stirred at 25° C.

for 3 hours. The mixture was poured into water (30 mL), extracted with EtOAc (30 mL×2), dried over anhydrous Na₂SO₄ and concentrated. The crude residue was purified by preparative HPLC (FA) to give 1-(4-methoxyphenyl)-6-(2'-oxo-[1,1'-bipiperidin]-4-yl)-3-(trifluoromethyl)-5,6-dihydro-1H-pyrazolo[3,4-c]pyridin-7(4H)-one (32 mg, 20%) as a white solid. ¹H NMR (400 MHz, DMSO-d₆) δ 7.46-7.44 (m, 2H), 7.03-7.01 (m, 2H), 4.23-4.21 (m, 1H), 3.82 (s, 3H), 3.61-3.57 (m, 4H), 3.31-3.29 (m, 2H), 2.88-2.67 (m, 4H), 2.32-2.16 (m, 2H), 1.74-1.71 (m, 4H), 1.59-1.56 (m, 4H). LCMS (ESI) m/z: 492.2 (M+1).

Example 3

1-(4-Methoxyphenyl)-6-(1-(2-oxopyrrolidin-1-yl)piperidin-4-yl)-3-(trifluoromethyl)-5,6-dihydro-1H-pyrazolo[3,4-c]pyridin-7(4H)-one

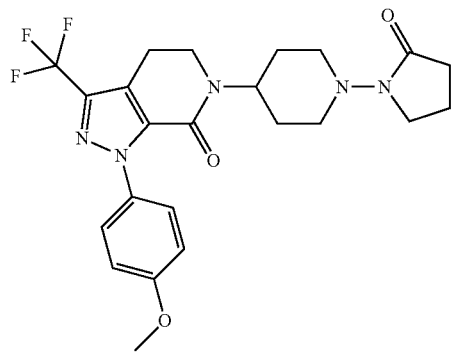 [SMILES: COc1ccc(-n2nc(C(F)(F)F)c3c2C(=O)N(C2CCN(N4CCCC4=O)CC2)CC3)cc1]

Step A: To a solution of 6-(1-aminopiperidin-4-yl)-1-(4-methoxyphenyl)-3-(trifluoromethyl)-5,6-dihydro-1H-pyrazolo[3,4-c]pyridin-7(4H)-one (250 mg, 0.611 mmol) in DCM (8 mL) was added Et₃N (62 mg, 0.611 mmol) and 4-chlorobutanoyl chloride (86 mg, 0.611 mmol). The mixture was stirred at 25° C. for 16 hours. The resulting mixture was poured into water (30 mL), extracted with DCM (30 mL×2), dried over anhydrous Na₂SO₄, concentrated, the crude was purified by TLC (EA) to give 4-chloro-N-(4-(1-(4-methoxyphenyl)-7-oxo-3-(trifluoromethyl)-4,5-dihydro-1H-pyrazolo[3,4-c]pyridin-6(7H)-yl)piperidin-1-yl)butanamide (100 mg, 32%) as a yellow solid. LCMS (ESI) m/z: 514.2 (M+1), 516.2 (M+3).

Step B: To a solution of 4-chloro-N-(4-(1-(4-methoxyphenyl)-7-oxo-3-(trifluoromethyl)-4,5-dihydro-1H-pyrazolo[3,4-c]pyridin-6(7H)-yl)piperidin-1-yl)butanamide (180 mg, 0.351 mmol) in DMF (3 mL) was added NaH (15.4 mg, 0.385 mmol) at 0° C. The mixture was stirred at 25° C. C for 16 hours. The mixture was poured into water (30 mL), extracted EA (30 mL×2), dried over anhydrous Na₂SO₄, and concentrated. The crude residue was purified by preparative HPLC (FA) to give 1-(4-methoxyphenyl)-6-(1-(2-oxopyrrolidin-1-yl)piperidin-4-yl)-3-(trifluoromethyl)-5,6-dihydro-1H-pyrazolo[3,4-c]pyridin-7(4H)-one (39 mg, 23%) as a white solid. ¹H NMR (400 MHz, DMSO-d₆) δ 7.46-7.43 (m, 2H), 7.03-7.00 (m, 2H), 4.27-4.21 (m, 1H), 3.81 (s, 3H), 3.59 (t, J=6.8 Hz, 2H), 3.36 (t, J=6.8 Hz, 2H), 3.05-3.03 (m, 2H), 2.90-2.86 (m, 4H), 2.15-2.11 (m, 2H), 1.88-1.84 (m, 4H), 1.58-1.54 (m, 2H). LCMS (ESI) m/z: 478.2 (M+1).

Example 4

1-(4-Methoxyphenyl)-7-oxo-6-(2'-oxo-[1,1'-bipiperidin]-4-yl)-4,5,6,7-tetrahydro-1H-pyrazolo[3,4-c]pyridine-3-carboxamide

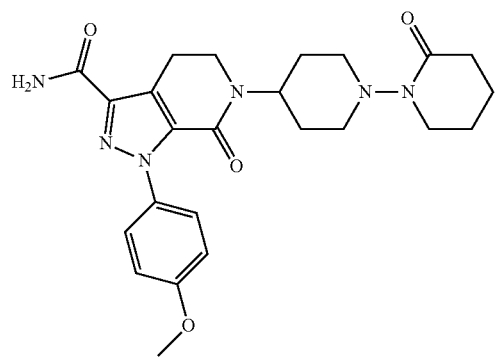 [SMILES: COc1ccc(-n2nc(C(N)=O)c3c2C(=O)N(C2CCN(N4CCCCC4=O)CC2)CC3)cc1]

Scheme for the Preparation:

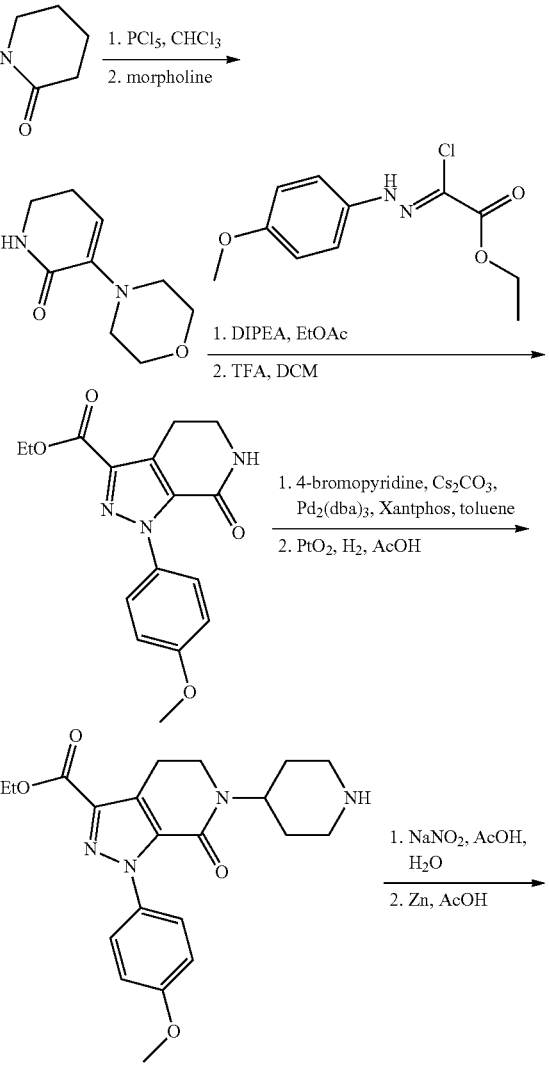

-continued

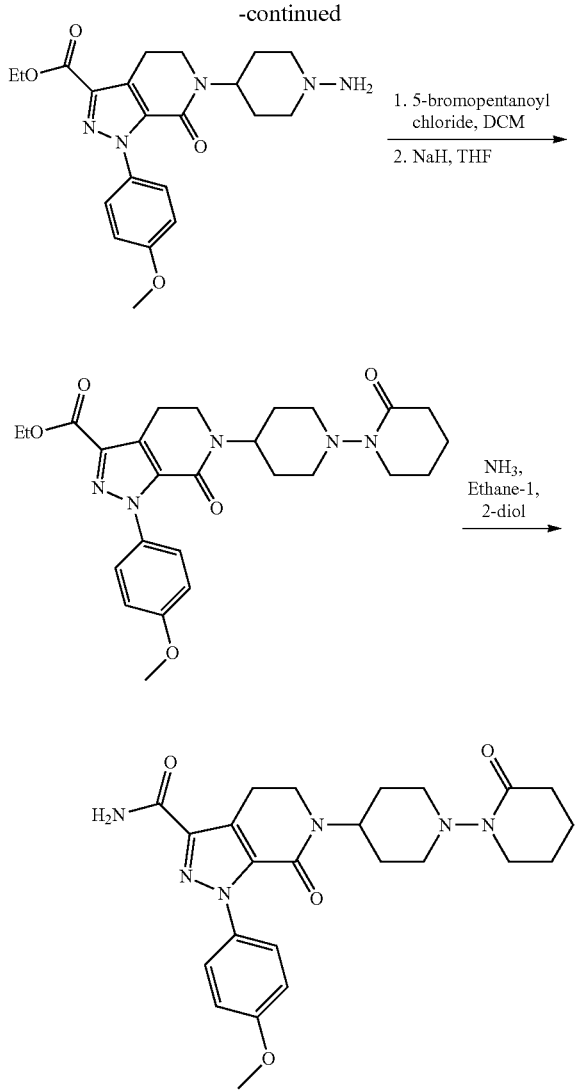

Step A: To a solution of piperidin-2-one (30.0 g, 0.3 mol) in chloroform (1 L) was added $PCl_5$ (246.0 g, 1.2 mol). The mixture was refluxed for 5 hours. After cooled to room temperature, the reaction mixture was poured into ice water slowly, extracted with dichloromethane twice. The combined organics were dried over anhydrous $Na_2SO_4$, concentrated to give 3,3-dichloropiperidin-2-one (31 g, crude), which was used directly in next step.

Step B: 3,3-Dichloropiperidin-2-one (31 g, crude) was dissolved in morpholine (300 mL), the mixture was heated to 130° C. overnight. The solvent was removed by concentration, and then washed with dichloromethane. The solid was filtered, the organic layer was concentrated, and the crude was purified by chromatography to give 3-morpholino-5,6-dihydropyridin-2(1H)-one (23 g). $^1$H NMR (CDCl$_3$, 400 MHz): δ=6.58-6.50 (m, 1H), 5.55 (t, J=4.8 Hz, 1H), 3.85-3.79 (m, 4H), 3.32 (td, J=6.8, 3.2 Hz, 2H), 2.87 (t, J=4.8 Hz, 4H), 2.35 (td, J=6.8, 4.8 Hz, 2H).

Step C: To a solution of (Z)-ethyl 2-chloro-2-(2-(4-methoxyphenyl) hydrazono)acetate (32 g, 0.126 mol) in EtOAc (300 mL) was added 3-morpholino-5,6-dihydropyridin-2(1H)-one (23 g, 0.126 mol, dissolved in EA), and triethylamine (31 g, 0.315 mol) at 0° C. The reaction mixture was warm to room temperature for 30 min before being heated to reflux overnight. After cooled to room temperature, the reaction mixture was filtered, the solid was collected, and washed with water, ethyl acetate, then dried in vacuo to give ethyl 1-(4-methoxyphenyl)-7a-morpholino-7-oxo-3a,4,5,6,7,7a-hexahydro-1H-pyrazolo[3,4-c]pyridine-3-carboxylate (40 g, crude). LCMS (ESI) m/z: 403 (M+1).

Step D: To a solution of ethyl 1-(4-methoxyphenyl)-7a-morpholino-7-oxo-3a,4,5,6,7,7a-hexahydro-1H-pyrazolo[3,4-c]pyridine-3-carboxylate (40 g, crude) in dichloromethane (400 mL) was added 2,2,2-trifluoroacetic acid (30 mL) slowly at 0° C., then the reaction mixture was stirred at 25° C. for 5 hours. The mixture was washed with saturated NaHCO$_3$ aqueous solution, and brine, dried over anhydrous Na$_2$SO$_4$, concentrated to give ethyl 1-(4-methoxyphenyl)-7-oxo-4,5,6,7-tetrahydro-1H-pyrazolo[3,4-c]pyridine-3-carboxylate as a yellow solid (20 g, 50%). $^1$H NMR (CDCl$_3$, 400 MHz) δ 7.50 (d, J=9.2 Hz, 1H), 6.95 (d, J=8.8 Hz, 1H), 5.69 (brs, 1H), 4.45 (q, J=7.2 Hz, 2H), 3.85 (s, 3H), 3.66-3.61 (m, 2H), 3.20 (t, J=6.8 Hz, 2H), 1.43 (t, J=6.8 Hz, 3H).

Step E: A mixture of ethyl 1-(4-methoxyphenyl)-7-oxo-4,5,6,7-tetrahydro-1H-pyrazolo[3,4-c]pyridine-3-carboxylate (3.00 g, 9.52 mmol), 4-bromopyridine hydrochloride (3.71 mg, 19.0 mmol), Pd$_2$(dba)$_3$ (872 mg, 0.952 mmol), Xantphos (1.10 g, 1.90 mmol) and Cs$_2$CO$_3$ (15.5 g, 14.6 mmol) in toluene (150 mL) was refluxed for 12 hours. After cooled to room temperature, the mixture was filtered. The filter residue was washed with EA (5 mL×3). The combined organics was concentrated to give crude product which was purified by silica gel chromatography (PE:EA=5:1 to PE:EA=1:4) to give ethyl 1-(4-methoxyphenyl)-7-oxo-6-(pyridin-4-yl)-4,5,6,7-tetrahydro-1H-pyrazolo[3,4-c]pyridine-3-carboxylate (3.30 mg, 88.5%) as yellow solid. LCMS (ESI) m/z: 393.4 (M+1).

Step F: To a solution of ethyl1-(4-methoxyphenyl)-7-oxo-6-(pyridin-4-yl)-4,5,6,7-tetrahydro-1H-pyrazolo[3,4-c]pyridine-3-carboxylate (3.30 g, 8.42 mmol) in AcOH (150 mL) was added PtO$_2$ (500 mg). The mixture was stirred at room temperature under 50 psi of H$_2$ for 12 hours. The mixture was filtered and concentrated to give ethyl1-(4-methoxyphenyl)-7-oxo-6-(piperidin-4-yl)-4,5,6,7-tetrahydro-1H-pyrazolo[3,4-c]pyridine-3-carboxylate (4.60 g, crude) as yellow oil. LCMS (ESI) m/z: 399.4 (M+1).

Step G: NaNO$_2$ (3.47 g, 50.3 mmol) was dissolved in H$_2$O (10 mL). The solution of NaNO$_2$ in H$_2$O was added into a solution of ethyl 1-(4-methoxyphenyl)-7-oxo-6-(piperidin-4-yl)-4,5,6,7-tetrahydro-1H-pyrazolo[3,4-c]pyridine-3-carboxylate (4.00 g, 10.1 mmol) in AcOH (80 mL) at 0° C. The reaction mixture was stirred at room temperature for 3 hours, and then diluted with water (200 mL) and extracted with DCM (40 mL×3). The combined organics were dried over anhydrous sodium sulfate and filtered. The filtrate was concentrated to give ethyl 1-(4-methoxyphenyl)-6-1-nitrosopiperidin-4-yl)-7-oxo-4,5,6,7-tetrahydro-1H-Pyrazolo[3, 4-c]pyridine-3-carboxylate (4.50 g, crude) as a white solid. LCMS (ESI) m/z: 428.4 (M+1).

Step H: Zn powder (6.54 g, 0.100 mmol) was added slowly into a solution of ethyl 1-(4-methoxyphenyl)-6-1-nitroSopiperidin-4-yl)-7-oxo-4,5,6,7-tetrahydro-1H-Pyrazolo[3, 4-c]pyridine-3-carboxylate (4.29 g, 10.0 mmol) in AcOH (150 mL). The reaction mixture was stirred at room temperature for 5 hours. Then the mixture was filtered and the filtrate was concentrated to give ethyl 6-(1-aminopiperidin-4-yl)-1-(4-methoxyphenyl)-7-oxo-4,5,6,7-tetrahydro-1H-pyrazolo[3, 4-c]pyridine-3-carboxylate (4.00 g, crude) as yellow solid. LCMS (ESI) m/z: 414.4 (M+1).

Step I: To DCM (20 mL) was added ethyl 6-(1-aminopiperidin-4-yl)-1-(4-methoxyphenyl)-7-oxo-4,5,6,7-tetrahydro-1H-pyrazolo[3, 4-c]pyridine-3-carboxylate (2.00 g, 0.484 mmol), 5-bromopentanoyl chloride (1.16 g, 5.81 mmol) and DIPEA (2.5 mL, 14.5 mmol). The mixture was stirred at room temperature for 12 hours. Then the mixture was poured into water (40 mL) and extracted with DCM (20 mL×3). The combined organic layer was dried over anhydrous sodium sulfate and filtered. The filtrate was concentrated to give ethyl 6-(1-(5-bromopentanamido)piperidin-4-yl)-1-(4-methoxyphenyl)-7-oxo-4,5,6,7-tetrahydro-1H-pyrazolo[3,4-c]pyridine-3-carboxylate (3.00 g, crude) as a yellow solid. LCMS (ESI) m/z: 576.2[M+1].

Step J: With ice bathing cooling, NaH (138 mg, 3.44 mmol) was added slowly into a solution of ethyl 6-(1-(5-bromopentanamido)piperidin-4-yl)-1-(4-methoxyphenyl)-7-oxo-4,5,6,7-tetrahydro-1H-pyrazolo[3,4-c]pyridine-3-carboxylate (1.80 g, 3.13 mmol) in THF (50 mL). The reaction mixture was stirred at room temperature for 12 hours, then remove the solvent in vacuo. The residue was poured into water (100 mL) and extracted with DCM (40 mL×4). The combined organic layers were dried over anhydrous sodium sulfate and filtered. The filtrate was concentrated to give crude product which was purified by silica gel chromatography (DCM:MeOH=100:1 to 10:1) to give ethyl 1-(4-methoxyphenyl)-7-oxo-6-(2'-oxo-[1,1'-bipiperidin]-4-yl)-4,5,6,7-tetrahydro-1H-pyrazolo[3,4-c]pyridine-3-carboxylate (1.00 g, 64%) as yellow solid. LCMS (ESI) m/z: 496.2[M+1].

Step K: To a solution of NH$_3$ (gas) in ethane-1,2-diol (20 mL) was added ethyl 1-(4-methoxyphenyl)-7-oxo-6-(2'-oxo-[1,1'-bipiperidin]-4-yl)-4,5,6,7-tetrahydro-1H-pyrazolo[3,4-c]pyridine-3-carboxylate (500 mg, 1.01 mmol). The mixture was stirred in a sealed tube at 80° C. for 3 hours. After cooled down, water (100 mL) was added into the mixture and filtered. The solid was washed with water (5 mL×3) and dried to give 1-(4-methoxyphenyl)-7-oxo-6-(2'-oxo-[1,1'-bipiperidin]-4-yl)-4,5,6,7-tetrahydro-1H-pyrazolo[3,4-c]pyridine-3-carboxamide (370 mg, 79%) as a yellow solid. $^1$HNMR (DMSO-d$_6$, 400 MHz) δ 7.66 (s, 1H), 7.46 (d, J=8.8 Hz, 2H), 7.39 (s, 1H), 7.01 (d, J=9.2 Hz, 2H), 4.26-4.20 (m, 1H), 3.82 (s, 3H), 3.55-3.52 (m, 3H), 3.31-3.30 (m, 3H), 3.00-2.92 (m, 4H), 2.20-2.17 (m, 2H), 1.75-1.72 (m, 2H), 1.60-1.56 (m, 4H). LCMS (ESI) m/z: 467.2 [M+1].

Example 5

1-(4-Methoxyphenyl)-7-oxo-6-(2'-oxo-[1,1'-bipiperidin]-4-yl)-4,5,6,7-tetrahydro-1H-pyrazolo[3,4-c]pyridine-3-carbonitrile

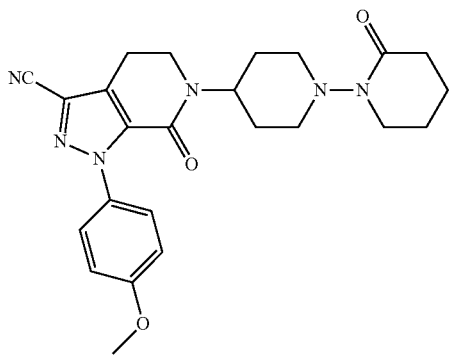 [SMILES: COc1ccc(-n2nc(C#N)c3c2C(=O)N(C2CCN(N4CCCCC4=O)CC2)CC3)cc1]

Step A: With ice bathing cooling, TFAA (406 mg, 1.93 mmol) was added dropwise into a solution of 1-(4-methoxyphenyl)-7-oxo-6-(2'-oxo-[1,1'-bipiperidin]-4-yl)-4,5,6,7-tetrahydro-1H-pyrazolo[3,4-c]pyridine-3-carboxamide (300 mg, 0.644 mmol) and Et$_3$N (0.36 mL, 2.58 mmol) in DCM (20 mL). The reaction mixture was stirred at 3° C. for 2 hours. Then pH of the mixture was adjusted to 9 with saturated NaHCO$_3$ (aq) and extracted with DCM (20 mL×2). The combined organic layers were dried over anhydrous sodium sulfate and filtered. The filtrate was concentrated to give 1-(4-methoxyphenyl)-7-oxo-6-(2'-oxo-[1,1'-bipiperidin]-4-yl)-4,5,6,7-tetrahydro-1H-pyrazolo[3,4-c]pyridine-3-carbonitril (288 mg, 99%) as white solid. $^1$HNMR (DMSO-d$_6$, 400 MHz) δ 7.49-7.46 (m, 2H), 7.05-7.02 (m, 2H), 4.26-4.16 (m, 1H), 3.83 (s, 3H), 3.60 (t, J=6.8 Hz, 2H), 3.33-3.30 (m, 4H), 2.95-2.89 (m, 4H), 2.19 (t, J=6.4 Hz, 2H), 1.83-1.69 (m, 4H), 1.61-1.53 (m, 4H). LCMS (ESI) m/z: 449.2[M+1].

Example 6

N'-Cyano-1-(4-methoxyphenyl)-7-oxo-6-(2'-oxo-[1,1'-bipiperidin]-4-yl)-4,5,6,7-tetrahydro-1H-pyrazolo[3,4-c]pyridine-3-carboximidamide

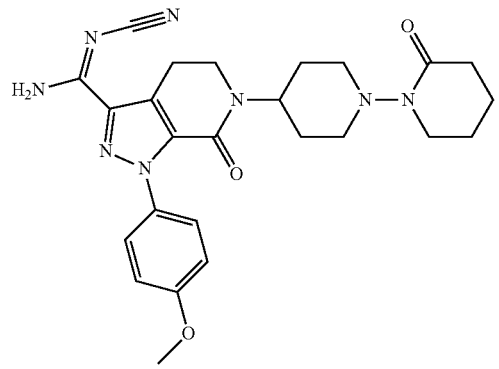 [SMILES: COc1ccc(-n2nc(/C(N)=N\C#N)c3c2C(=O)N(C2CCN(N4CCCCC4=O)CC2)CC3)cc1]

Step A: To a solution of 1-(4-methoxyphenyl)-7-oxo-6-(2'-oxo-[1,1'-bipiperidin]-4-yl)-4,5,6,7-tetrahydro-1H-pyrazolo[3,4-c]pyridine-3-carbonitrile (288 mg, 0.642 mmol) in MeOH (20 mL) was added NaOMe (69 mg, 1.28 mmol). The reaction mixture was stirred at room temperature for 3 hours before cyanamide (270 mg, 6.42 mmol) was added into the mixture. The resulting reaction mixture was stirred at room temperature for another 12 hours. The mixture was concentrated to give crude product which was purified by preparative HPLC (FA) to give N'-cyano-1-(4-methoxyphenyl)-7-oxo-6-(2'-oxo-[1,1'-bipiperidin]-4-yl)-4,5,6,7-tetrahydro-1H-pyrazolo[3,4-c]pyridine-3-carboximidamide (120 mg, 38%) as a white solid. $^1$HNMR (DMSO-d$_6$, 400 MHz) δ 8.90 (brs, 1H), 8.66 (brs, 1H), 7.52-7.49 (m, 2H), 7.04-7.01 (m, 2H), 4.26-4.20 (m, 1H), 3.83 (s, 3H), 3.54 (t, J=6.8 Hz, 3H), 3.33-3.30 (m, 3H), 3.00-2.92 (m, 4H), 2.19 (t, J=6.8 Hz, 2H), 1.81-1.69 (m, 4H), 1.62-1.53 (m, 4H). LCMS (ESI) m/z: 491.2[M+1].

Example 7

1-(4-Methoxyphenyl)-7-oxo-6-(1-(3-oxomorpholino)piperidin-4-yl)-4,5,6,7-tetrahydro-1H-pyrazolo[3,4-c]pyridine-3-carboxamide

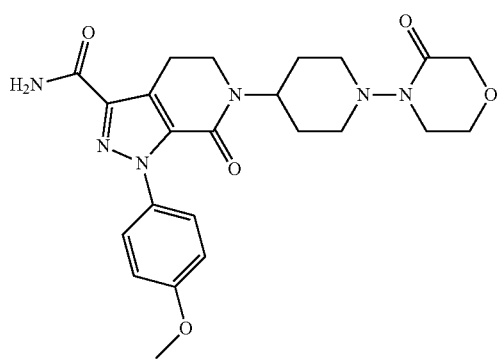 [SMILES: COc1ccc(-n2nc(C(N)=O)c3c2C(=O)N(C2CCN(N4CCOCC4=O)CC2)CC3)cc1]

Step A: To DCM (20 mL) was added ethyl 6-(1-aminopiperidin-4-yl)-1-(4-methoxyphenyl)-7-oxo-4,5,6,7-tetrahydro-1H-pyrazolo[3,4-c]pyridine-3-carboxylate (1.00 g, 2.42 mmol) and 2-(2-chloroethoxy) acetic acid (0.40 g, 2.91 mmol). DIPEA (1.2 mL, 7.2 mmol) and HATU (0.95 g, 2.5 mmol) was added into the solution. The mixture was stirred at room temperature for 12 hours. The mixture was poured into water (40 mL) and extracted with DCM (20 mL×3). The combined organic layer was dried over anhydrous sodium sulfate and filtered. The filtrate was concentrated to give ethyl 6-(1-(2-(chloromethoxy)acetamido)piperidin-4-yl)-1-(4-methoxyphenyl)-7-oxo-4,5,6,7-tetrahydro-1H-pyrazolo[3,4-c]pyridine-3-carboxylate (1.00 g, crude) as a yellow solid. LCMS (ESI) m/z: 534 (M+1).

Step B: With ice bathing cooling, NaH (100 mg, 4.16 mmol) was added dropwise into a solution of ethyl 6-(1-(2-(chloromethoxy)acetamido)piperidin-4-yl)-1-(4-methoxyphenyl)-7-oxo-4,5,6,7-tetrahydro-1H-pyrazolo[3,4-c]pyridine-3-carboxylate (0.70 g, 1.31 mmol) in THF (20 mL). The reaction mixture was stirred at room temperature for 12 hours. Then it was concentrated to remove the solvent. The residue was diluted with water (100 mL) and extracted with DCM (40 mL×4). The combined organic layer was dried with anhydrous sodium sulfate and filtered. The filtrate was concentrated to give crude product which was purified by silica gel chromatography (DCM:MeOH=100:1 to 50:1) to give ethyl 6-(1-(3-oxomorpholino)piperidin-4-yl)-1-(4-methoxyphenyl)-7-oxo-4,5,6,7-tetrahydro-1H-pyrazolo[3,4-c]pyridine-3-carboxylate (4.00 g, crude) as yellow solid. LCMS (ESI) m/z: 498 (M+1)

Step C: To a solution of NH$_3$ (gas) in ethane-1,2-diol (20 mL) was added ethyl 1-(4-methoxyphenyl)-7-oxo-6-(1-(3-oxomorpholino)piperidin-4-yl)-4,5,6,7-tetrahydro-1H-pyrazolo[3,4-c]pyridine-3-carboxylate (500 mg, 1.01 mmol). The mixture was stirred in a sealed tube at 80° C. for 3 hours. After cooled down, water (100 mL) was added into the mixture and filtered. The residue was washed with water (5 mL×3) and dried to give 1-(4-methoxyphenyl)-7-oxo-6-(1-(3-oxomorpholino)piperidin-4-yl)-4,5,6,7-tetrahydro-1H-pyrazolo[3,4-c]pyridine-3-carboxamide (370 mg, 79%) as a yellow solid. $^1$HNMR (DMSO-d$_6$, 400 MHz) δ 7.71 (s, 1H), 7.46 (d, J=8.8 Hz, 2H), 7.39 (s, 1H), 7.01 (d, J=9.2 Hz, 2H), 4.26-4.20 (m, 1H), 3.82 (s, 3H), 3.55-3.52 (m, 3H), 3.31-3.30 (m, 3H), 3.00-2.92 (m, 4H), 1.85-1.79 (m, 2H), 1.58 (d, J=10.4 Hz, 2H).

Example 8

1-(4-Methoxyphenyl)-7-oxo-6-(1-(2-oxopyrrolidin-3-yl)piperidin-4-yl)-4,5,6,7-tetrahydro-1H-pyrazolo[3,4-c]pyridine-3-carboxamide

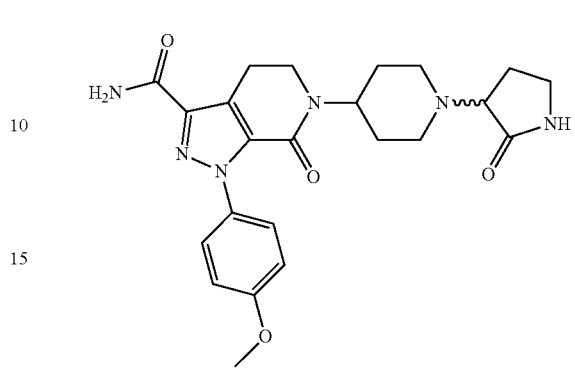

Step A: To a solution of pyrrolidin-2-one (4.32 g, 48 mmol) in DCM (120 mL) was added NEt$_3$ (24.29 g, 240 mmol), followed by added TMSCl (15.64 g, 144 mmol) at −15° C. and stirred at −15° C. for 0.5 hour. Then I$_2$ (24.36 g, 96 mmol) in DCM (180 mL) was added at −15° C., warmed to 0° C. and stirred at 0° C. for 2 hours. The resulting mixture was washed with saturated Na$_2$SO$_3$ solution (600 mL×3). The organic was dried with anhydrous sodium sulfate, filtered and concentrated. The crude residue was purified by silica gel chromatography (PE: EtOAc=1:1 to 1:3) to give 3-iodopyrrolidin-2-one (1.60 g, 16%) as a pale yellow solid.

Step B: To a solution of methyl 1-(4-methoxyphenyl)-7-oxo-6-(piperidin-4-yl)-4,5,6,7-tetrahydro-1H-pyrazolo[3,4-c]pyridine-3-carboxylate (598 mg, 1.5 mmol) in DMF (5 mL) was added NEt$_3$ (304 mg, 3.0 mmol), followed by added 3-iodopyrrolidin-2-one (317 mg, 1.5 mmol) at room temperature and stirred at room temperature for 16 hours. The reaction mixture was concentrated to give crude. The crude was purified by silica gel chromatography (DCM:MeOH=50:1 to 20:1) to give ethyl 1-(4-methoxyphenyl)-7-oxo-6-(1-(2-oxopyrrolidin-3-yl)piperidin-4-yl)-4,5,6,7-tetrahydro-1H-pyrazolo[3,4-c]pyridine-3-carboxylate (680 mg, 94%) as a pale yellow solid. LCMS (ESI) m/z: 479 (M+1).

Step C: To a sealed tube was added ethyl 1-(4-methoxyphenyl)-7-oxo-6-(1-(2-oxopyrrolidin-3-yl)piperidin-4-yl)-4,5,6,7-tetrahydro-1H-pyrazolo[3,4-c]pyridine-3-carboxylate (674 mg, 1.4 mmol) and a solution of NH$_3$ (gas) in ethane-1,2-diol (10 mL). The mixture was stirred at 120° C. for 16 hours. The mixture was cooled to room temperature and diluted with water (50 mL). The resulting mixture was extracted with EtOAc (50 mL×3). The combined organic layers were dried and concentrated. The crude residue was purified by silica gel chromatography (PE:EtOAc=1:3 to 1:1) to give 1-(4-methoxyphenyl)-7-oxo-6-(1-(2-oxopyrrolidin-3-yl)piperidin-4-yl)-4,5,6,7-tetrahydro-1H-pyrazolo[3,4-c]pyridine-3-carboxamide (400 mg, 44%) as an off-white solid. The title compound is obtained as white solid with the isomers. The isomers are further purified by preparative SFC and preparative HPLC to give two fractions, one is (18.5 mg) and the other is (23.6 mg). Fraction 1: $^1$H NMR (400 MHz, DMSO-d$_6$) δ 8.50 (brs, 2H), 7.54 (d, J=8.0 Hz, 2H), 7.34 (d, J=8.0 Hz, 2H), 7.28 (d, J=8.0 Hz, 2H), 7.01 (d, J=8.0 Hz, 2H), 4.06 (t, J=6.0 Hz, 2H), 3.81 (s, 3H), 3.62-3.59 (m, 2H), 3.23 (t, J=6.0 Hz, 2H), 2.42-2.38 (m, 2H), 1.88-1.84 (m, 4H). LCMS (ESI) m/z: 484.2 (M+1). Fraction 2: $^1$H NMR (400 MHz, DMSO-d$_6$) δ 8.50 (br s, 2H), 7.54 (d, J=8.0 Hz, 2H), 7.34 (d, J=8.0 Hz, 2H), 7.28 (d, J=8.0 Hz, 2H), 7.01 (d, J=8.0 Hz, 2H), 4.06 (t, J=6.0 Hz, 2H), 3.81 (s, 3H), 3.62-3.59 (m, 2H), 3.23 (t, J=6.0 Hz, 2H), 2.42-2.38 (m, 2H), 1.88-1.84 (m, 4H). MS (ESI) m/z: 484.2 (M+1).

Example 9

1-(4-Chlorophenyl)-7-oxo-6-(1-(3-oxomorpholino)piperidin-4-yl)-4,5,6,7-tetrahydro-1H-pyrazolo[3,4-c]pyridine-3-carboxamide

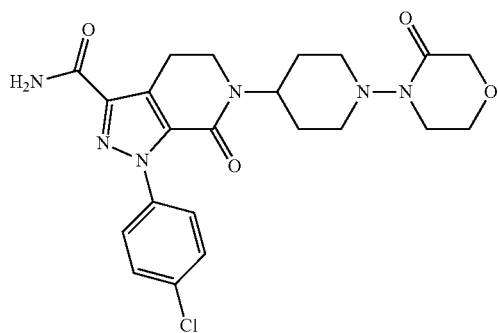 [SMILES: NC(=O)c1nn(-c2ccc(Cl)cc2)c2c1CCN(C1CCN(N3CCOCC3=O)CC1)C2=O]

Step A: 1-(4-Chlorophenyl)-7-oxo-6-(1-(3-oxomorpholino)piperidin-4-yl)-4,5,6,7-tetrahydro-1H-pyrazolo[3,4-c]pyridine-3-carboxamide is prepared according to the procedure used for the preparation of example 4, steps A-K sequence, replacing (Z)-ethyl 2-chloro-2-(2-(4-methoxyphenyl)hydrazono)acetate by (Z)-ethyl 2-chloro-2-(2-(4-chlorophenyl)hydrazono)acetate in step B. The title compound is obtained as a white solid. $^1$H NMR (400 MHz, DMSO-d$_6$) δ 7.73 (br s, 1H), 7.62 (d, J=8.8 Hz, 2H), 7.56 (d, J=8.8 Hz, 2H), 7.45 (br s, 1H), 4.29-4.25 (m, 1H), 3.97 (s, 2H), 3.81-3.78 (m, 2H), 3.56-3.53 (m, 2H), 3.42-3.37 (m, 4H), 3.02-2.98 (m, 4H), 1.84-1.76 (m, 2H), 1.60-1.56 (m, 2H). LCMS (ESI) m/z: 473 (M+1).

Example 10

7-Oxo-6-(1-(3-oxomorpholino)piperidin-4-yl)-1-(4-(trifluoromethoxy)phenyl)-4,5,6,7-tetra hydro-1H-pyrazolo[3,4-c]pyridine-3-carboxamide

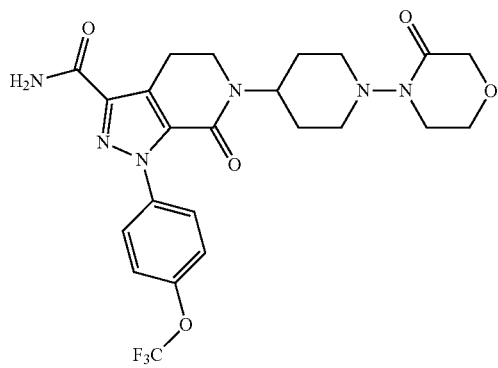 [SMILES: NC(=O)c1nn(-c2ccc(OC(F)(F)F)cc2)c2c1CCN(C1CCN(N3CCOCC3=O)CC1)C2=O]

Step A: 7-Oxo-6-(1-(3-oxomorpholino)piperidin-4-yl)-1-(4-(trifluoromethoxy)phenyl)-4,5,6,7-tetrahydro-1H-pyrazolo[3,4-c]pyridine-3-carboxamide is prepared according to the procedure used for the preparation of example 4, steps A-K sequence, replacing (Z)-ethyl 2-chloro-2-(2-(4-methoxyphenyl)hydrazono)acetate by (Z)-ethyl 2-chloro-2-(2-(4-(trifluoromethoxy)phenyl)hydrazono)acetate in step B. The title compound is obtained as a white solid. $^1$HNMR (400 MHz, DMSO-d$_6$) δ 7.74-7.72 (m, 3H), 7.52-7.50 (m, 2H), 7.46 (s, 1H), 4.27 (t, J=12.0 Hz, 1H), 3.98 (s, 2H), 3.82-3.80 (m, 2H), 3.57 (t, J=6.4 Hz, 2H), 3.43-3.40 (m, 4H), 3.01-2.98 (m, 4H), 1.82-1.77 (m, 2H), 1.59 (d, J=12.0 Hz, 2H).

Example 11

1-(4-(Difluoromethoxy)phenyl)-7-oxo-6-(1-(3-oxomorpholino)piperidin-4-yl)-4,5,6,7-tetra hydro-1H-pyrazolo[3,4-c]pyridine-3-carboxamide

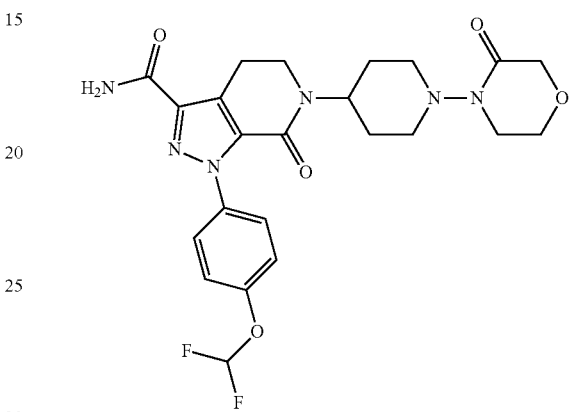

Step A: 1-(4-(Difluoromethoxy)phenyl)-7-oxo-6-(1-(3-oxomorpholino)piperidin-4-yl)-4,5,6,7-tetra hydro-1H-pyrazolo[3,4-c]pyridine-3-carboxamide is prepared according to the procedure used for the preparation of example 4, steps A-K sequence, replacing (Z)-ethyl 2-chloro-2-(2-(4-methoxyphenyl)hydrazono)acetate by (Z)-ethyl 2-chloro-2-(2-(4-(difluoromethoxy)phenyl)hydrazono)acetate in step B. The title compound is obtained as a white solid. $^1$HNMR (400 MHz, DMSO-d$_6$) δ 7.71 (s, 1H), 7.65 (d, J=8.8 Hz, 2H), 7.44 (s, 1H), 7.34 (t, J=74 Hz, 1H), 7.29 (d, J=8.8 Hz, 2H), 4.27-4.22 (m, 1H), 3.98 (s, 2H), 3.77-3.75 (m, 2H), 3.60-3.55 (m, 2H), 3.50-3.40 (m, 4H), 3.02-2.95 (m, 4H), 1.82-1.75 (m, 2H), 1.60-1.55 (m, 2H).

Example 12

1-(4-Methoxyphenyl)-7-oxo-6-(3-(2-oxopiperidin-1-yl)-3-aza bicyclo[3.1.0]hexan-6-yl)-4,5,6,7-tetrahydro-1H-pyrazolo[3,4-c]pyridine-3-carboxamide

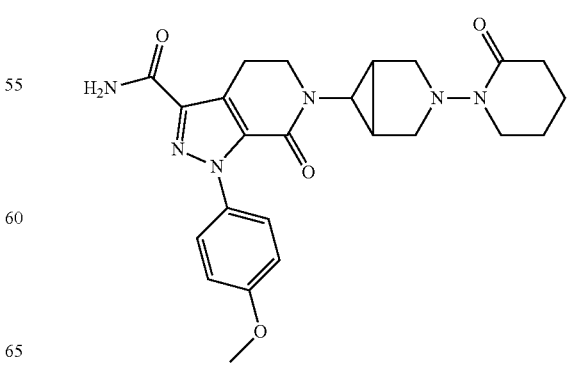

Scheme for the Preparation:

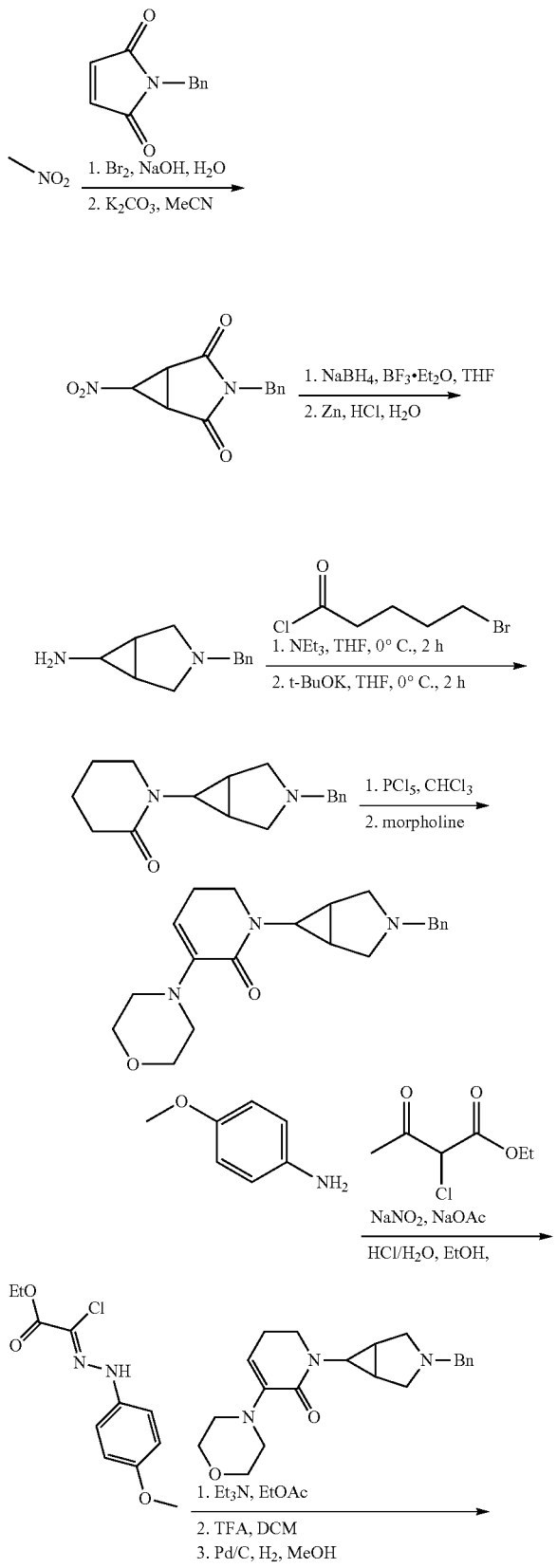

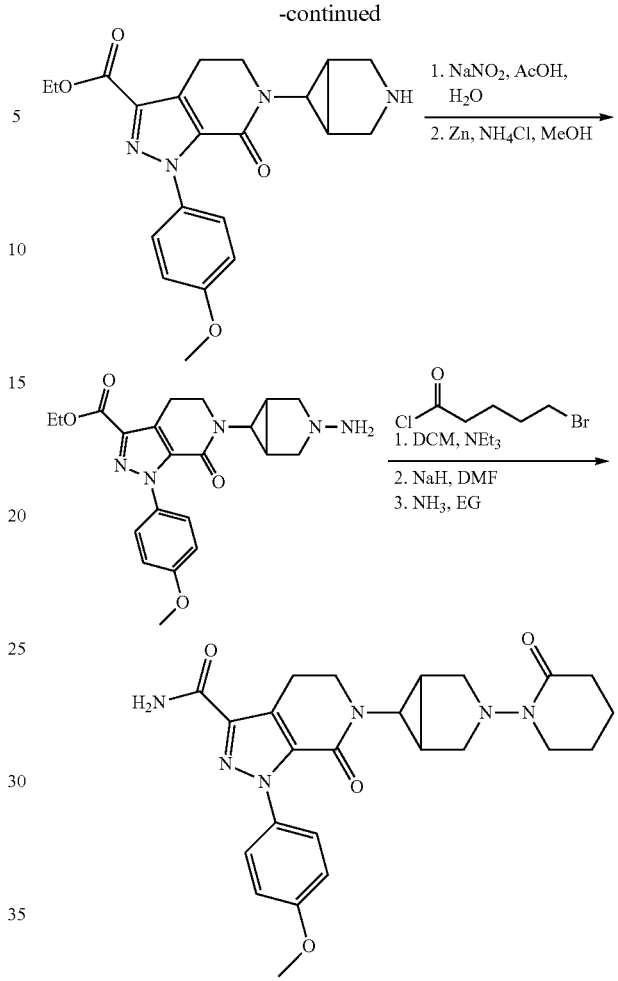

Step A: To a solution of NaOH (12.00 g, 300 mmol) in H₂O (300 mL) was added dropwise nitromethane (18.30 g, 300 mmol) at 0° C. and stirred at 0° C. for 0.5 hour. Br₂ (47.94 g, 300 mmol) in H₂O (100 mL) was added to the mixture within 5 mins at 0° C. and stirred at 0° C. for 10 mins. Excess saturated Na2SO3 solution was added to the mixture and stirred at 0° C. for 0.5 hour. The reaction mixture was extracted with DCM (200 mL×2). The combined organic layers were dried, filtered, concentrated at 25° C. to give bromo(nitro)methane (28.00 g, crude) as a yellow oil which was used directly in the next step.

Step B: To a solution of 1-benzyl-1H-pyrrole-2,5-dione (15.08 g, 81 mmol) in CH₃CN (810 mL) was added bromo(nitro)methane (11.33 g, 81 mmol), followed by added K₂CO₃ (11.19 g, 81 mmol). The mixture was stirred at 25° C. for 4 hours. Then bromo(nitro)methane (1.13 g, 8 mmol) was added every 4 hours×5 times to the reaction mixture at 25° C. and the total number of times is five. The resulting mixture was stirred at 25° C. for 4 hours. The mixture was concentrated in vacuo to give crude. The crude was purified by silica gel column chromatography (EA:PE=1:10 to 1:5) to give 3-benzyl-6-nitro-3-azabicyclo[3.1.0]hexane-2,4-dione (8.00 g, crude) as a yellow solid which was used directly in the next step. LCMS (ESI) m/z: 247 (M+1).

Step C: To a solution of 3-benzyl-6-nitro-3-azabicyclo[3.1.0]hexane-2,4-dione (8.12 g, 33 mmol) in THF (100 mL) was added NaBH₄ (3.74 g, 99 mmol) at −20° C. and stirred at −20° C. for 0.5 hour. Followed by added BF₃.Et₂O (14.05 g, 99 mmol) dropwise over 0.5 hour at −20° C. and stirred at −20° C. for 1 hour. The mixture was warmed to 25° C. and then stirred at 25° C. for 16 hours. To the reaction mixture was added MeOH (25 mL) and stirred at 25° C. for 0.5 hour. The mixture was concentrated in vacuo to give crude. The crude was added to water (50 mL) and extracted with EA (50 mL×3). The combined organic layers were dried, filtered, concentrated to give crude. The crude was added to MeOH (80 mL), stirred at 80° C. for 2 hours and concentrated. The crude residue was purified by salica gel column chromatography (EA:PE=1:50 to 1:30) to give 3-benzyl-6-nitro-3-azabicyclo[3.1.0]hexane (4.70 g, 65%) as a colourless oil. LCMS (ESI) m/z: 219 (M+1).

Step D: To a solution of 3-benzyl-6-nitro-3-azabicyclo [3.1.0]hexane (4.80 g, 22 mmol) in i-PrOH (220 mL) was added 2 M HCl aqueous solution (110 mL, 220 mmol) at 25° C., followed by added Zn powder (28.78 g, 440 mmol) at 25° C. and stirred at 25° C. for 2 hours. NaHCO$_3$ (18.48 g, 220 mmol) was added to the reaction mixture at 25° C. and stirred at 25° C. for 0.5 hour. The mixture was filtered on celite. The filtrate was extracted with DCM (200 mL×3). The combined organic layers were dried, filtered, and concentrated. The crude residue was purified by salica gel column chromatography (DCM:MeOH=30:1 to 10:1) to give 3-benzyl-3-azabicyclo[3.1.0]hexan-6-amine (3.25 g, 78%) as a yellow solid. LCMS (ESI) m/z: 189 (M+1).

Step E: To a solution of 3-benzyl-3-azabicyclo[3.1.0] hexan-6-amine (3.20 g, 17 mmol) in THF (150 mL) was added NEt$_3$ (3.78 g, 37 mmol), followed by added 5-bromopentanoyl chloride (4.07 g, 20 mmol) in THF (20 mL) at 0° C. and stirred at 0° C. for 2 hours. The mixture was poured into saturated NaHCO$_3$ aqueous solution (150 mL), extracted with EtOAc (150 mL×3). The combined organic layers were dried, filtered, concentrated to give crude. The crude was purified by salica gel column chromatography (DCM:MeOH=50:1 to 30:1) to give a intermediate crude. The crude was dissolved in THF (130 mL). To the solution was added t-BuOK (1.90 g, 17 mmol) portion-wise at 0° C. and stirred at 0° C. for 2 hours. The mixture was poured into saturated NH$_4$Cl solution (100 mL), extracted with EtOAc (100 mL×3). The combined organic layers were dried, filtered, and concentrated. The crude residue was purified by salica gel column chromatography (DCM:MeOH=50:1 to 30:1) to give 1-(3-benzyl-3-azabicyclo[3.1.0]hexan-6-yl)piperidin-2-one (2.80 g, 79%) as a white solid. LCMS (ESI) m/z: 271 (M+1).

Step F: To a solution of 1-(3-benzyl-3-azabicyclo[3.1.0] hexan-6-yl)piperidin-2-one (2.03 g, 7.5 mmol) in CHCl$_3$ (24 mL) was added PCl$_5$ (6.25 g, 30.0 mmol) at 25° C. and stirred at 85° C. for 16 hours. After cooled to 0° C., the mixture was poured into ice-water (25 mL) and extracted with CHCl$_3$ (25 mL×2). The combined organic layers were dried, filtered, and concentrated to give 1-(3-benzyl-3-azabicyclo[3.1.0]hexan-6-yl)-3,3-dichloropiperidin-2-one (2.60 g, crude) as a dark-brown solid which was used directly in the next step. LCMS (ESI) m/z: 339 (M+1).

Step G: 1-(3-Benzyl-3-azabicyclo[3.1.0]hexan-6-yl)-3,3-dichloropiperidin-2-one [2.54 g, 7.5 mmol] was dissolved in morpholine (35 mL) and stirred at 130° C. for 16 hours. The mixture was concentrated to give crude. The crude was dissolved in water (20 mL) and extracted with EtOAc (20 mL×3). The combined organic layers were dried, filtered, and concentrated. The crude residue was purified by silica gel column chromatography (DCM:MeOH=40:1) to give 1-(3-benzyl-3-aza bicyclo[3.1.0]hexan-6-yl)-3-morpholino-5,6-dihydropyridin-2(1H)-one (1.70 g, crude) as a brown oil. LCMS (ESI) m/z: 271 (M+1).

Step H: To a solution of 4-methoxyaniline (19.71 g, 160 mmol) in EtOH (40 mL), was added HCl solution (40 mL, 12 M), followed by added a solution of NaNO$_2$ (12.14 g, 176 mmol) in H$_2$O (60 mL) slowly over 20 mins at −5° C. The mixture was stirred at 0° C. for 1 hour. Then ethyl 2-chloro-3-oxobutanoate (26.34 g, 160 mmol), EtOH/H$_2$O (400 mL, 9:1), and NaOAc (20.99 256 mmol) were added in sequence. The resulting mixture was stirred at 0° C. for 0.5 hour, warmed to 25° C. for 2 hours. The solid was collected by filtered, washed with H$_2$O (50 mL×3), dried to give (Z)-methyl 2-chloro-2-(2-(4-methoxyphenyl)hydrazono)acetate (15 g, 36%) as a yellow-green solid. $^1$H NMR (400 MHz, CDCl$_3$) δ 8.29 (br s, 1H), 7.17 (d, J=8.8 Hz, 2H), 6.89 (d, J=8.8 Hz, 2H), 4.38 (q, J=6.4 Hz, 2H), 3.80 (s, 3H), 1.40 (t, J=6.4 Hz, 3H).

Step I: (Z)-ethyl 2-chloro-2-(2-(4-methoxyphenyl)hydrazono)acetate (1.93 g, 7.5 mmol) and 1-(3-benzyl-3-aza bicyclo[3.1.0]hexan-6-yl)-3-morpholino-5,6-dihydropyridin-2 (1H)-one (1.77 g, 5 mmol) was dissolved in EtOAc (40 mL). To the solution was added NEt$_3$ (1.26 g, 12.5 mmol) and stirred at 85° C. for 16 hours. The mixture was cooled to 25° C., poured into water (30 mL), extracted with EtOAc (30 mL×3). The combined organic layers were washed with saturated NaHCO$_3$ solution, dried over anhydrous Na$_2$SO$_4$, filtered, concentrated to give intermediate (3.00 g, crude) as a yellow solid. MS (ESI) m/z: 574 (M+1). The intermediate (3.00 g, crude) was dissolved in DCM (25 mL). To the solution was added TFA (2.5 mL) and stirred at 25° C. for 16 hours. NaHCO$_3$ (10 g, 0.12 mol) was added to the reaction mixture at 25° C. and stirred at 25° C. for 1 hour. The mixture was filtered and concentrated. The crude residue was purified by silica gel column chromatography (DCM:MeOH=50:1 to 20:1) to give ethyl 6-(3-benzyl-3-aza bicyclo[3.1.0]hexan-6-yl)-1-(4-methoxyphenyl)-7-oxo-4,5, 6,7-tetrahydro-1H-pyrazolo[3,4-c]pyridine-3-carboxylate (800 mg, crude) as a brown oil, which was used in the next step directly. LCMS (ESI) m/z: 487 (M+1).

Step J: A solution of ethyl 6-(3-benzyl-3-aza bicyclo [3.1.0]hexan-6-yl)-1-(4-methoxyphenyl)-7-oxo-4,5,6,7-tetrahydro-1H-pyrazolo[3,4-c]pyridine-3-carboxylate (779 mg, 1.6 mmol), 10% Pd/C (500 mg) in MeOH (20 mL) was stirred under 50 psi of H$_2$ at 25° C. for 16 hours. The mixture was filtered. The filtrate was concentrated to give ethyl 6-(3-aza bicyclo[3.1.0]hexan-6-yl)-1-(4-methoxyphenyl)-7-oxo-4,5,6,7-tetrahydro-1H-pyrazolo[3,4-c]pyridine-3-carboxylate (700 mg, crude) as a yellow solid, which was used in the next step directly. LCMS (ESI) m/z: 397 (M+1).

Step K: To a solution of ethyl 6-(3-aza bicyclo[3.1.0] hexan-6-yl)-1-(4-methoxyphenyl)-7-oxo-4,5,6,7-tetrahydro-1H-pyrazolo[3,4-c]pyridine-3-carboxylate (674 mg, 1.7 mmol) in AcOH (10 mL) was added NaNO$_2$ (704 mg, 10.2 mmol) in H$_2$O (2 mL) at 0° C. and stirred at 0° C. for 1 hour. The mixture was poured into water (30 mL) and extracted with EtOAc (30 mL×2). The combined organic layers were washed with saturated NaHCO$_3$ solution, dried over anhydrous Na$_2$SO$_4$, filtered, concentrated. The crude residue was purified by salica gel column chromatography (EA:PE=1:2 to 1:1) to give the intermediate (520 mg, 71%) as a yellow solid. LCMS (ESI) m/z: 426 (M+1).

Step L: To a solution of the intermediate (510 mg, 1.2 mmol) in MeOH (20 mL) was added NH$_4$Cl (386 mg, 7.2 mmol), followed by added Zn powder (471 mg, 7.2 mmol) portionwise at 0° C. and stirred at 0° C. for 1 hour. The mixture was filtered. The filtrate was concentrated. The crude residue was purified by salica gel column chromatography (DCM:MeOH=30:1 to 10:1) to give ethyl 6-(3-amino-3-aza bicyclo[3.1.0]hexan-6-yl)-1-(4-methoxyphenyl)-7-oxo-4,5,6,7-tetrahydro-1H-pyrazolo[3,4-c]pyridine-3-carboxylate (370 mg, 74%) as a white solid. LCMS (ESI) m/z: 412 (M+1).

Step M: To a solution of ethyl 6-(3-amino-3-aza bicyclo[3.1.0]hexan-6-yl)-1-(4-methoxyphenyl)-7-oxo-4,5,6,7-tetrahydro-1H-pyrazolo[3,4-c]pyridine-3-carboxylate (206 mg, 0.5 mmol) in DCM (5 mL) was added NEt$_3$ (111 mg, 1.1 mmol), followed by added 5-bromopentanoyl chloride (120 mg 0.6 mmol) in DCM (1 mL) at 0° C. and stirred at 0° C. for 1 hour. The mixture was poured into saturated NaHCO$_3$ solution (10 mL), extracted with DCM (10 mL×2). The combined organic layers were dried, filtered, concentrated. The crude residue was purified by salica gel column chromatography (DCM:EA=1:1 to 1:3) to give intermediate (235 mg, 81%) as a white solid. LCMS (ESI) m/z: 574 (M+1).

Step N: To a solution of the intermediate (230 mg, 0.4 mmol) in DMF (5 mL) was added NaH (21 mg, 0.5 mmol) at 0° C. and stirred at 0° C. for 2 h. The mixture was poured into saturated NH$_4$Cl solution (20 mL), extracted with EtOAc (20 mL×2). The combined organic layers were dried, filtered, concentrated. The crude residue was purified by salica gel column chromatography (DCM:EA=1:1 to 1:2) to give ethyl 1-(4-methoxyphenyl)-7-oxo-6-(3-(2-oxopiperidin-1-yl)-3-aza bicyclo[3.1.0]hexan-6-yl)-4,5,6,7-tetrahydro-1H-pyrazolo[3,4-c]pyridine-3-carboxylate (110 mg, 55%) as a white solid. LCMS (ESI) m/z: 494 (M+1).

Step O: To a solution of NH$_3$ (gas) in ethane-1,2-diol (6 mL) was added 1-(4-methoxyphenyl)-7-oxo-6-(3-(2-oxopiperidin-1-yl)-3-aza bicyclo[3.1.0]hexan-6-yl)-4,5,6,7-tetrahydro-1H-pyrazolo[3,4-c]pyridine-3-carboxamide (109 mg, 0.2 mmol) in a sealed tube. The mixture was stirred at 80° C. for 16 hours. After cooled to room temperature, the mixture was poured into H$_2$O (30 mL), extracted with EA (25 mL×3). The combined organic layers were dried, filtered, and concentrated. The crude residue was purified by preparative HPLC (HCOOH) to give title product (45 mg, 44%) as a white solid. $^1$H NMR (400 MHz, DMSO) δ 7.65 (br s, 1H), 7.45 (d, J=8.8 Hz, 2H), 7.38 (br s, 1 H), 7.01 (d, J=8.8 Hz, 2H), 3.82 (s, 3H), 3.61-3.53 (m, 4H), 3.28-3.26 (m, 2H), 3.03-2.98 (m, 4H), 2.74-2.72 (m, 1H), 2.19-2.16 (m, 2H), 1.74-1.68 (m, 4H), 1.60-1.57 (m, 2H). LCMS (ESI) m/z: 465 (M+1).

Example 13

1-(4-Methoxyphenyl)-7-oxo-6-(3-(3-oxomorpholino)-3-azabicyclo[3.1.0]hexan-6-yl)-4,5,6,7-tetrahydro-1H-pyrazolo[3,4-c]pyridine-3-carboxamide

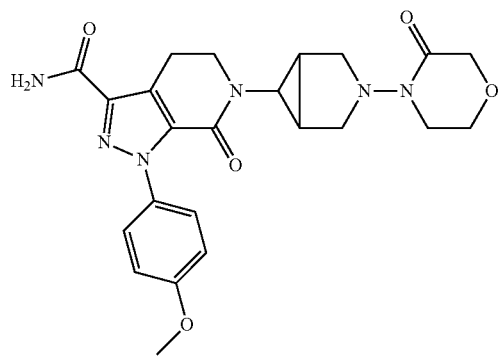 [SMILES: COc1ccc(-n2nc(C(N)=O)c3c2C(=O)N(C2C4CN(N5CCOCC5=O)CC42)CC3)cc1]

Step A: To DCM (2.0 mL) was added HATU (125 mg, 0.33 mmol) and 2-(2-chloroethoxy)acetic acid (46 mg, 0.33 mmol) in DCM (0.5 mL), followed by added DIPEA (76 mg 0.60 mmol) at 25° C. and stirred at 25° C. for 0.5 hour. Then 6-(3-amino-3-aza bicyclo[3.1.0]hexan-6-yl)-1-(4-methoxyphenyl)-7-oxo-4,5,6,7-tetrahydro-1H-pyrazolo[3,4-c]pyridine-3-carboxylate ethyl (123 mg, 0.30 mmol) in DCM (0.5 mL) was added to the reaction mixture at 25° C. and stirred at 25° C. for 16 hours. The mixture was poured into saturated NaHCO$_3$ solution (10 mL), extracted with DCM (10 mL×2). The combined organic layers were dried, filtered, concentrated. The crude residue was purified by salica gel column chromatography (DCM:EA=1:1 to 0:1) to give ethyl 6-(3-(2-(2-chloroethoxy)acetamido)-3-aza bicyclo[3.1.0]hexan-6-yl)-1-(4-methoxyphenyl)-7-oxo-4,5,6,7-tetrahydro-1H-pyrazolo[3,4-c]pyridine-3-carboxylate (80 mg, 50%) as a yellow oil. LCMS (ESI) m/z: 532 (M+1).

Step B: Ethyl 6-(3-(2-(2-chloroethoxy)acetamido)-3-aza bicyclo[3.1.0]hexan-6-yl)-1-(4-methoxyphenyl)-7-oxo-4,5,6,7-tetrahydro-1H-pyrazolo[3,4-c]pyridine-3-carboxylate (80 mg, 0.15 mmol) was dissolved in DMF (5 mL). To the solution was added NaH (6 mg, 0.15 mmol) at 0° C. and stirred at 0° C. for 2 hours. The mixture was poured into saturated NH$_4$Cl solution (20 mL), extracted with EtOAc (20 mL×2). The combined organic layers were dried, filtered, and concentrated to give the crude 1-(4-methoxyphenyl)-7-oxo-6-(3-(3-oxomorpholino)-3-aza bicyclo[3.1.0]hexan-6-yl)-4,5,6,7-tetrahydro-1H-pyrazolo[3,4-c]pyridine-3-carboxylate as yellow oil, which was used directly in the next step. LCMS (ESI) m/z: 496 (M+1).

Step C: 1-(4-Methoxyphenyl)-7-oxo-6-(3-(3-oxomorpholino)-3-aza bicyclo[3.1.0]hexan-6-yl)-4,5,6,7-tetrahydro-1H-pyrazolo[3,4-c]pyridine-3-carboxylat (15 mg, 0.03 mmol) was added to a solution of NH$_3$ (gas) in ethane-1,2-diol in a sealed tube. The mixture was stirred at 80° C. for 16 hours. The mixture was poured into H$_2$O (30 mL), extracted with EA (230 mL×3). The combined organic layers were dried, filtered, and concentrated. The crude residue was purified by preparative HPLC (HCOOH) to give 1-(4-methoxyphenyl)-7-oxo-6-(3-(3-oxomorpholino)-3-aza bicyclo[3.1.0]hexan-6-yl)-4,5,6,7-tetrahydro-1H-pyrazolo[3,4-c]pyridine-3-carboxamide (6 mg, 42%) as a white solid. $^1$H NMR (400 MHz, DMSO-d$_6$) δ 7.65 (br s, 1H), 7.45 (d, J=8.8 Hz, 2H), 7.38 (br s, 1H), 7.01 (d, J=8.8 Hz, 2H), 3.97 (s, 2H), 3.82 (s, 3H), 3.81-3.78 (m, 2H), 3.61-3.57 (m, 2H), 3.55-3.52 (m, 2H), 3.36-3.32 (m, 2H), 3.11-3.08 (m, 2H), 3.01-2.97 (m, 2H), 2.76-2.74 (m, 1H), 1.79-1.76 (m, 2H). LCMS (ESI) m/z: 465 (M+1).

Example 14

1-(4-Methoxyphenyl)-7-oxo-6-(2-oxo-[1,4'-bipiperidin]-1'-yl)-4,5,6,7-tetrahydro-1H-pyrazolo[3,4-c]pyridine-3-carboxamide

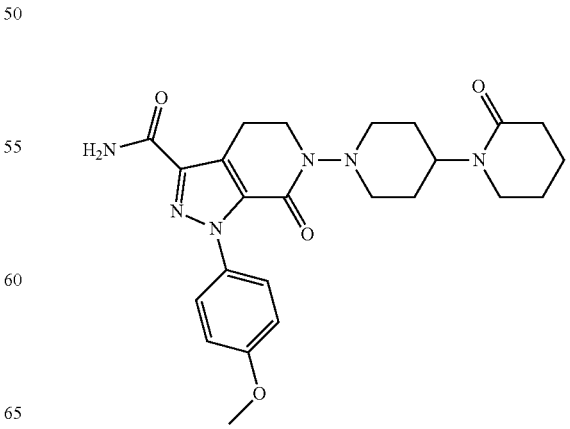

Scheme for the Preparation:

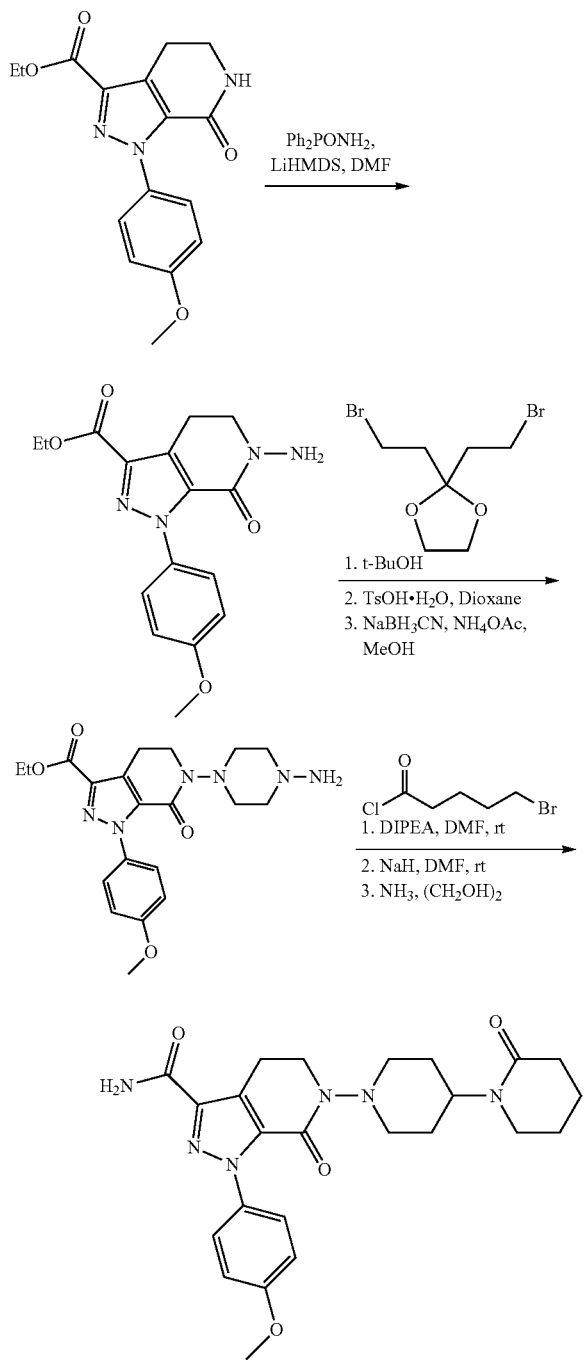

Step A: LiHMDS (17.4 mL, 17.4 mmol) was slowly added to the solution of ethyl 1-(4-methoxyphenyl)-7-oxo-4,5,6,7-tetrahydro-1H-pyrazolo[3,4-c]pyridine-3-carboxylate (5.00 g, 15.8 mmol) in DMF (50 mL) at −10° C. After the mixture was stirred for 10 min, P,P-diphenylphosphinic amide (4.4 g, 19.1 mmol) in DMF (20 mL) was added dropwise at 0° C., followed by stirring at 18° C. for 16 hours. The mixture was poured into water (150 mL), extracted with EA (150 mL×3). The combined organics was dried over anhydrous $Na_2SO_4$, concentrated. The crude residue was purified by silical gel chromatography (PE:EA=4:1 to 1:2) to give ethyl 6-amino-1-(4-methoxyphenyl)-7-oxo-4,5,6,7-tetrahydro-1H-pyrazolo[3,4-c]pyridine-3-carboxylate (3.3 g, 63%) as a white solid. $^1$HNMR (400 MHz, DMSO-$d_6$) δ 7.45 (dd, J=6.8, 2.0 Hz, 2H), 7.01 (dd, J=6.8, 2.0 Hz, 2H), 5.04 (brs, 2H), 4.31 (q, J=7.2 Hz, 2H), 3.82 (s, 3H), 3.75 (t, J=7.2 Hz, 2H), 3.09 (t, J=7.2 Hz, 2H), 1.31 (t, J=7.2 Hz, 3H).

Step B: To a solution of ethyl 6-amino-1-(4-methoxyphenyl)-7-oxo-4,5,6,7-tetrahydro-1H-pyrazolo[3,4-c]pyridine-3-carboxylate (3.3 g, 0.01 mol) in DMF (35 mL) was added 2,2-bis(2-bromoethyl)-1,3-dioxolane (2.86 g, 0.01 mol) and $K_2CO_3$ (1.38, 0.01 mol). The mixture was heated to 100° C. for 16 hours. After cooled to 18° C., the mixture was poured into water (100 mL), extracted with EtOAc (100 mL×2), washed with brine, dried over anhydrous $Na_2SO_4$, and concentrated. The crude residue was purified by silical gel chromatography (PE:EA=1:1) to give ethyl 1-(4-methoxyphenyl)-7-oxo-6-(1,4-dioxa-8-azaspiro[4.5]decan-8-yl)-4,5,6,7-tetrahydro-1H-pyrazolo[3,4-c]pyridine-3-carboxylate (0.9 g, 20%) as a white solid.

Step C: To a solution of ethyl 1-(4-methoxyphenyl)-7-oxo-6-(1,4-dioxa-8-azaspiro[4.5]decan-8-yl)-4,5,6,7-tetrahydro-1H-pyrazolo[3,4-c]pyridine-3-carboxylate (700 mg, 1.54 mmol) in acetone (10 mL) and water (1 mL) was added TsOH·$H_2O$ (132 mg, 0.77 mmol). The mixture was heated to 50° C. for 20 hours. After cooled to room temperature, the solution was poured into saturated $NaHCO_3$ solution, extracted with EtOAc (30 mL×2), dried over anhydrous $Na_2SO_4$, and concentrated. The crude residue was purified by TLC (PE:EA=1:2) to give ethyl 1-(4-methoxyphenyl)-7-oxo-6-(4-oxopiperidin-1-yl)-4,5,6,7-tetrahydro-1H-pyrazolo[3,4-c]pyridine-3-carboxylate (250 mg, 39%) as a white solid.

Step D: To a solution of ethyl 1-(4-methoxyphenyl)-7-oxo-6-(4-oxopiperidin-1-yl)-4,5,6,7-tetrahydro-1H-pyrazolo[3,4-c]pyridine-3-carboxylate (350 mg, 0.849 mmol) in methol (6 mL) was added $NH_4OAc$ (77 mg, 1.27 mmol) and $NaBH_3CN$ (107 mg, 1.69 mmol). The mixture was stirred at 20° C. for 15 hours. The mixture was poured into water (50 mL), extracted with DCM (50 mL). Aqueous layer was collected, and then the solvent was removed by freeze-drying to give ethyl 6-(4-aminopiperidin-1-yl)-1-(4-methoxyphenyl)-7-oxo-4,5,6,7-tetrahydro-1H-pyrazolo[3,4-c]pyridine-3-carboxylate (300 mg, crude) as a white solid. LCMS (ESI) m/z: 414 (M+1).

Step E: ethyl 6-(4-aminopiperidin-1-yl)-1-(4-methoxyphenyl)-7-oxo-4,5,6,7-tetrahydro-1H-pyrazolo[3,4-c]pyridine-3-carboxylate (300 mg, 0.726 mmol, crude) was dissolved in DMF (5 mL). To the solution was added DIPEA (112 mg, 0.871 mmol) and 5-bromopentanoyl chloride (158 mg, 0.799 mmol). The mixture was stirred at 20° C. for 16 hours. The mixture was poured into $NH_4Cl$ solution, extracted with EtOAc (300 mL×2), dried over anhydrous $Na_2SO_4$, and concentrated. The crude residue was purified by TLC (EA) to give ethyl 6-(4-(5-bromopentanamido)piperidin-1-yl)-1-(4-methoxyphenyl)-7-oxo-4,5,6,7-tetrahydro-1H-pyrazolo[3,4-c]pyridine-3-carboxylate (200 mg, 48%) as a yellow solid. LCMS (ESI) m/z: 576 (M+1), 578 (M+3).

Step F: To a solution of ethyl 6-(4-(5-bromopentanamido)piperidin-1-yl)-1-(4-methoxyphenyl)-7-oxo-4,5,6,7-tetrahydro-1H-pyrazolo[3,4-c]pyridine-3-carboxylate (200 mg, 0.347 mmol) in DMF (3 mL) was added NaH (14 mg, 0.347 mmol) at 0° C. Then the reaction mixture was stirred at 20° C. for 16 hours. The mixture was poured into $NH_4Cl$ solution (30 mL), extracted with EA (30 mL×2), dried over anhydrous $Na_2SO_4$, and concentrated. The crude residue was purified by TLC (EA: MeOH=30:1) to give ethyl 1-(4-methoxyphenyl)-7-oxo-6-(2-oxo-[1,4'-bipiperidin]-1'-yl)-4,5,6,7-tetrahydro-1H-pyrazolo[3,4-c]pyridine-3-carboxylate (120 mg, 69%) as a white solid. LCMS (ESI) m/z: 596 (M+1).

Step G: ethyl 1-(4-methoxyphenyl)-7-oxo-6-(2-oxo-[1,4'-bipiperidin]-1'-yl)-4,5,6,7-tetrahydro-1H-pyrazolo[3,4-c]pyridine-3-carboxylate (150 mg, 0.303 mmol) was added to a solution of $NH_3$ (gas) in ethane-1,2-diol in a sealed tube. The mixture was heated to 80° C. for 16 hours. The mixture was poured into water (30 mL), extracted with DCM (30 mL×2), washed with brine, dried over anhydrous $Na_2SO_4$, and concentrated. The crude residue was purified by pre-HPLC (HCl) to give 1-(4-methoxyphenyl)-7-oxo-6-(2-oxo-[1,4'-bipiperidin]-1'-yl)-4,5,6,7-tetrahydro-1H-pyrazolo[3,4-c]pyridine-3-carboxamide (10 mg, 7%) as a white solid. $^1$HNMR (400 MHz, DMSO-$d_6$) δ 7.67 (brs, 1H), 7.46 (dd, J=6.8 Hz, 2.0 Hz, 2H), 7.40 (brs, 1H), 7.31 (dd, J=6.8 Hz, 2.0 Hz, 2H), 4.25 (s, 1H), 3.83 (s, 3H), 3.76-3.72 (m, 2H), 3.70-3.65 (m, 2H), 3.16-3.13 (m, 2H), 3.09-2.89 (m, 4H), 2.22 (t, J=6.0 Hz, 2H), 1.67-1.63 (m, 6H), 1.50-1.47 (m, 2H). LCMS (ESI) m/z: 567 (M+1).

Example 15

1-(4-Methoxyphenyl)-$N^5$-(1-(3-oxomorpholino)piperidin-4-yl)-1H-pyrazole-3,5-dicarboxamide Scheme for the Preparation:

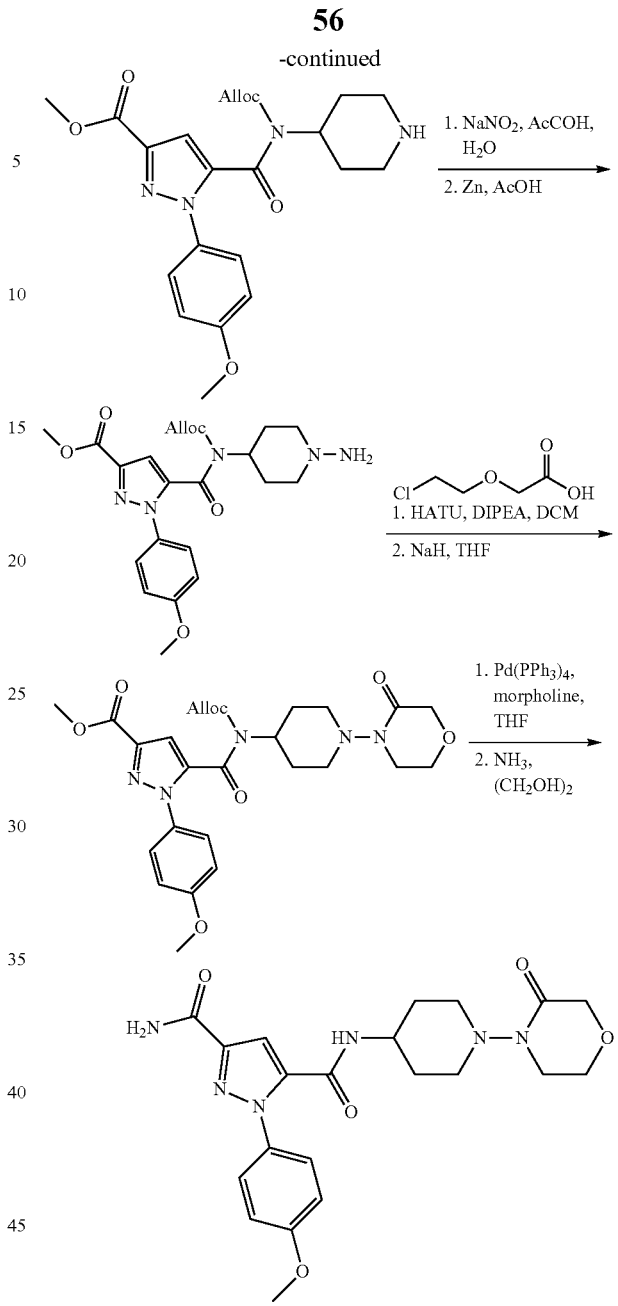

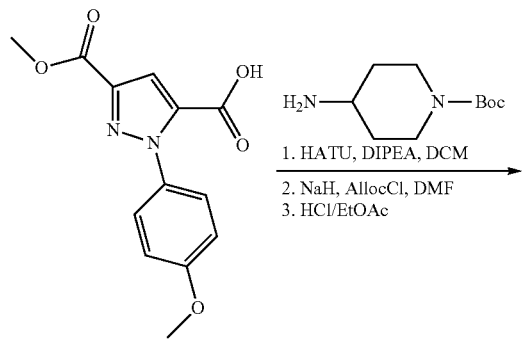

Step A: To a solution of 3-(methoxycarbonyl)-1-(4-methoxyphenyl)-1H-pyrazole-5-carboxylic acid (1 g, 3.62 mmol) in DMF (10 mL) was added HATU (1.65 g, 4.34 mmol), DIEA (0.93 g, 7.24 mmol) and tert-butyl 4-aminopiperidine-1-carboxylate (0.87 g, 4.34 mmol). The mixture was stirred at 20° C. for 16 hours. The mixture was poured into water (60 mL), extracted with EtOAc (60 mL×2). The combined organics was dried over anhydrous $Na_2SO_4$, and concentrated. The crude residue was purified by silical gel chromatography (PE:EA=3:1 to 1:2) to give tert-butyl 4-(3-(methoxycarbonyl)-1-(4-methoxyphenyl)-1H-pyrazole-5-carboxamido)piperidine-1-carboxylate (1.1 g, 68%) as a white solid.

Step B: To a solution of tert-butyl 4-(3-(methoxycarbonyl)-1-(4-methoxyphenyl)-1H-pyrazole-5-carboxamido)piperidine-1-carboxylate (1 g, 2.18 mmol) in DMF (10 mL) was added NaH (0.131 g, 3.27 mmol) at 0° C., followed by allyl carbonochloridate (0.524 g, 4.36 mmol). The mixture was stirred at 20° C. for 16 hours. The mixture was poured into water (50 mL), extracted with EtOAc (50 mL×2), washed with brine, and concentrated. The crude residue was purified by silical gel chromatography (PE:EA=8:1 to 3:1) to give tert-butyl 4-(N-((allyloxy)carbonyl)-3-(methoxycarbonyl)-1-(4-methoxyphenyl)-1H-pyrazole-5-carboxamido)piperidine-1-carboxylate (700 mg, 59%) as a colorless liquid. LCMS (ESI) m/z: 543 (M+1).

Step C: To a solution of 4 M HCl/EtOAc (15 ml) was added tert-butyl 4-(N-((allyloxy)carbonyl)-3-(methoxycarbonyl)-1-(4-methoxyphenyl)-1H-pyrazole-5-carboxamido) piperidine-1-carboxylate (770 mg, 1.42 mmol). The reaction was stirred at 25° C. for 3 hours. The mixture was concentrated to give methyl 5-(((allyloxy)carbonyl)(piperidin-4-yl) carbamoyl)-1-(4-methoxyphenyl)-1H-pyrazole-3-carboxylate (600 mg, 95%) as a white solid.

Step D: To a solution of methyl 5-(((allyloxy)carbonyl) (piperidin-4-yl)carbamoyl)-1-(4-methoxyphenyl)-1H-pyrazole-3-carboxylate (100 mg, 0.226 mmol) in AcOH (4 mL) was added NaNO$_2$ (78 mg, 1.13 mmol, in 2 mL of H$_2$O) at 0° C. The mixture was stirred at 25° C. for 3 hours. The mixture was poured into water (10 mL), extracted with EA (20 mL×2), dried over anhydrous Na$_2$SO$_4$, concentrated to give methyl 5-(((allyloxy)carbonyl)(1-nitrosopiperidin-4-yl) carbamoyl)-1-(4-methoxyphenyl)-1H-pyrazole-3-carboxylate (90 mg, crude) as a yellow solid. LCMS (ESI) m/z: 472 (M+1).

Step E: To a solution of methyl 5-(((allyloxy)carbonyl) (1-nitrosopiperidin-4-yl)carbamoyl)-1-(4-methoxyphenyl)-1H-pyrazole-3-carboxylate (450 mg, 0.849 mmol) in AcOH (6 mL) was added Zn powder (276 mg, 4.24 mmol). The mixture was stirred at 25° C. for 3 hours. The mixture was poured into water (20 mL), extracted with EtOcA (30 mL×2), dried over anhydrous Na$_2$SO$_4$, and concentrated. A small amounts of AcOH was removed by freeze-drying to give methyl 5-(((allyloxy)carbonyl)(1-aminopiperidin-4-yl) carbamoyl)-1-(4-methoxyphenyl)-1H-pyrazole-3-carboxylate (400 mg, 91%) as a yellow solid. LCMS (ESI) m/z: 458 (M+1).

Step F: To a solution of 2-(2-chloroethoxy)acetic acid (181 mg, 1.31 mmol) in DCM (5 mL) was added HATU (399 mg, 1.05 mmol) and DIEA (225 mg, 1.75 mmol). The mixture was stirred for 30 min before methyl 5-(((allyloxy) carbonyl)(1-aminopiperidin-4-yl)carbamoyl)-1-(4-methoxyphenyl)-1H-pyrazole-3-carboxy late (400 mg, 0.875 mmol) was added. The reaction mixture was stirred at 25° C. for 16 hours. The mixture was poured into water (20 mL), extracted with DCM (30 mL×2), dried over anhydrous Na$_2$SO$_4$, and concentrated. The crude residue was purified by silical gel chromatography (PE:EA=5:1 to 1:1) to give methyl 5-(((allyloxy)carbonyl)(1-(2-(2-chloroethoxy)acetamido)piperidin-4-yl)carbamoyl)-1-(4-m ethoxyphenyl)-1H-pyrazole-3-carboxylate (400 mg, 79%) as a yellow solid. LCMS (ESI) m/z: 578 (M+1).

Step G: To a solution of methyl 5-(((allyloxy)carbonyl) (1-(2-(2-chloroethoxy)acetamido)piperidin-4-yl)carbamoyl)-1-(4-m ethoxyphenyl)-1H-pyrazole-3-carboxylate (350 mg, 0.606 mmol) in DMF (5 mL) was added NaH (29 mg, 0.727 mmol) at 0° C. The mixture was stirred at 25° C. for 1 hour. The mixture was poured into water (20 mL), extracted with DCM (30 mL×2), dried over anhydrous Na$_2$SO$_4$, and concentrated to give methyl 5-(((allyloxy) carbonyl)(1-(3-oxomorpholino)piperidin-4-yl)carbamoyl)-1-(4-methoxyphen yl)-1H-pyrazole-3-carboxylate (300 mg, 91%) as a white solid. LCMS (ESI) m/z: 542 (M+1).

Step H: To a solution of methyl 5-(((allyloxy)carbonyl) (1-(3-oxomorpholino)piperidin-4-yl)carbamoyl)-1-(4-methoxyphen yl)-1H-pyrazole-3-carboxylate (360 mg, 0.664 mmol) in DCM (4 mL) was added Pd(PPh$_3$)$_4$ (76 mg, 0.066 mmol) and morpholine (200 uL). The mixture was stirred at 25° C. for 16 hours. The mixture was poured into water (20 mL), extracted with DCM (30 mL×2). The combined organics was dried over anhydrous Na$_2$SO$_4$, and concentrated. The crude residue was purified by TLC (EA) to give methyl 1-(4-methoxyphenyl)-5-((1-(3-oxomorpholino)piperidin-4-yl)carbamoyl)-1H-pyrazole-3-carboxylate (200 mg, 65%) as a white solid. LCMS (ESI) m/z: 458 (M+1).

Step I: To a solution of NH$_3$ (gas) in ethane-1,2-diol (5 mL) was added methyl 1-(4-methoxyphenyl)-5-((1-(3-oxomorpholino)piperidin-4-yl)carbamoyl)-1H-pyrazole-3-carboxylate (200 mg, 0.452 mmol), the mixture was stirred at 80° C. for 16 hours. The mixture was poured into water (50 mL), extracted with DCM (50 mL×3), dried over anhydrous Na$_2$SO$_4$, and concentrated. The crude residue was purified by pre-HPLC (HCOOH) to give 1-(4-methoxyphenyl)-N$^5$-(1-(3-oxomorpholino)piperidin-4-yl)-1H-pyrazole-3,5-dicarboxamide (42 mg, 21%) as a white solid. $^1$HNMR (400 MHz, DMSO-d6) δ 8.56 (d, J=8.0 Hz, 1H), 7.72 (s, 1H), 7.39-7.35 (m, 3H), 7.20 (s, 1H), 7.02 (dd, J=7.2, 2.0 Hz, 2H), 3.96 (s, 2H), 3.81-3.78 (m, 5H), 3.59-3.56 (m, 1H), 3.41-3.34 (m, 4H), 2.98-2.96 (m, 2H), 1.78-1.75 (m, 2H), 1.57-1.52 (m, 2H).

Example 16

1-(4-Methoxyphenyl)-N$^5$-methyl-N$^5$-(1-(3-oxomorpholino)piperidin-4-yl)-1H-pyrazole-3,5-dicarboxamide

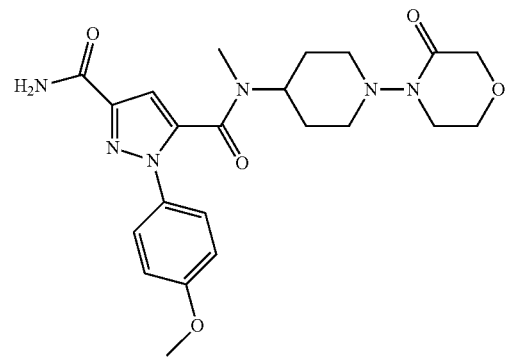 [SMILES: COc1ccc(-n2nc(C(N)=O)cc2C(=O)N(C)C2CCN(N3CCOCC3=O)CC2)cc1]

Step A: ethyl 1-(4-methoxyphenyl)-5-((1-(3-oxomorpholino)piperidin-4-yl)carbamoyl)-1H-pyrazole-3-carboxylate (100 mg, 0.219 mmol) was dissolved in DMF (2 ml). Sodium hydride (13 mg, 0.329 mmol) and iodomethane (62 mg, 0.438 mmol) were added to the solution in portion-wise at 0° C., the mixture was stirred at 0° C. for 2 hours. After the reaction was completed, the mixture was poured into water (10 ml), and extracted with DCM (15 mL×3). The combined organics was dried over anhydrous Na$_2$SO$_4$, filtered, and concentrated. The crude product was used directly in the next step. LCMS (ESI) m/z: 472.1 (M+1).

Step B: To a solution of NH3 (gas) in ethane-1,2-diol (5 ml) was added a solution of methyl1-(4-methoxyphenyl)-5-(methyl(1-(3-oxomorpholino)piperidin-4-yl)carbamoyl)-1H-pyrazole-3-carboxylate (100 mg, 0.212 mmol). The mixture was in 100 ml high pressure reactor stirred at 80° C. for 15 hours. After the reaction was completed, water (10 ml)

was added, extracted by EtOAc (20 ml×3), dried over anhydrous Na$_2$SO$_4$, and concentrated. The crude residue was purified by preparative HPLC (HCOOH) to give the title compound as a white solid. $^1$H NMR (400 MHz, DMSO-d$_6$) δ7.44 (d, J=5.2 Hz, 2H), 7.28 (br. s., 1H), 7.06 (d, J=5.2 Hz 2H), 6.90 (s, 1H), 3.95 (s, 2H), 3.83 (s, 3H), 3.80 (t, J=4.8 Hz, 2H), 3.39 (t, J=4.8 Hz, 3H), 2.96 (brs, 4H), 2.74 (s, 3H), 1.76 (qd, J=12.4, 4.0 Hz, 2H), 1.18-1.64 (m, 2H). LCMS (ESI) m/z: 457.2 (M+1).

Example 17

N$^5$-Ethyl-1-(4-methoxyphenyl)-N$^5$-(1-(3-oxomorpholino)piperidin-4-yl)-1H-pyrazole-3,5-dicarboxamide

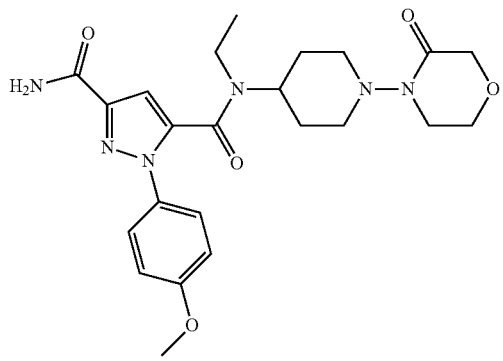 [SMILES: CCN(C(=O)c1cc(C(N)=O)nn1-c1ccc(OC)cc1)C1CCN(N2CCOCC2=O)CC1]

Step A: N$^5$-Ethyl-1-(4-methoxyphenyl)-N$^5$-(1-(3-oxomorpholino)piperidin-4-yl)-1H-pyrazole-3,5-dicarboxamide is prepared according to the procedure used for the preparation of example 16, steps A-K sequence, replacing iodomethane by bromoethane in step A. $^1$H NMR (400 MHz, DMSO-d$_6$) δ 1.03 (t, J=6.4 Hz, 3H) 1.35 (s, 2H) 1.80 (s, 2H) 2.53 (d, J=1.6 Hz, 2H) 2.94 (br. s., 2H) 3.38 (t, J=5.2 Hz, 3H) 3.79 (t, J=5.2 Hz, 2H) 3.83 (s, 3H) 3.97 (br. s., 2H), 6.90 (s, 1H) 7.03-7.11 (m, 2H) 7.14-7.39 (m, 2H) 7.41-7.51 (m, 2H). MS (ESI) m/z: 471.2 (M+1).

Example 18

N$^5$-Cyclopropyl-1-(4-methoxyphenyl)-N$^5$-(1-(3-oxomorpholino) piperidin-4-yl)-1H-pyrazole-3,5-dicarboxamide

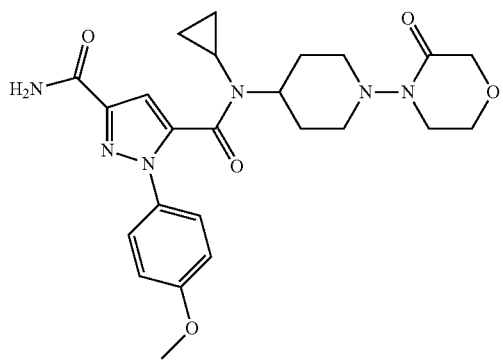 [SMILES: COc1ccc(-n2nc(C(N)=O)cc2C(=O)N(C2CC2)C2CCN(N3CCOCC3=O)CC2)cc1]

Step A: Tert-butyl 4-oxopiperidine-1-carboxylate (8 g, 40.2 mmol), cyclopropanamine (2.52 g, 44.2 mmol) and CH$_3$COOH (2.41 g, 40.2 mmol) was added to MeOH (15 mL). The mixture was stirred at 30° C. for 5 hours. NaBH$_3$CN (3.53 g, 56.2 mmol) was added in portions at 0° C. The reaction mixture was stirred at 30° C. for 16 hours. The mixture was concentrated and purified by silical gel chromatography (PE:EA=3:1 to 1:1) to give tert-butyl 4-(cyclopropylamino)piperidine-1-carboxylate (5 g, 52%) as colorless oil. $^1$HNMR (400 MHz, CDCl$_3$) δ 3.90-4.16 (m, 2H), 2.66-2.89 (m, 3H), 2.13 (s, 1H), 1.82-1.97 (m, 2H), 1.45 (s, 10H), 1.15-1.33 (m, 2H), 0.42-0.49 (m, 2H), 0.30-0.36 (m, 2H).

Step B: N$^5$-cyclopropyl-1-(4-methoxyphenyl)-N$^5$-(1-(3-oxomorpholino)piperidin-4-yl)-1H-pyrazole-3,5-dicarboxamide is prepared according to the procedure used for the preparation of example 15, steps A-I sequence, replacing NH by cyclopropylamine in step A. The crude was purified by preparative HPLC (HCOOH) to give the title compound (34 mg, 35%) as a white solid. $^1$HNMR (400 MHz, DMSO-d$_6$) δ 7.68-7.73 (m, 1H), 7.36-7.43 (m, 3H), 7.04-7.10 (m, 2H), 6.98-7.01 (m, 1H), 3.97 (s, 2H), 3.80 (s, 6H), 3.37-3.50 (m, 4H), 2.91-3.04 (m, 2H), 2.05-2.15 (m, 1H), 1.84-1.99 (m, 2H), 1.54-1.68 (m, 2H), 0.38-0.63 (m, 4H).

Example 19

1-(4-Methoxyphenyl)-N$^5$-(1-(3-oxomorpholino)pyrrolidin-3-yl)-1H-pyrazole-3,5-dicarboxamide

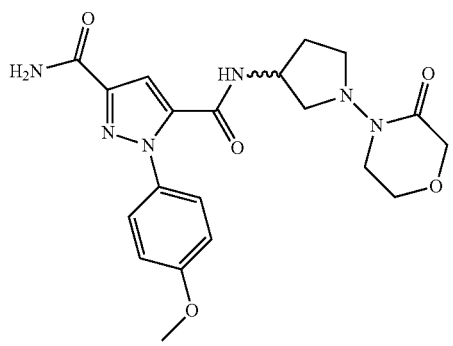 [SMILES: COc1ccc(-n2nc(C(N)=O)cc2C(=O)NC2CCN(N3CCOCC3=O)C2)cc1]

Step A: 1-(4-Methoxyphenyl)-N$^5$-(1-(3-oxomorpholino) pyrrolidin-3-yl)-1H-pyrazole-3,5-dicarboxamide is prepared according to the procedure used for the preparation of example 15, steps A-I sequence, replacing tert-butyl 3-amino pyrrolidine-1-carboxylate by tert-butyl 4-aminopiperidine-1-carboxylate in step A. The crude was purified by preparative HPLC (HCOOH) to give the title compound (11.5 mg, 17%) as an offwhite solid. $^1$HNMR (400 MHz, DMSO-d$_6$) δ 8.89 (d, J=7.2 Hz, 1H), 8.44 (s, 1H), 7.70 (s, 1H), 7.37 (d, J=8.4 Hz, 3H), 7.24 (s, 1H), 7.02 (d, J=8.8 Hz, 2H), 4.30 (t, J=6.0 Hz, 1H), 4.03 (s, 2H), 3.84 (d, J=5.2 Hz, 1H), 3.82 (s, 3H), 3.46-3.45 (m, 3H), 3.27-3.25 (m, 1H), 3.21-3.17 (m, 1H), 3.07-3.05 (m, 1H), 2.08-2.01 (m, 1H), 1.80-1.75 (m, 1H).

Example 20

N⁵-(1-(3-Oxomorpholino)piperidin-4-yl)-1-(tetrahydro-2H-pyran-4-yl)-1H-pyrazole-3,5-dicarboxamide

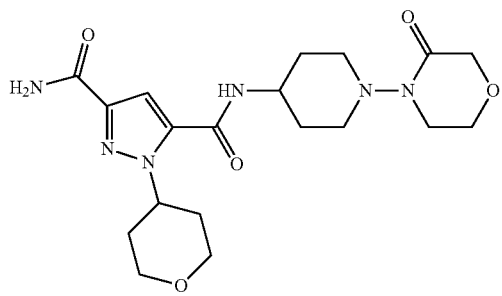 [SMILES: NC(=O)c1cc(C(=O)NC2CCN(N3CCOCC3=O)CC2)n(C2CCOCC2)n1]

Scheme for the Preparation:

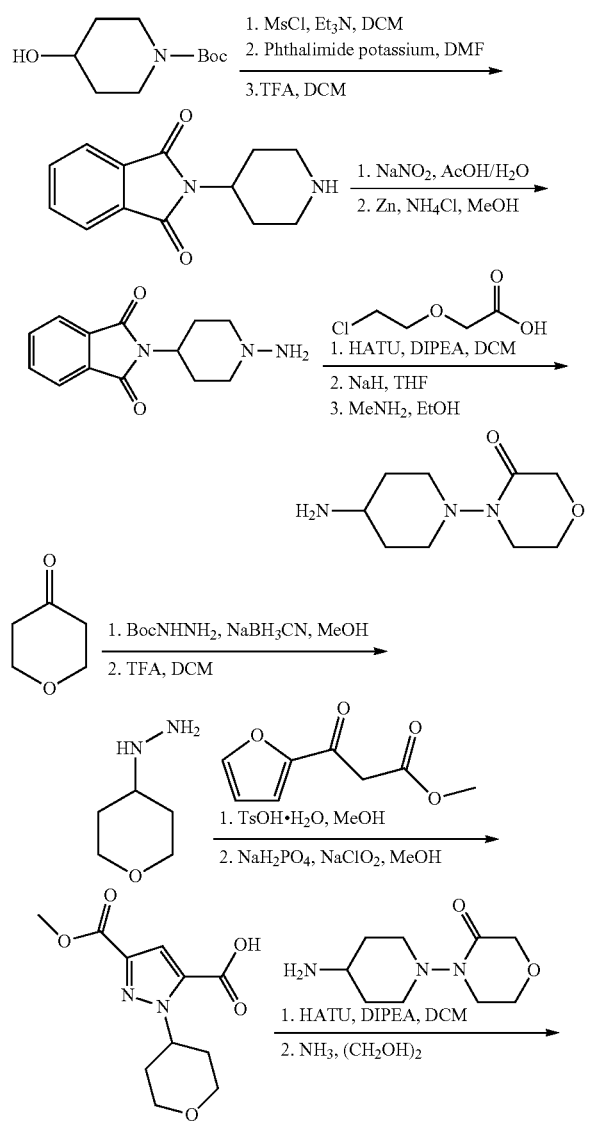

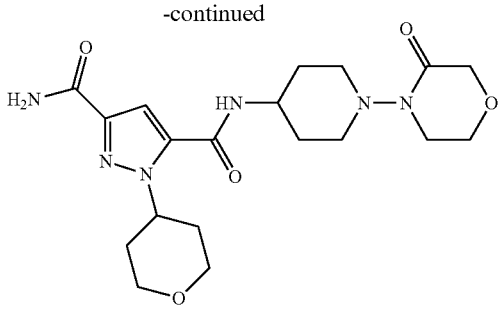

Step A: To a solution of tert-butyl 4-hydroxypiperidine-1-carboxylate (100 g, 0.5 mol) in DCM (1 L), triethylamine (101 g, 1.0 mol) was added at 0° C., The mixture was stirred at 0° C. for 10 minutes. Then methanesulfonyl chloride (62.7 g, 0.55 mol) was added dropwise at 0° C. The mixture was stirred at room temperature for 15 hours. The mixture was washed by saturated NaHCO₃ solution (200 ml×2), then washed by water (200 ml×3). The organic phase was dried over anhydrous Na₂SO₄, and filtered. The filtrate was concentrated to give tert-butyl 4-((methanesulfonyl)oxy)piperidine-1-carboxylate (130 g, 92.2%) as a white solid.

Step B: To a solution of tert-butyl 4-((methylsulfonyl)oxy) piperidine-1-carboxylate (130 g, 0.466 mol) in DMF (1 L), potassium 1,3-dioxoisoindolin-2-ide (92.3 g, 0.699 mol) was added. The mixture was stirred at 80° C. for 16 hours. The mixture was poured into water, white solid was separated out, and filtered. The white solid was dissolved in DCM, dried over anhydrous Na₂SO₄, filtered. The filtrate was concentrated to give the desired product (55 g, 36%) as a white solid.

Step C: To a solution of tert-butyl 4-(1,3-dioxoisoindolin-2-yl) piperidine-1-carboxylate (55 g, 0.167 mol) in DCM (500 ml), TFA (100 ml) was added at 0° C. The mixture was stirred at 0° C. for 2 hours. DCM and TFA was removed in vacuo to afford the crude product, which was used directly in the next step.

Step D: To a solution of 2-(piperidin-4-yl)isoindoline-1,3-dione (30 g, 0.13 mol) in AcOH (350 mL), a solution of sodium nitrite (18 g, 0.26 mol) in water (150 mL) was added at 0° C., the mixture was stirred at 30° C. for 3 hours. The mixture was poured into water (500 ml), white solid was separated out, and filtered. The white solid was dissolved in DCM, washed with saturated NaHCO3 solution (300 ml×4), dried over anhydrous Na₂SO₄, filtered. The filtrate was concentrated to give the desired product (24.8 g, 73.4%) as a white solid.

Step E: To a mixture of 2-(1-nitrosopiperidin-4-yl)isoindoline-1,3-dione (6.5 g, 0.025 mol) in DCM (75 ml) and MeOH (250 ml), Zn powder (6.5 g, 0.1 mol), NH₄Cl (5.4 g, 0.1 mol) was added at 0° C. The mixture was stirred at 0° C. for 30 minutes, then stirred at 15° C. for 1 hour. The mixture was filtrated, the filtrate was extracted by DCM (300 ml×6). The combined organic layers were dried over anhydrous Na₂SO₄, filtrated. The crude residue was purified by silica gel chromatography (DCM:MeOH=20:1) to afford the desired product as a yellow solid.

Step F: To DMF (150 ml) was added 2-(2-chloroethoxy) acetic acid (6.2 g, 0.0449 mol), HATU (18.6 g, 0.049 mol), DIEA (6.8 g, 0.049 mol). The mixture was stirred at 30° C. for 20 minutes, then 2-(1-aminopiperidin-4-yl)isoindoline-1,3-dione (10.0 g, 0.0408 mol) was added. The mixture was stirred at 30° C. for 16 hours. After the reaction completed, the mixture was poured into water (200 ml), white solid was separated out, filtrated. The solid was dissolved in DCM (300 ml), dried over anhydrous Na$_2$SO$_4$, filtered. The filtrate was concentrated to get the desired product (12.5 g, 83.9%) as a white solid.

Step G: To a solution of 2-(2-chloroethoxy)-N-(4-(1,3-dioxoisoindolin-2-yl)piperidin-1-yl)acetamide (12.5 g, 0.038 mol) in DMF (300 ml) was added sodium hydride (1.5, 0.042 mol) at 0° C. for 1 hour. The mixture was stirred at 0° C. for 30 minutes. After the reaction was completed, the mixture was poured into water (300 mL). White solid was separated out, filtered. The white solid was dissolved in DCM (300 mL), washed with water, and dried over anhydrous Na$_2$SO$_4$, filtered. The filtrate was concentrated to get the desired product (9.0 g, 79.6%) as a white solid.

Step H: To a solution of 2-(1-(3-oxomorpholino)piperidin-4-yl)isoindoline-1,3-dione (9.0 g, 0.027 mol) in MeOH (300 ml) methanamine (10.6 ml, 0.136 mol) was added. The mixture was stirred at 70° C. for 3 hours. After the reaction was completed, methanol was removed in vacuo to afford the crude product. It was purified by silica gel chromatography to afford the desired product (2.0 g, 37%) as a white solid.

Step I: To a solution of dihydro-2H-pyran-4(3H)-one (5 g, 0.05 mol) in MeOH (60 mL) was added tert-butyl hydrazinecarboxylate (7.92 g, 0.06 mol), AcOH (500 uL) and NaBH$_3$CN (6.3 g, 0.1 mol). The mixture was stirred at 25° C. for 16 hours, then concentrated. The residue was dissolved in DCM (100 mL), washed with water (80 mL), dried over anhydrous Na$_2$SO$_4$, concentrated. The crude residue was purified by silical gel chromatography (PE:EA=5:1 to 1:1) to give tert-butyl 2-(tetrahydro-2H-pyran-4-yl)hydrazinecarboxylate (10 g, 92%) as a white solid.

Step J: To a solution of tert-butyl 2-(tetrahydro-2H-pyran-4-yl) hydrazinecarboxylate (11 g, 0.05 mol) in DCM (100 mL) was added trifluoroacetate (10 mL). The mixture was stirred at 25° C. for 16 hours, then concentrated, the crude (tetrahydro-2H-pyran-4-yl)hydrazine trifluoroacetate salt (6 g, crude) was used directly in next step.

Step K: To a solution of (tetrahydro-2H-pyran-4-yl)hydrazine trifluoroacetate salt (6 g, crude) in MeOH (80 mL) was added methyl 3-(furan-2-yl)-3-oxopropanoate (10 g, 51.7 mmol) and TsOH.H$_2$O (9.8 g, 51.7 mmol). The mixture was stirred at 60° C. for 16 hours. The mixture was poured into water (100 mL), extracted with EtOAc (100 mL×2), dried over anhydrous Na$_2$SO$_4$, and concentrated. The crude was purified by silical gel chromatography (PE:EA=10:1 to 1:1) to give methyl 5-(furan-2-yl)-1-(tetrahydro-2H-pyran-4-yl)-1H-pyrazole-3-carboxylate (3.7 g, 26%) as a yellow solid. LCMS (ESI) m/z: 277 (M+1).

Step L: To a solution of methyl 5-(furan-2-yl)-1-(tetrahydro-2H-pyran-4-yl)-1H-pyrazole-3-carboxylate (1 g, 3.62 mmol) in MeCN (12 mL) and H$_2$O (6 mL) was added NaH$_2$PO$_4$ (2.17 g, 18.1 mmol) and NaClO$_2$ (3.27 g, 36.2 mmol). The mixture was stirred at 25° C. for 16 h. The mixture was poured into saturated NaHSO$_3$ aqueous solution (50 mL), extracted with EtOAc (50 mL×2), washed with brine, dried over anhydrous Na$_2$SO$_4$, and concentrated to give 3-(methoxycarbonyl)-1-(tetrahydro-2H-pyran-4-yl)-1H-pyrazole-5-carboxylic acid (500 mg, crude) as a yellow solid.

Step M: To a solution of 3-(methoxycarbonyl)-1-(tetrahydro-2H-pyran-4-yl)-1H-pyrazole-5-carboxylic acid (150 mg, 0.59 mmol) in DMF (4 mL) was added HATU (269 mg, 0.707 mmol), DIEA (152 mg, 1.18 mmol) and 4-(4-aminopiperidin-1-yl)morpholin-3-one (117 mg, 0.59 mmol). The mixture was stirred at 25° C. for 16 hours. The mixture was poured into water (30 mL), extracted with EtOAc (40 mL×2), dried over anhydrous Na$_2$SO$_4$, and concentrated. The crude was purified by TLC (EA) to give methyl 5-((1-(3-oxomorpholino)piperidin-4-yl)carbamoyl)-1-(tetrahydro-2H-pyran-4-yl)-1H-pyrazole-3-carboxylate (170 mg, crude) as a yellow oil. LCMS (ESI) m/z: 436 (M+1).

Step N: To a solution of NH$_3$ (gas) in ethane-1,2-diol (10 mL) was added methyl 5-((1-(3-oxomorpholino)piperidin-4-yl)carbamoyl)-1-(tetrahydro-2H-pyran-4-yl)-1H-pyrazole-3-carboxylate (170 mg, crude), the mixture was stirred at 80° C. for 8 hours in a sealed tube. The mixture was poured into water (30 mL) after cooled, extracted with DCM (30 mL×2), dried over anhydrous Na$_2$SO$_4$, and concentrated. The crude residue was purified by preparative HPLC to give N$^5$-(1-(3-oxomorpholino)piperidin-4-yl)carbamoyl)-1-(tetrahydro-2H-pyran-4-yl)-1H-pyrazole-3,5-dicarboxamide (9.1 mg, 5%) as a white solid. $^1$HNMR (400 MHz, DMSO-d$_6$) δ 8.48-8.43 (m, 2H), 7.53 (s, 1H), 7.31 (s, 1H), 7.24 (m, 1H), 5.35-5.29 (m, 1H), 3.97-3.94 (m, 4H), 3.80-3.79 (m, 2H), 3.55-3.53 (m, 1H), 3.45-3.41 (m, 6H), 3.01-3.98 (m, 2H), 2.12-2.07 (m, 2H), 1.87-1.80 (m, 4H), 1.61-1.60 (m, 2H).

Example 21

1-(1-(Methylsulfonyl)piperidin-4-yl)-N$^5$-(1-(3-oxomorpholino)piperidin-4-yl)-1H-pyrazole-3,5-dicarboxamide

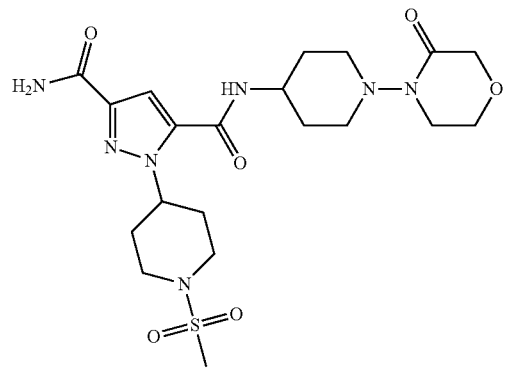 [SMILES: CS(=O)(=O)N1CCC(n2nc(C(N)=O)cc2C(=O)NC2CCN(N3CCOCC3=O)CC2)CC1]

Step A: 1-(1-(Methylsulfonyl)piperidin-4-yl)-N$^5$-(1-(3-oxomorpholino)piperidin-4-yl)-1H-pyrazole-3,5-dicarboxamide is prepared according to the procedure used for the preparation of example 20, steps I-N sequence, replacing dihydro-2H-pyran-4(3H)-one by benzyl 4-oxopiperidine-1-carboxylate in step I. The crude was purified by preparative HPLC (HCOOH) to give the title compound (15 mg, 17%) as a white solid. $^1$HNMR (400 MHz, DMSO-d$_6$) δ 8.44 (d, J=7.6 Hz, 1H), 7.56 (s, 1H), 7.31 (s, 1H), 7.25 (s, 1H), 5.27-5.22 (m, 1H), 3.97 (s, 2H), 3.81-3.79 (m, 2H), 3.69-3.66 (m, 3H), 3.41 (t, J=5.2 Hz, 3H), 3.02-2.99 (m, 2H), 2.92-2.90 (m, 6H), 2.12-2.09 (m, 4H), 2.04-1.82 (m, 2H), 1.80-1.61 (m, 2H).

Example 22

1-(4-Methoxycyclohexyl)-N⁵-(1-(3-oxomorpholino)piperidin-4-yl)-1H-pyrazole-3,5-dicarboxamide

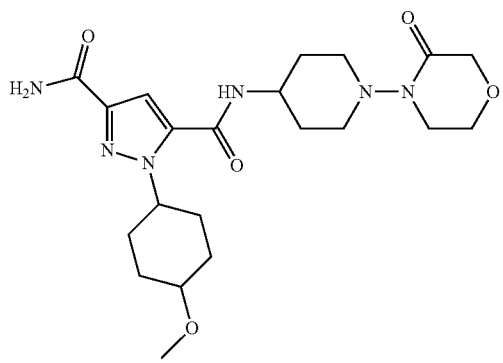 [SMILES: COC1CCC(n2nc(C(N)=O)cc2C(=O)NC2CCN(N3CCOCC3=O)CC2)CC1]

Step A: 1-(4-Methoxycyclohexyl)-N⁵-(1-(3-oxomorpholino)piperidin-4-yl)-1H-pyrazole-3,5-dicarboxamide is prepared according to the procedure used for the preparation of example 20, steps I-N sequence, replacing dihydro-2H-pyran-4(3H)-one by 4-methoxycyclohexanone in step I. ¹HNMR (400 MHz, DMSO-$d_6$) δ 8.41 (d, J=7.6 Hz, 1H), 7.46 (brs, 1H), 7.30 (brs, 1H), 7.22 (s, 1H), 5.08 (m, 1H), 3.98 (s, 2H), 3.71 (m, 2H), 3.69 (m, 1H), 3.43-3.37 (m, 4H), 3.26 (s, 3H), 3.18 (m, 1H), 3.00 (m, 2H), 2.13-2.10 (m, 2H), 1.95-1.80 (m, 6H), 1.62-1.57 (m, 2H), 1.26-1.23 (m, 2H).

Example 23

4-(4-(1-(4-(Difluoromethoxy)phenyl)-7-oxo-3-(trifluoromethyl)-4,5-dihydro-1H-pyrazolo[3,4-c]pyridin-6(7H)-yl)piperidin-1-yl)morpholin-3-one

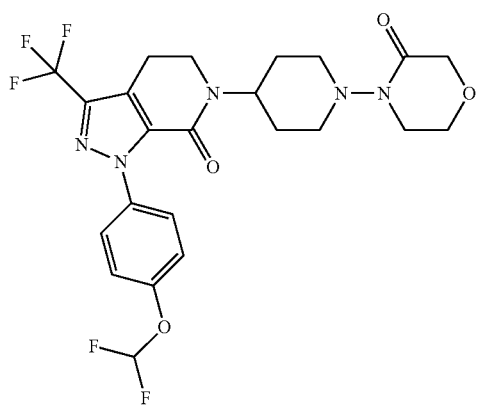

Scheme for the Preparation:

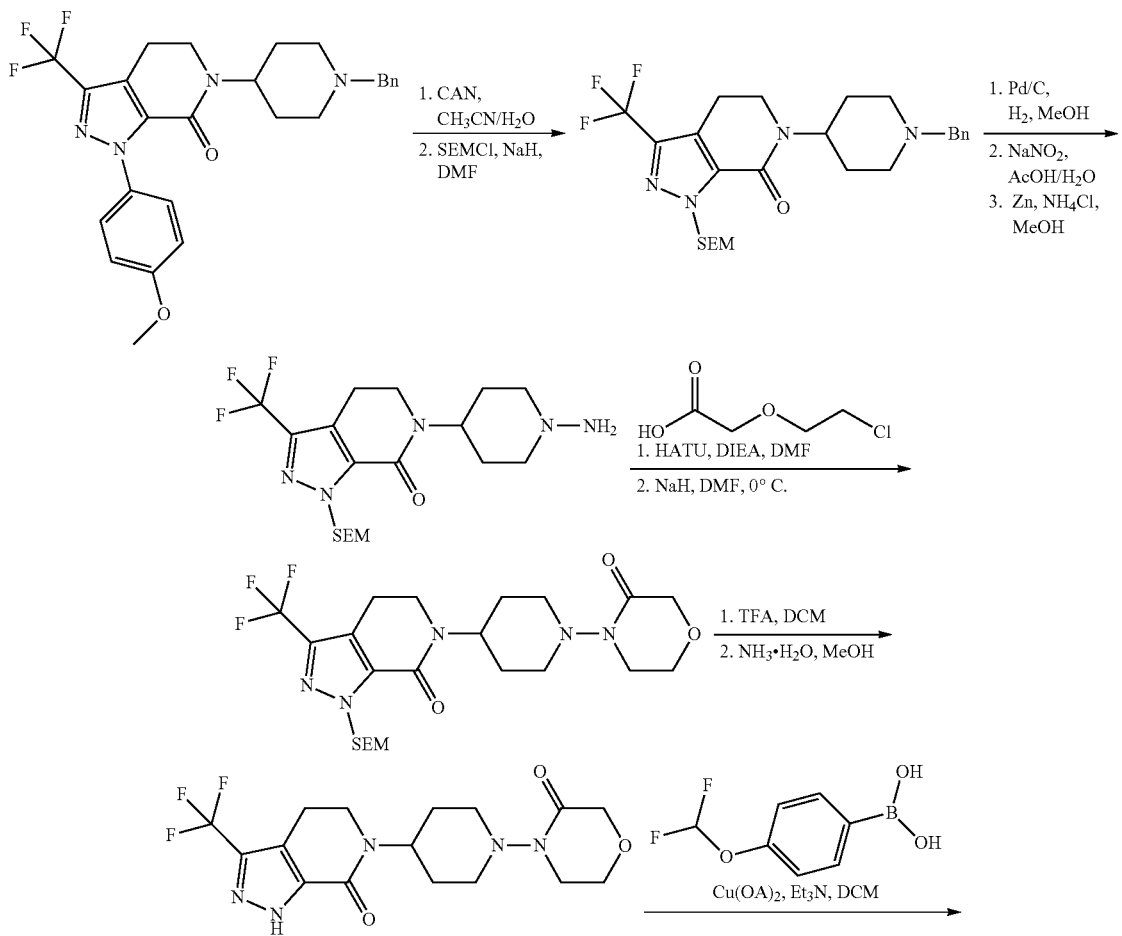

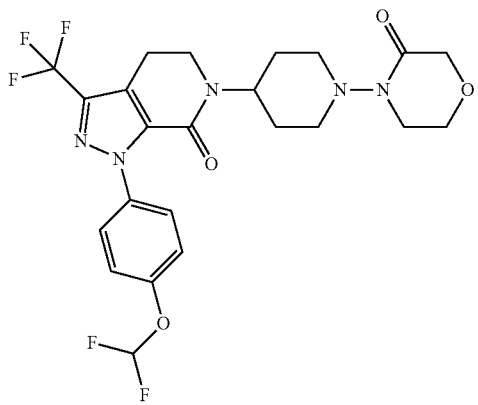 [SMILES: O=C1c2c(c(C(F)(F)F)nn2-c2ccc(OC(F)F)cc2)CCN1C1CCN(N2CCOCC2=O)CC1]

Step A: To a solution of 6-(1-benzylpiperidin-4-yl)-1-(4-methoxyphenyl)-3-(trifluoromethyl)-5,6-dihydro-1H-pyrazolo[3,4-c]pyridin-7(4H)-one (7.5 g, 15.5 mmol) in CH$_3$CN (250 mL) was added a solution of CAN (60 g, 0.11 mol) in water (150 mL) dropwise at 0° C. The mixture was stirred at 2° C. for 16 hours. The mixture was concentrated and water was added. The mixture was adjusted to pH=9 by adding saturated NaHCO$_3$ solution, and then filtered. The filtrate was separated, and the organic layer was concentrated and purified by silica gel column chromatography (DCM:MeOH=200:1 to 20:1) to give 6-(1-benzylpiperidin-4-yl)-3-(trifluoromethyl)-5,6-dihydro-1H-pyrazolo[3,4-c]pyridin-7(4H)-one (13.5 g, 60%) as an oil.

Step B: To a solution of 6-(1-benzylpiperidin-4-yl)-3-(trifluoromethyl)-5,6-dihydro-1H-pyrazolo[3,4-c]pyridin-7(4H)-one (3.5 g, 9.25 mmol) in DCM (50 mL) was added (2-(chloromethoxy)ethyl)trimethylsilane (3.1 g, 18.5 mmol) and Et$_3$N (5.5 mL, 37 mmol) at 0° C., the mixture was stirred at 50° C. for 16 hours. After water added, the mixture was extracted with DCM (100 mL×2). The combined organic layers were washed with brine, dried over anhydrous sodium sulfate and concentrated. The crude residue was purified by silica gel column chromatography (PE:EA=3:1) to give 6-(1-benzylpiperidin-4-yl)-3-(trifluoromethyl)-1-((2-(trimethylsilyl)ethoxy)methyl)-5,6-dihydro-1H-pyrazolo[3,4-c]pyridin-7(4H)-one (2.0 g, 40%) as yellow oil.

Step C: A solution of 6-(1-benzylpiperidin-4-yl)-3-(trifluoromethyl)-1-((2-(trimethylsilyl)ethoxy)methyl)-5,6-dihydro-1H-pyrazolo[3,4-c]pyridin-7(4H)-one (4.0 g, 7.86 mmol) and Pd/C (0.8 g, 10%) in methanol (50 mL) was stirred for 16 hours at 60° C. under 50 psi hydrogen pressure. The mixture was filtered, and then the filtrate was concentrated to afford 6-(piperidin-4-yl)-3-(trifluoromethyl)-1-((2-(trimethylsilyl)ethoxy)methyl)-5,6-dihydro-1H-pyrazolo[3,4-c]pyridin-7(4H)-one (3.0 g, 90%) which was used directly in the next step without further purification.

Step D: To a solution of 6-(piperidin-4-yl)-3-(trifluoromethyl)-1-((2-(trimethylsilyl)ethoxy)methyl)-5,6-dihydro-1H-pyrazolo[3,4-c]pyridin-7(4H)-one (3.0 g, 7.2 mmol) in acetic acid (30 mL) was added sodium nitrite (2.5 g, 35.8 mmol) in water (5 mL) at 15 to 20° C. The mixture was stirred at 15° C. for 0.5 hour and then at 40° C. for 2 hours. The mixture was extracted with ethyl acetate (60 mL×2), the combined organic layers were washed with brine, dried over anhydrous sodium sulfate, concentrated and purified by silica gel column chromatography (PE:EA=5:1 to 2:1) to give 6-(1-nitrosopiperidin-4-yl)-3-(trifluoromethyl)-1-((2-(trimethylsilyl)ethoxy)methyl)-5,6-dihydro-1H-pyrazolo[3,4-c]pyridin-7(4H)-one (3.0 g, 94%) as a yellow solid.

Step E: To a solution of 6-(1-nitrosopiperidin-4-yl)-3-(trifluoromethyl)-1-((2-(trimethylsilyl)ethoxy)methyl)-5,6-dihydro-1H-pyrazolo[3,4-c]pyridin-7(4H)-one (2.5 g, 5.6 mmol) and NH$_4$Cl (1.5 g, 27.9 mmol) in MeOH (40 mL) was added Zn power (1.8 g, 27.9 mmol) at 0° C. The mixture was stirred at 10° C. for 2 hours. The mixture was filtered, the filtrate was concentrated to give 6-(1-aminopiperidin-4-yl)-3-(trifluoromethyl)-1-((2-(trimethylsilyl)ethoxy)methyl)-5,6-dihydro-1H-pyrazolo[3,4-c]pyridin-7(4H)-one (2.4 g, 100%) as crude product which was used directly in the next step without further purification.

Step F: To DMF (30 mL) was added 2-(2-chloroethoxy)acetic acid (0.93 g, 6.7 mmol), HATU (2.6 g, 6.7 mmol) and DIPEA (2.6 mL), followed by added a solution of 6-(1-aminopiperidin-4-yl)-3-(trifluoromethyl)-1-((2-(trimethylsilyl)ethoxy)methyl)-5,6-dihydro-1H-pyrazolo[3,4-c]pyridin-7(4H)-one (2.4 g, 5.6 mmol) in DMF (10 mL) at 12° C. The mixture was stirred at 12° C. for 16 hours. After water was added, the mixture was extracted with EtOAc (100 mL×2). The combined organic layers were washed with aqueous sodium hydrogen carbonate solution, dried over anhydrous sodium sulfate, concentrated and purified by silica gel column chromatography (PE:EA=1:1 to 0:1) to give 2-(2-chloroethoxy)-N-(4-(7-oxo-3-(trifluoromethyl)-1-((2-(trimethylsilyl)ethoxy)methyl)-4,5-dihydro-1H-pyrazolo[3,4-c]pyridin-6(7H)-yl)piperidin-1-yl)acetamide (2.8 g, 92%) as an oil.

Step G: 2-(2-Chloroethoxy)-N-(4-(7-oxo-3-(trifluoromethyl)-1-((2-(trimethylsilyl)ethoxy)methyl)-4,5-dihydro-1H-pyrazolo[3,4-c]pyridin-6(7H)-yl)piperidin-1-yl)acetamide (2.8 g, 5.1 mmol) was dissolved in DMF (30 mL). To the solution was added NaH (305 mg, 7.6 mmol) at 0° C. The mixture was stirred at 10° C. for 1 hour. The mixture was added to saturated NH$_4$Cl solution, and extracted with EtOAc (200 mL×2). The combined organic layers were washed with brine, dried over anhydrous sodium sulfate and concentrated to give 4-(4-(7-oxo-3-(trifluoromethyl)-1-((2-(trimethylsilyl)ethoxy)methyl)-4,5-dihydro-1H-pyrazolo[3,4-c]pyridin-6(7H)-yl)piperidin-1-yl)morpholin-3-one (2.2 g, 84%) as white solid.

Step H: To a solution of 2,2,2-trifluoroacetic acid (8 mL) in DCM (30 mL) was added 4-(4-(7-oxo-3-(trifluoromethyl)-1-((2-(trimethylsilyl)ethoxy)methyl)-4,5-dihydro-1H-pyrazolo[3,4-c]pyridin-6(7H)-yl)piperidin-1-yl)morpholin-3-one (2.3 g, 4.4 mmol) at 0° C. The mixture was stirred at 0° C. for 16 hours. The mixture was concentrated and purified by silica gel column chromatography (PE:EtOAc=1:1 to 0:1) to give 4-(4-(1-(hydroxymethyl)-7-oxo-3-(trifluoromethyl)-4,5-dihydro-1H-pyrazolo[3,4-c]pyridin-6(7H)-yl)piperidin-1-yl)morpholin-3-one (1.6 g, 93%) as thick solid.

Step I: 4-(4-(1-(Hydroxymethyl)-7-oxo-3-(trifluoromethyl)-4,5-dihydro-1H-pyrazolo[3,4-c]pyridin-6(7H)-yl)piperidin-1-yl)morpholin-3-one (1.5 g, 3.6 mmol) and NH$_3$.H$_2$O (2.0 mL) was added to MeOH (20 mL). The mixture was stirred at 2° C. for 20 minutes. The mixture was concentrated to afford 4-(4-(7-oxo-3-(trifluoromethyl)-4,5-dihydro-1H-pyrazolo[3,4-c]pyridin-6(7H)-yl)piperidin-1-yl)morpholin-3-one (1.2 g, 82%) as white solid.

Step J: To dichloromethane (2.0 mL) was added 4-(4-(7-oxo-3-(trifluoromethyl)-4,5-dihydro-1H-pyrazolo[3,4-c]pyridin-6(7H)-yl)piperidin-1-yl)morpholin-3-one (60 mg, 0.2 mmol), (4-(difluoromethoxy)phenyl)boronic acid (60 mg, 0.4 mmol), and 4 Å molecular sieve (1 g) and triethylamine (0.5 mL), followed by added Cu(OAc)$_2$ (28 mg, 0.2 mmol) under N$_2$ protection at 2° C. The mixture was stirred at 2° C. for 12 hours under O$_2$ atmosphere. The reaction mixture was filtered, the filtrate was concentrated and purified by preparative HPLC (HCOOH) to afford 4-(4-(1-(4-(difluoromethoxy)phenyl)-7-oxo-3-(trifluoromethyl)-4,5-dihydro-1H-pyrazolo[3,4-c]pyridin-6(7H)-yl)piperidin-1-yl)morpholin-3-one (30 mg, 37%) as white solid. $^1$H NMR (DMSO-d$_6$, 400 MHz) δ 7.64 (dd, J$_1$=8.0 Hz, J$_2$=3.2 Hz, 2H), 7.30 (dd, J$_1$=8.0 Hz, J$_2$=3.2 Hz, 2H), 7.36 (t, J=74.0 Hz, 1H), 4.25-4.22 (m, 1H), 3.98 (s, 2H), 3.82-3.79 (m, 2H), 3.64-3.61 (m, 2H), 3.43-3.40 (m, 4H), 3.00-3.05 (m, 2H), 2.91-2.86 (m, 2H), 1.83-1.79 (m, 2H), 1.61-1.58 (m, 2H).

Example 24

4-(4-(1-(6-Chloronaphthalen-2-yl)-7-oxo-3-(trifluoromethyl)-4,5-dihydro-1H-pyrazolo[3,4-c]pyridin-6(7H)-yl)piperidin-1-yl)morpholin-3-one

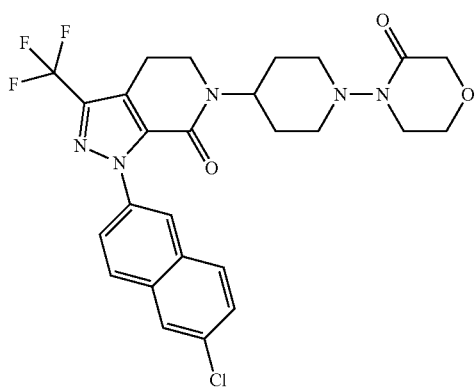 [SMILES: O=C1c2c(c(C(F)(F)F)nn2-c2ccc3cc(Cl)ccc3c2)CCN1C1CCN(N2CCOCC2=O)CC1]

Step A: 4-(4-(1-(6-Chloronaphthalen-2-yl)-7-oxo-3-(trifluoromethyl)-4,5-dihydro-1H-pyrazolo[3,4-c]pyridin-6(7H)-yl)piperidin-1-yl)morpholin-3-one is prepared according to the procedure used for the preparation of example 24, step J, replacing (4-(difluoromethoxy)phenyl)boronic acid by (6-chloronaphthalen-2-yl)boronic acid. The crude was purified by pre-HPLC (FA) to give the title compound as a white solid. $^1$HNMR (DMSO-d$_6$, 400 MHz) δ 8.22-8.19 (m, 2H), 8.11 (d, J=8.8 Hz, 1H), 8.03 (d, J=8.8 Hz, 1H), 7.76 (d, J=8.8 Hz, 1H), 7.63 (d, J=8.8 Hz, 1H), 4.26-4.23 (m, 1H), 3.97 (s, 2H), 3.81-3.78 (m, 2H), 3.66-3.62 (m, 2H), 3.43-3.40 (m, 4H), 3.08-3.05 (m, 2H), 2.98-2.90 (m, 2H), 1.83-1.79 (m, 2H), 1.62-1.58 (m, 2H).

Example 25

2-Fluoro-5-(7-oxo-6-(1-(3-oxomorpholino)piperidin-4-yl)-3-(trifluoromethyl)-4,5,6,7-tetra hydro-1H-pyrazolo[3,4-c]pyridin-1-yl)benzonitrile

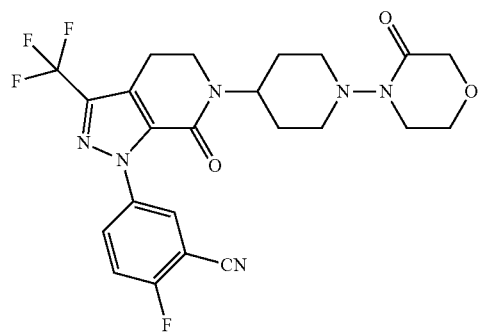 [SMILES: N#Cc1cc(-n2nc(C(F)(F)F)c3c2C(=O)N(C2CCN(N4CCOCC4=O)CC2)CC3)ccc1F]

Step A: 2-Fluoro-5-(7-oxo-6-(1-(3-oxomorpholino)piperidin-4-yl)-3-(trifluoromethyl)-4,5,6,7-tetra hydro-1H-pyrazolo[3,4-c]pyridin-1-yl)benzonitrile is prepared according to the procedure used for the preparation of example 24, step J, replacing (4-(difluoromethoxy)phenyl)boronic acid by (3-cyano-4-fluorophenyl)boronic acid. $^1$H NMR (DMSO-d$_6$, 400 MHz) δ 8.32 (dd, J$_1$=6.4 Hz, J$_2$=2.4 Hz, 1H), 8.05 (dd, J$_1$=7.2 Hz, J$_2$=4.4 Hz, 1H), 7.71 (d, J=8.8 Hz, 1H), 4.26-4.23 (m, 1H), 3.98 (s, 2H), 3.82-3.80 (m, 2H), 3.66-3.62 (m, 2H), 3.43-3.40 (m, 4H), 3.08-3.05 (m, 2H), 2.98-2.90 (m, 2H), 1.83-1.80 (m, 2H), 1.62-1.59 (m, 2H).

Example 26

4-(4-(1-(3-Aminobenzo[d]isoxazol-5-yl)-7-oxo-3-(trifluoromethyl)-4,5-dihydro-1H-pyrazolo[3,4-c]pyridin-6(7H)-yl)piperidin-1-yl)morpholin-3-one

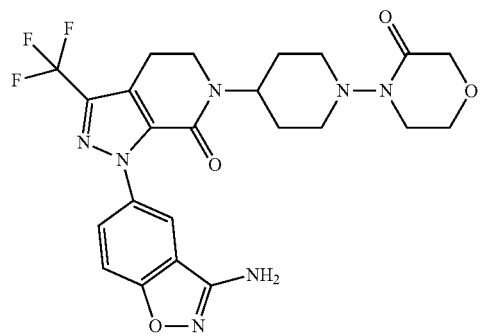 [SMILES: Nc1noc2ccc(-n3nc(C(F)(F)F)c4c3C(=O)N(C3CCN(N5CCOCC5=O)CC3)CC4)cc12]

Step A: 4-(4-(1-(3-Aminobenzo[d]isoxazol-5-yl)-7-oxo-3-(trifluoromethyl)-4,5-dihydro-1H-pyrazolo[3,4-c]pyridin-6(7H)-yl)piperidin-1-yl)morpholin-3-one is prepared according to the procedure used for the preparation of example 24, step J, replacing (4-(difluoromethoxy)phenyl) boronic acid by (3-aminobenzo[d]isoxazol-5-yl)boronic acid. $^1$H NMR (DMSO-d$_6$, 400 MHz) δ 8.05 (d, J=2.0 Hz, 1H), 7.71 (d, J=9.2 Hz, 1H), 7.56 (d, J=8.8 Hz, 1H), 6.59 (s, 2H), 4.25-4.23 (m, 1H), 3.98 (s, 2H), 3.82-3.80 (m, 2H), 3.66-3.62 (m, 2H), 3.43-3.40 (m, 4H), 3.08-3.05 (m, 2H), 2.98-2.90 (m, 2H), 1.84-1.81 (m, 2H), 1.60-1.58 (m, 2H).

Example 27

3-(7-Oxo-6-(1-(3-oxomorpholino)piperidin-4-yl)-3-(trifluoromethyl)-4,5,6,7-tetrahydro-1H-pyrazolo[3,4-c]pyridin-1-yl)benzonitrile

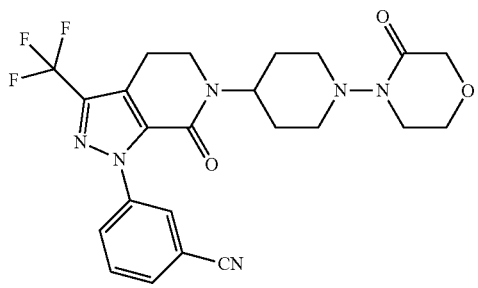 [SMILES: N#Cc1cccc(-n2nc(C(F)(F)F)c3c2C(=O)N(C2CCN(N4CCOCC4=O)CC2)CC3)c1]

Step A: 3-(7-Oxo-6-(1-(3-oxomorpholino)piperidin-4-yl)-3-(trifluoromethyl)-4,5,6,7-tetrahydro-1H-pyrazolo[3,4-c]pyridin-1-yl)benzonitrile is prepared according to the procedure used for the preparation of example 24, step J, replacing (4-(difluoromethoxy)phenyl)boronic acid by (3-cyanophenyl)boronic acid. $^1$H NMR (DMSO-d$_6$, 400 MHz) δ 8.19 (s, 1H), 8.00-7.95 (m, 2H), 7.75-7.72 (m, 1H), 4.25-4.23 (m, 1H), 3.98 (s, 2H), 3.82-3.80 (m, 2H), 3.66-3.62 (m, 2H), 3.43-3.40 (m, 4H), 3.08-3.05 (m, 2H), 2.98-2.90 (m, 2H), 1.84-1.81 (m, 2H), 1.60-1.58 (m, 2H).

Example 28

4-(4-(1-(3-Fluoro-4-methoxyphenyl)-7-oxo-3-(trifluoromethyl)-4,5-dihydro-1H-pyrazolo[3,4-c]pyridin-6(7H)-yl)piperidin-1-yl)morpholin-3-one

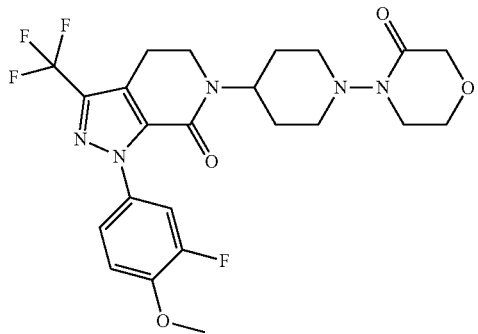 [SMILES: COc1ccc(-n2nc(C(F)(F)F)c3c2C(=O)N(C2CCN(N4CCOCC4=O)CC2)CC3)cc1F]

Step A: 4-(4-(1-(3-Fluoro-4-methoxyphenyl)-7-oxo-3-(trifluoromethyl)-4,5-dihydro-1H-pyrazolo[3,4-c]pyridin-6(7H)-yl)piperidin-1-yl)morpholin-3-one is prepared according to the procedure used for the preparation of example 24, step J, replacing (4-(difluoromethoxy)phenyl)boronic acid by (3-fluoro-4-methoxyphenyl)boronic acid. $^1$H NMR (DMSO-d$_6$, 400 MHz) δ 7.55 (d, J=11.6 Hz, 1H), 7.38-7.36 (m, 1H), 7.27 (t, J=8.8 Hz, 1H), 4.26-4.23 (m, 1H), 3.98 (s, 2H), 3.92 (s, 3H), 3.81-3.80 (m, 2H), 3.61-3.60 (m, 2H), 3.43-3.40 (m, 4H), 3.03-3.01 (m, 2H), 2.91-2.90 (m, 2H), 1.84-1.79 (m, 2H), 1.61-1.58 (m, 2H).

Example 29

4-(4-(1-(3-Fluoronaphthalen-2-yl)-7-oxo-3-(trifluoromethyl)-4,5-dihydro-1H-pyrazolo[3,4-c]pyridin-6(7H)-yl)piperidin-1-yl)morpholin-3-one

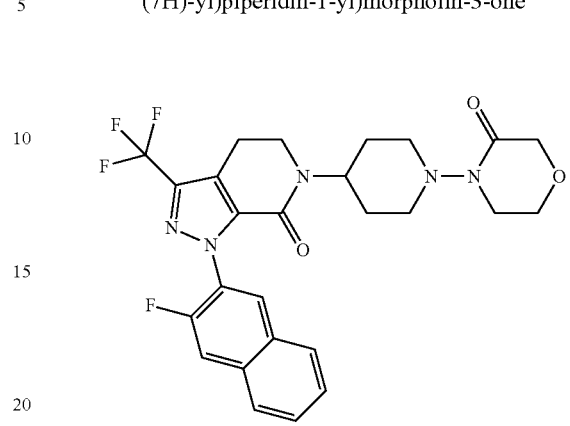

Step A: 4-(4-(1-(3-Fluoronaphthalen-2-yl)-7-oxo-3-(trifluoromethyl)-4,5-dihydro-1H-pyrazolo[3,4-c]pyridin-6(7H)-yl)piperidin-1-yl)morpholin-3-one is prepared according to the procedure used for the preparation of example 24, step J, replacing (4-(difluoromethoxy)phenyl)boronic acid by (3-fluoronaphthalen-2-yl)boronic acid. $^1$H NMR (DMSO-d$_6$, 400 MHz) δ 8.29 (d, J=7.6 Hz, 1H), 8.09-7.02 (m, 3H), 7.78 (d, J=7.6 Hz, 1H), 7.62 (d, J=8.0 Hz, 1H), 4.25-4.20 (m, 1H), 3.96 (s, 2H), 3.80-3.79 (m, 2H), 3.66-3.62 (m, 2H), 3.43-3.40 (m, 4H), 3.00-2.98 (m, 4H), 1.84-1.78 (m, 2H), 1.58-1.56 (m, 2H).

Example 30

2-(Difluoromethoxy)-5-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzonitrile

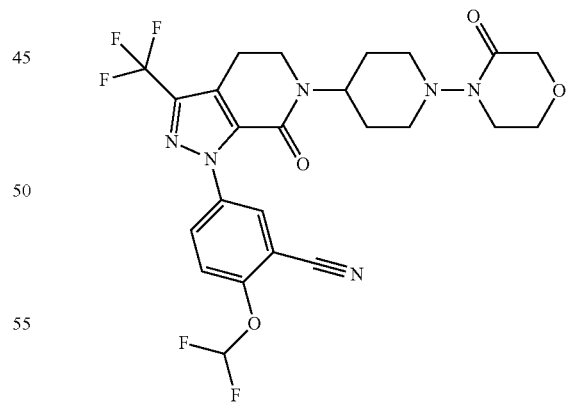

Step A: 2-(Difluoromethoxy)-5-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzonitrile is prepared according to the procedure used for the preparation of example 24, step J, replacing (4-(difluoromethoxy)phenyl)boronic acid by (3-cyano-4-(difluoromethoxy)phenyl)boronic acid. $^1$H NMR (DMSO-d$_6$, 400 MHz) δ 8.31 (d, J=2.8 Hz, 1H), 8.04 (dd, J$_1$=9.2 Hz, J$_2$=2.8 Hz, 1H), 7.62 (d, J=9.2

Hz, 1H), 7.56 (t, J=72.0 Hz, 1H), 4.28-4.20 (m, 1H), 3.98 (s, 2H), 3.81-3.79 (m, 2H), 3.65-3.62 (m, 2H), 3.43-3.40 (m, 4H), 3.00-2.98 (m, 4H), 1.83-1.78 (m, 2H), 1.62-1.59 (m, 2H).

Example 31

3-(7-Oxo-6-(1-(3-oxomorpholino)piperidin-4-yl)-3-(trifluoromethyl)-4,5,6,7-tetrahydro-1H-pyrazolo[3,4-c]pyridin-1-yl)benzamide

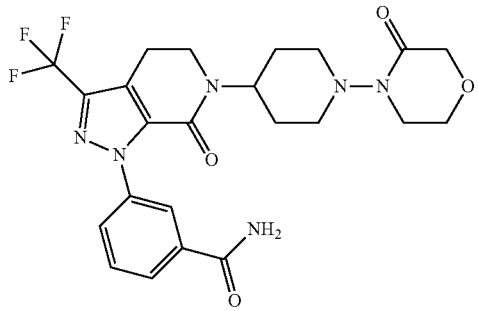 [SMILES: NC(=O)c1cccc(-n2nc(C(F)(F)F)c3c2C(=O)N(C2CCN(N4CCOCC4=O)CC2)CC3)c1]

Step A: 3-(7-Oxo-6-(1-(3-oxomorpholino)piperidin-4-yl)-3-(trifluoromethyl)-4,5,6,7-tetrahydro-1H-pyrazolo[3,4-c]pyridin-1-yl)benzonitrile (100 mg, 0.205 mmol) and $K_2CO_3$ (57 mg, 0.41 mmol) was dissolved in DMSO (2 mL). Then $H_2O_2$ (21 mg, 0.615 mmol) was added to the mixture. The resulting mixture was stirred at 20° C. for 3 hours. The mixture was washed with saturated $Na_2S_2O_3$ (5 mL) aqueous solution, extracted with EtOAc (10 mL×2), and concentrated. The crude residue was purified by preparative HPLC (HCOOH) to afford 3-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzamide (10.2 mg, 10% yield) as white solid. $^1$HNMR (DMSO-$d_6$, 400 MHz) δ 8.12 (s, 1H), 8.04-7.99 (m, 2H), 7.72 (d, J=2.8 Hz, 1H), 7.21 (d, J=4.0 Hz, 1H), 7.61-7.56 (m, 2H), 4.28-4.25 (m, 1H), 3.98 (s, 2H), 3.81-3.79 (m, 2H), 3.65-3.62 (m, 2H), 3.43-3.40 (m, 4H), 3.00-2.98 (m, 4H), 1.83-1.78 (m, 2H), 1.61-1.59 (m, 2H).

Example 32

2-Fluoro-5-(7-oxo-6-(1-(3-oxomorpholino)piperidin-4-yl)-3-(trifluoromethyl)-4,5,6,7-tetra hydro-1H-pyrazolo[3,4-c]pyridin-1-yl)benzamide

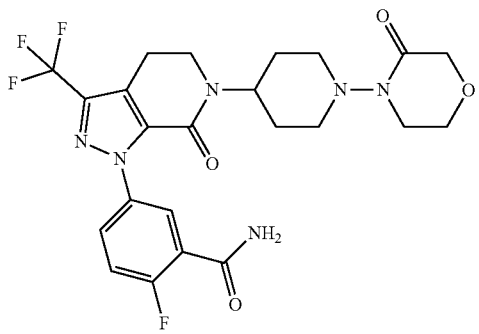 [SMILES: NC(=O)c1cc(-n2nc(C(F)(F)F)c3c2C(=O)N(C2CCN(N4CCOCC4=O)CC2)CC3)ccc1F]

Step A: 2-Fluoro-5-(7-oxo-6-(1-(3-oxomorpholino)piperidin-4-yl)-3-(trifluoromethyl)-4,5,6,7-tetra hydro-1H-pyrazolo[3,4-c]pyridin-1-yl)benzamide is prepared according to the procedure used for the preparation of example 31, step A. $^1$HNMR (DMSO-$d_6$, 400 MHz) δ 7.90 (s, 1H), 7.85-7.82 (m, 2H), 7.79-7.85 (m, 1H), 7.45 (t, J=8.8 Hz, 1H), 4.28-4.25 (m, 1H), 3.98 (s, 2H), 3.81-3.79 (m, 2H), 3.65-3.62 (m, 2H), 3.43-3.40 (m, 4H), 3.00-2.98 (m, 4H), 1.83-1.78 (m, 2H), 1.61-1.53 (m, 2H).

Example 33

2-(Difluoromethoxy)-5-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzamide

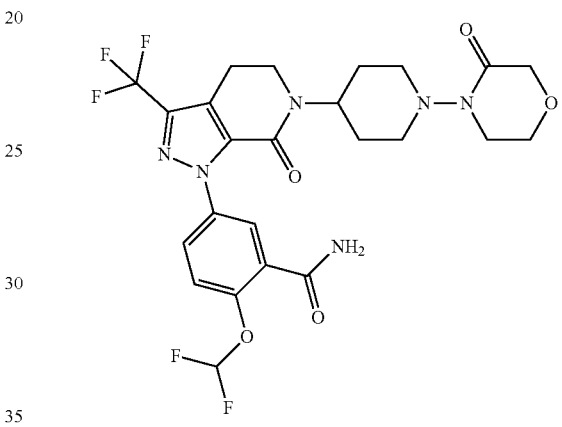

Step A: 2-(Difluoromethoxy)-5-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzamide is prepared according to the procedure used for the preparation of example 31, step A. $^1$HNMR (DMSO-$d_6$, 400 MHz) δ 7.83 (s, 1H), 7.76-7.70 (m, 3H), 7.35 (d, J=8.8 Hz, 1H), 7.27 (t, J=72 Hz, 1H), 4.28-4.25 (m, 1H), 3.98 (s, 2H), 3.81-3.79 (m, 2H), 3.65-3.62 (m, 2H), 3.43-3.40 (m, 4H), 3.00-2.98 (m, 4H), 1.83-1.78 (m, 2H), 1.61-1.55 (m, 2H).

In Vitro Studies

The ability of test compounds to inhibit human or rat factor Xa or other enzymes such as thrombin or trypsin are assessed by measuring the concentration of the compounds of the formula that inhibits enzyme activity by 50%, i.e. The $IC_{50}$ value, which is related to the inhibition constant Ki. Purified enzymes are used in chromogenic assays. The initial velocity of chromogenic substrate hydrolysis is measured by measuring the variation of the absorbance at 405 nm of the linear portion of the time course (usually 2-10 minutes after addition of substrate) with FlexStation III (Molecular Devices) at 37° C. The concentration of inhibitor that cause a 50% decrease in the rate of substrate hydrolysis is measured by calculating linear regression after plotting the logarithmic curve of relative rates of hydrolysis (compared to the uninhibited control) versus the concentration of the tested compound. The inhibitory constant ($K_i$) against enzymes is calculated according to the Cheng-Prusoff equation: $K_i=IC_{50}/(1+[S]/K_m)$, wherein [S] is the substrate concentration, and $K_m$ is the Michaelis-Menten constant. $K_m$ is measured from a Line weaver-Burk plot. $IC_{50}$ values of tested compounds are got from GraphPad Prism software. The curve is fitted using "Sigmoidal dose-response (variable slope)".

Human/Rat Factor Xa Assay

In the assay for measuring the inhibition of human or rat factor Xa activity, Tris-HCl buffer (50 mM, pH 8.3, 150 mM NaCl) is used. The $IC_{50}$ is measured by adding dropwise the assay buffer of 50 μL human Factor Xa (Enzyme Research Laboratories, Inc; the final concentration of 8.36 nM) or 50 μL rat Factor Xa (Enzyme Research Laboratories, Inc; the final concentration of 57.5 nM) to the appropriate wells of a Greiner 384 microtiter plate. 2 μL the assay buffer containing 2% (V/V) DMSO (uninhibited control) or various concentrations of the compounds to be tested is diluted in the assay buffer containing 2% (V/V) DMSO, and add the assay buffer of 48 μL substrate S-2222 (Chromogenix; chemical formula: Bz-Ile-Glu(γ-OR)-Gly-Arg-pNA.HCl R=H (50%) and R=$CH_3$ (50%)), the final concentration is 0.172 mM. The assay is performed by pre-incubating the tested compounds with enzyme for 10 min, and then the assay is initiated by adding substrate S-2222 to obtain a final volume of 100 μL.

Compounds tested in the above assay are considered to be active if they exhibit a Ki of <10 μM. Preferred compounds of the present invention have Ki's of <1 μM. More preferred compounds of the present invention have Ki's of <0.1 μM. Even more preferred compounds of the present invention have Ki's of <0.01 μM. Still more preferred compounds of the present invention have Ki's of <0.001 μM. Using the method described above, a number of compounds of the present invention are found to exhibit Ki's of <0.1 μM, thereby confirming the utility of the compounds of the present invention as effective factor Xa inhibitors.

Human Thrombin Assay

In the assay for measuring the inhibition of human thrombin activity buffer (10 mM HEPES buffer, pH 7.4, 2 mM $CaCl_2$) is used. The $IC_{50}$ is measured by selecting the appropriate wells of a Greiner 384 microtiter plate. 50 μL the assay buffer containing human thrombin (Sigma; T8885), of which the final concentration is 0.05 NIH units/ml; 2 μL the assay buffer containing 2% (V/V) DMSO (uninhibited control) or various concentrations of the compounds to be tested diluted in the assay buffer containing 2% (V/V) DMSO; and add 48 μL the assay buffer containing substrate S-2238 (Chromogenix; Chemical Formula: H-D-Phe-Pip-Arg-pNA*2HCl), the final concentration is 30 μM. The assay is performed by pre-incubating the tested compounds with enzyme for 10 minutes. Then the assay is initiated by adding substrate to obtain a final volume of 100 μL.

Human Trypsin Assay

In the assay for measuring the inhibition of human trypsin activity buffer (50 mM Tris, pH 8.2, and 20 mM $CaCl_2$) is used. The $IC_{50}$ is measured by selecting the appropriate wells of a Greiner 384 microtiter plate. 50 μL the assay buffer containing human trypsin (Sigma; T6424), of which the final concentration is 0.39 BAEE units/ml; 2 μL the assay buffer containing 2% (V/V) DMSO (uninhibited control) or various concentrations of the compounds to be tested diluted in the assay buffer containing 2% (V/V) DMSO; and the assay buffer containing substrate S-2222 (Chromogenix). The assay is performed by pre-incubating the tested compounds with enzyme for 10 minutes. Then the assay is initiated by adding 48 μL substrate to obtain a final volume of 100 μL.

Prothrombinase Assay

The effect of test compounds on prothrombinase activity is measured via thrombin generation. Briefly, 12.5 μL human factor Xa is incubated in 10 mM HEPES buffer, pH 7.4, 2 mM $CaCl_2$, the final concentration is 0.5 nM, and add 12.5 μL human platelets ($1\times10^7$ $mL^{-1}$) for 10 minutes at 37° C. The reaction is initiated by adding 25 μL prothrombin, the final concentration is 0.5 μM and 2 μL the assay buffer containing 2% (V/V) DMSO (uninhibited control) or various concentrations of the compounds to be tested diluted in the assay buffer containing 2% (V/V) DMSO. After 20 minutes, thrombin activity is measured by adding 48 μL substrate of S-2238 (Chromogenix) at the final concentration is 50 μM.

Table 1: In Vitro Screening Results of the Compound of this Invention

TABLE 1

| Test Compound | hfXa Ki (nM) | rfXa Ki (nM) | thrombin Ki (nM) | trypsin Ki (nM) | prothrombinase Ki (nM) |
|---|---|---|---|---|---|
| Apixaban | A | B | D | D | A |
| 1 | A | A | D | D | A |
| 2 | A | A | D | D | A |
| 3 | A | A | D | D | A |
| 4 | A | B | D | D | A |
| 5 | B | B | D | D | A |
| 6 | A | B | D | D | A |
| 7 | A | B | D | D | A |
| 8a | C | B | N/A | N/A | N/A |
| 8b | A | B | D | D | B |
| 9 | B | N/A | N/A | N/A | N/A |
| 10 | A | C | D | D | C |
| 11 | A | B | D | D | A |
| 12 | B | N/A | N/A | N/A | N/A |
| 13 | B | N/A | N/A | N/A | N/A |
| 14 | A | C | D | D | A |
| 15 | B | N/A | N/A | N/A | B |
| 16 | C | N/A | N/A | N/A | N/A |
| 17 | C | N/A | N/A | N/A | N/A |
| 18 | C | N/A | N/A | N/A | N/A |
| 19 | C | N/A | N/A | N/A | N/A |
| 20 | B | N/A | N/A | N/A | N/A |
| 21 | C | N/A | N/A | N/A | N/A |
| 22 | C | N/A | N/A | N/A | N/A |
| 23 | A | B | D | D | A |
| 24 | A | A | D | D | A |
| 25 | C | N/A | N/A | N/A | N/A |
| 26 | A | A | D | D | A |
| 27 | B | N/A | N/A | N/A | N/A |
| 28 | A | A | D | D | A |
| 29 | A | A | D | D | A |
| 30 | C | N/A | N/A | N/A | N/A |
| 31 | A | B | D | D | B |
| 32 | C | N/A | N/A | N/A | N/A |
| 33 | C | N/A | N/A | N/A | N/A |

Remarks:
1. "a" and "b" means the fraction 1 and fraction 2 of compoumds respectively after SFC separation.
2. The above compounds of which the enzyme activity was tested were divided into A to D four part according to the magnitude of the activity, wherein, A ≤10 nm; 10 nm < B ≤ 50 nm; 1000 nm > C ≥ 50 nm; D ≥1000 nm; N/A means not tested.

As is evident from the results shown, the compound of the present invention show a strong anticoagulant activity through its specific anticoagulant factor Xa activity, in comparison with apixaban which is generally known as an anticoagulant agent.

What is claimed is:

1. A compound of formula (II) or a pharmaceutically acceptable salt thereof,

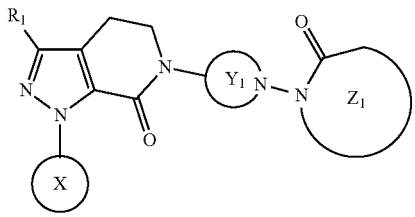
(II)

wherein,
the structure unit

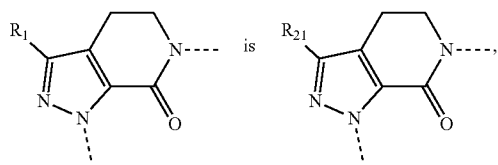 is in which $R_{21}$ is H, F, Cl, Br, I, CN, OH, SH, $NH_2$, CHO, COOH, $CF_3$, $CH_3$, $CH_3CH_2$, cyclopropyl, —C(=O)$NH_2$, or

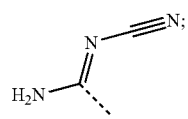

X is selected from

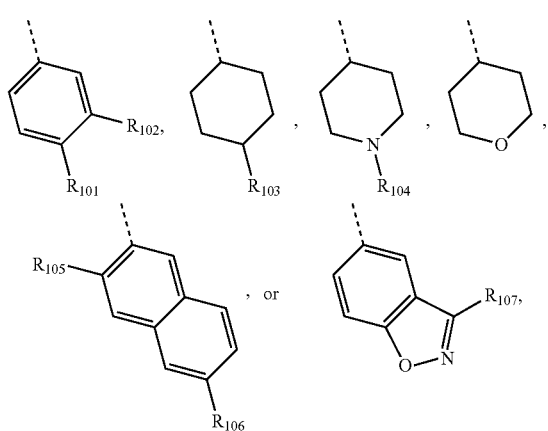

in which $R_{101-107}$ are independently selected from $CH_3O$—, F, Cl, CN, $NH_2$, $CF_3O$—, $CHF_2O$—, —C(=O)$NH_2$, $CH_3S(=O)_2$— respectively;

$Y_1$ is selected from the group consisting of

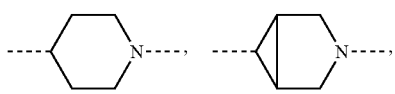

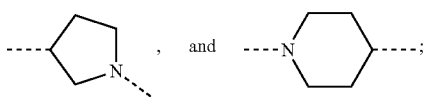

and $Z_1$ is selected from

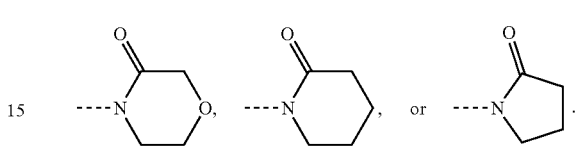

2. A compound of formula (II) or pharmaceutically acceptable salt thereof,

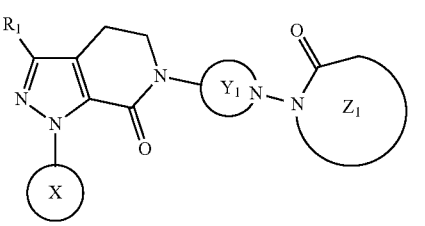
(II)

wherein
the structure unit

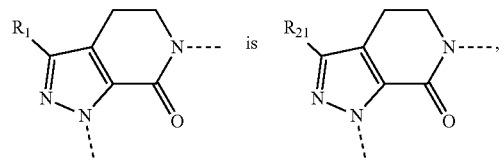 is in which $R_{21}$ is H, F, Cl, Br, I, CN, OH, SH, $NH_2$, CHO, COOH, $CF_3$, $CH_3$, $CH_3CH_2$, cyclopropyl, —C(=O)$NH_2$, or

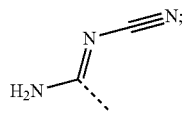

X is selected from

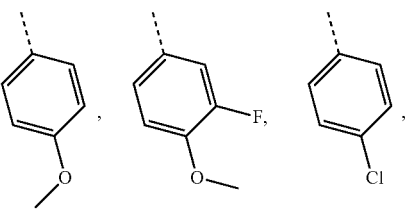

-continued
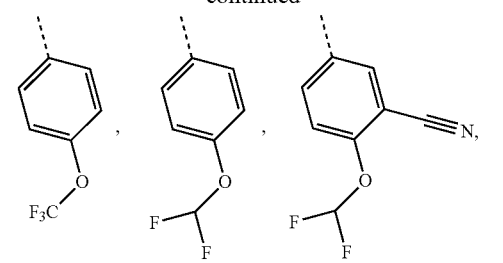
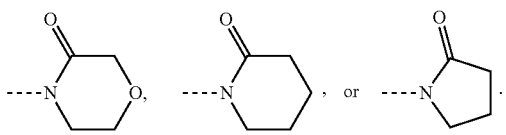
and
Z₁ is selected from
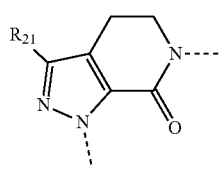
3. The compound or pharmaceutically acceptable salt thereof of claim 1, wherein the structure unit
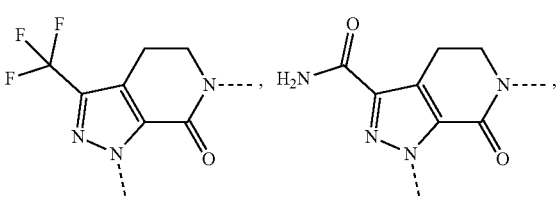
is selected from
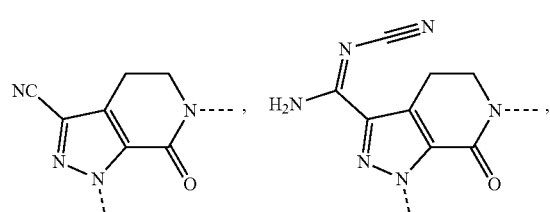
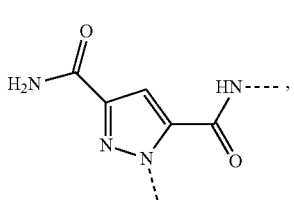
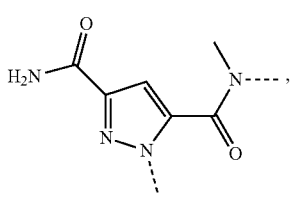
Y₁ is selected from the group consisting of

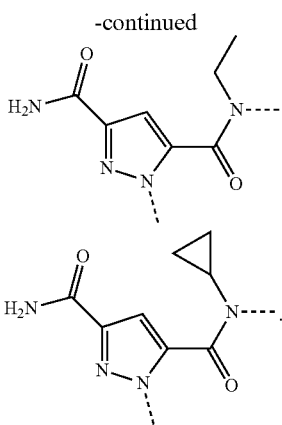

4. The compound or pharmaceutically acceptable salt thereof of claim 1, wherein the compound is selected from:
1) 4-(4-(1-(4-Methoxyphenyl)-7-oxo-3-(trifluoromethyl)-4,5-dihydro-1H-pyrazolo[3,4-c]pyridin-6(7H)-yl)piperidin-1-yl)morpholin-3-one;
2) 1-(4-Methoxyphenyl)-6-(2'-oxo-[1,1'-bipiperidin]-4-yl)-3-(trifluoromethyl)-5,6-dihydro-1H-pyrazolo[3,4-c]pyridin-7(4H)-one;
3) 1-(4-Methoxyphenyl)-6-(1-(2-oxopyrrolidin-1-yl)piperidin-4-yl)-3-(trifluoromethyl)-5,6-dihydro-1H-pyrazolo[3,4-c]pyridin-7(4H)-one;
4) 1-(4-Methoxyphenyl)-7-oxo-6-(2'-oxo-[1,1'-bipiperidin]-4-yl)-4,5,6,7-tetrahydro-1H-pyrazolo[3,4-c]pyridine-3-carboxamide;
5) 1-(4-Methoxyphenyl)-7-oxo-6-(2'-oxo-[1,1'-bipiperidin]-4-yl)-4,5,6,7-tetrahydro-1H-pyrazolo[3,4-c]pyridine-3-carbonitrile;
6) N'-Cyano-1-(4-methoxyphenyl)-7-oxo-6-(2'-oxo-[1,1'-bipiperidin]-4-yl)-4,5,6,7-tetrahydro-1H-pyrazolo[3,4-c]pyridine-3-carboximidamide;
7) 1-(4-Methoxyphenyl)-7-oxo-6-(1-(3-oxomorpholino)piperidin-4-yl)-4,5,6,7-tetrahydro-1H-pyrazolo[3,4-c]pyridine-3-carboxamide;
8) 1-(4-Methoxyphenyl)-7-oxo-6-(1-(2-oxopyrrolidin-3-yl)piperidin-4-yl)-4,5,6,7-tetrahydro-1H-pyrazolo[3,4-c]pyridine-3-carboxamide;
9) 1-(4-Chlorophenyl)-7-oxo-6-(1-(3-oxomorpholino)piperidin-4-yl)-4,5,6,7-tetrahydro-1H-pyrazolo[3,4-c]pyridine-3-carboxamide;
10) 7-oxo-6-(1-(3-oxomorpholino)piperidin-4-yl)-1-(4-(trifluoromethoxy)phenyl)-4,5,6,7-tetrahydro-1H-pyrazolo[3,4-c]pyridine-3-carboxamide;
11) 1-(4-(Difluoromethoxy)phenyl)-7-oxo-6-(1-(3-oxomorpholino)piperidin-4-yl)-4,5,6,7-tetrahydro-1H-pyrazolo[3,4-c]pyridine-3-carboxamide;
12) 1-(4-Methoxyphenyl)-7-oxo-6-(3-(2-oxopiperidin-1-yl)-3-azabicyclo[3.1.0]hexan-6-yl)-4,5,6,7-tetrahydro-1H-pyrazolo[3,4-c]pyridine-3-carboxamide;
13) 1-(4-Methoxyphenyl)-7-oxo-6-(3-(3-oxomorpholino)-3-azabicyclo[3.1.0]hexan-6-yl)-4,5,6,7-tetrahydro-1H-pyrazolo[3,4-c]pyridine-3-carboxamide;
14) 1-(4-Methoxyphenyl)-7-oxo-6-(2-oxo-[1,4'-bipiperidin]-1'-yl)-4,5,6,7-tetrahydro-1H-pyrazolo[3,4-c]pyridine-3-carboxamide;
15) 1-(4-Methoxyphenyl)-$N^5$-(1-(3-oxomorpholino)piperidin-4-yl)-1H-pyrazole-3,5-dicarboxamide;
16) 1-(4-Methoxyphenyl)-$N^5$-methyl-$N^5$-(1-(3-oxomorpholino)piperidin-4-yl)-1H-pyrazole-3,5-dicarboxamide;
17) $N^5$-Ethyl-1-(4-methoxyphenyl)-$N^5$-(1-(3-oxomorpholino)piperidin-4-yl)-1H-pyrazole-3,5-dicarboxamide;
18) $N^5$-cyclopropyl-1-(4-methoxyphenyl)-$N^5$-(1-(3-oxomorpholino)piperidin-4-yl)-1H-pyrazole-3,5-dicarboxamide;
19) 1-(4-Methoxyphenyl)-$N^5$-(1-(3-oxomorpholino)pyrrolidin-3-yl)-1H-pyrazole-3,5-dicarboxamide;
20) $N^5$-(1-(3-oxomorpholino)piperidin-4-yl)-1-(tetrahydro-2H-pyran-4-yl)-1H-pyrazole-3,5-dicarboxamide;
21) 1-(1-(Methylsulfonyl)piperidin-4-yl)-$N^5$-(1-(3-oxomorpholino)piperidin-4-yl)-1H-pyrazole-3,5-dicarboxamide;
22) 1-(4-Methoxycyclohexyl)-$N^5$-(1-(3-oxomorpholino)piperidin-4-yl)-1H-pyrazole-3,5-dicarboxamide;
23) 4-(4-(1-(4-(Difluoromethoxy)phenyl)-7-oxo-3-(trifluoromethyl)-4,5-dihydro-1H-pyrazolo[3,4-c]pyridin-6(7H)-yl)piperidin-1-yl)morpholin-3-one;
24) 4-(4-(1-(6-Chloronaphthalen-2-yl)-7-oxo-3-(trifluoromethyl)-4,5-dihydro-1H-pyrazolo[3,4-c]pyridin-6(7H)-yl)piperidin-1-yl)morpholin-3-one;
25) 2-Fluoro-5-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzonitrile;
26) 4-(4-(1-(3-Aminobenzo[d]isoxazol-5-yl)-7-oxo-3-(trifluoromethyl)-4,5-dihydro-1H-pyrazolo[3,4-c]pyridin-6(7H)-yl)piperidin-1-yl)morpholin-3-one;
27) 3-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzonitrile;
28) 4-(4-(1-(3-Fluoro-4-methoxyphenyl)-7-oxo-3-(trifluoromethyl)-4,5-dihydro-1H-pyrazolo[3,4-c]pyridin-6(7H)-yl)piperidin-1-yl)morpholin-3-one;
29) 4-(4-(1-(3-Fluoronaphthalen-2-yl)-7-oxo-3-(trifluoromethyl)-4,5-dihydro-1H-pyrazolo[3,4-c]pyridin-6(7H)-yl)piperidin-1-yl)morpholin-3-one;
30) 2-(Difluoromethoxy)-5-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzonitrile;
31) 3-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzamide;
32) 2-Fluoro-5-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzamide; and
33) 2-(Difluoromethoxy)-5-(7-oxo-6-(1-(3-oxomorpholino)piperidin-4-yl)-3-(trifluoromethyl)-4,5,6,7-tetrahydro-1H-pyrazolo[3,4-c]pyridin-1-yl)benzamide.

5. A process for preparing the compound of formula (I) of claim 1, comprising a route which is as follows:

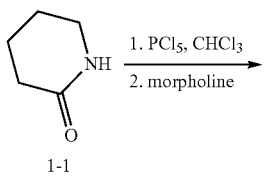

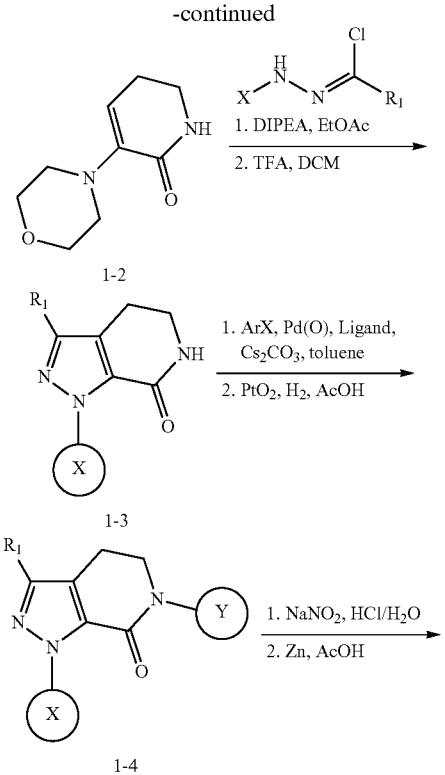
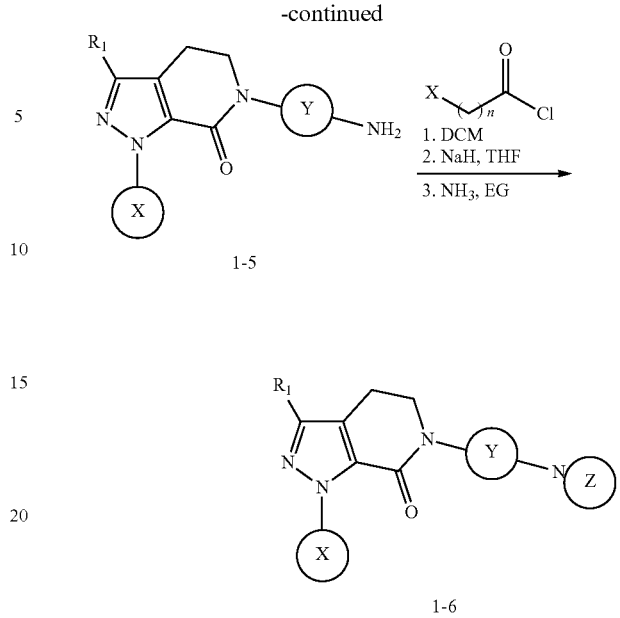
wherein R¹, X, Y, and Z are as defined in claim 1.
* * * * *